(12) United States Patent
Toyofuku et al.

(10) Patent No.: US 9,493,484 B2
(45) Date of Patent: Nov. 15, 2016

(54) HETEROCYCLIC COMPOUND AND USE THEREOF

(71) Applicant: Takeda Pharmaceutical Company Limited, Osaka-shi, Osaka (JP)

(72) Inventors: Masashi Toyofuku, Kanagawa (JP); Shinji Nakamura, Kanagawa (JP); Eiji Honda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/377,106

(22) PCT Filed: Feb. 7, 2013

(86) PCT No.: PCT/JP2013/052950
§ 371 (c)(1),
(2) Date: Aug. 6, 2014

(87) PCT Pub. No.: WO2013/118845
PCT Pub. Date: Aug. 15, 2013

(65) Prior Publication Data
US 2015/0051197 A1 Feb. 19, 2015

(30) Foreign Application Priority Data

Feb. 8, 2012 (JP) .................. 2012-025610

(51) Int. Cl.
| C07D 513/04 | (2006.01) |
|---|---|
| C07D 513/08 | (2006.01) |
| C07D 513/18 | (2006.01) |

(52) U.S. Cl.
CPC ........... *C07D 513/08* (2013.01); *C07D 513/04* (2013.01); *C07D 513/18* (2013.01)

(58) Field of Classification Search
CPC .................................................. C07D 513/04
USPC ........................................ 544/10; 514/222.8
See application file for complete search history.

(56) References Cited

U.S. PATENT DOCUMENTS

| 7,253,163 B2 | 8/2007 | Desos et al. |
|---|---|---|
| 7,262,190 B2 | 8/2007 | Desos et al. |
| 8,236,790 B2 | 8/2012 | Cordi et al. |
| 2004/0254161 A1 | 12/2004 | Desos et al. |
| 2004/0254371 A1 | 12/2004 | Desos et al. |
| 2005/0124606 A1 | 6/2005 | Cordi et al. |
| 2010/0240635 A1 | 9/2010 | Cordi et al. |
| 2010/0247514 A1 | 9/2010 | Zhu et al. |
| 2011/0118236 A1 | 5/2011 | Mochizuki et al. |
| 2012/0107328 A1 | 5/2012 | Greenlee et al. |

FOREIGN PATENT DOCUMENTS

| JP | 2-085851 | 3/1990 |
|---|---|---|
| JP | 4-037742 | 2/1992 |
| JP | 2005-002113 | 1/2005 |
| JP | 2006-188506 | 7/2006 |
| JP | 2009-248543 | 10/2009 |
| JP | 2010-508328 | 3/2010 |
| JP | 2010-526808 | 8/2010 |
| JP | 2011-503002 | 1/2011 |
| WO | 03/053979 | 7/2003 |
| WO | 2010/056722 | 5/2010 |
| WO | 2010/075204 | 7/2010 |
| WO | 2010/140339 | 12/2010 |
| WO | 2011/036885 | 3/2011 |
| WO | 2011/036889 | 3/2011 |
| WO | 2012/020848 | 2/2012 |
| WO | 2012/137982 | 10/2012 |

OTHER PUBLICATIONS

Desos, et al., "Enantioselective synthesis of a Pyrrolo-Benzothiadiazine Derivative S 18986, A New AMPA Receptor Positive Modulator", Bioorganic & Medicinal Chamistry Letters, 1996, vol. 6, No. 24, pp. 3003-3008.
Database Registry [Online] Chemical Abstracts Service, 2004— XP002661033.
L'abbé, et al., "Synthesis of Fused Dihydro-1,2,4-thiadiazolimines from Cyano-substituted Azides and Acyl Isothiocyanates", Journal of the Chemical Society, Perkin Transactions 1: Organic and Bio-Organic Chemistry, 1993, pp. 27-29.
Ward, et al., "Recent Advances in the Discovery of Selective AMPA Receptor Positive Allosteric Modulators", Current Medicinal Chemistry, vol. 17, No. 30, 2010, pp. 3503-3513.
Dingledine, et al., "The Glutamate Receptor Ion Channels", Pharmacological Reviews, vol. 51, No. 1, 1999, pp. 7-61.
Bettler, et al., "Review: Neurotransmitter Receptors II AMPA and Kainate Receptors", Neuropharmacology, vol. 34, 1995, pp. 123-139.

(Continued)

*Primary Examiner* — Kahsay Habte
(74) *Attorney, Agent, or Firm* — Hamre, Schumann, Mueller & Larson, P.C.

(57) ABSTRACT

Provided is a compound having an AMPA receptor function enhancing action, and useful as a prophylactic or therapeutic drug for depression, schizophrenia, Alzheimer's disease, attention deficit hyperactivity disorder (ADHD) and the like. The compound represented by formula (I):

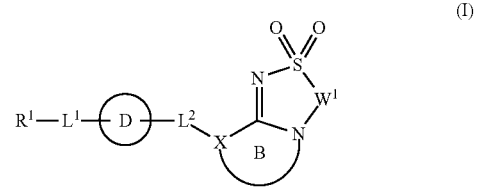

wherein each symbol is as defined in the DESCRIPTION, or a salt thereof has an AMPA receptor function enhancing action, and is useful as a prophylactic or therapeutic drug for depression, schizophrenia, Alzheimer's disease or attention deficit hyperactivity disorder (ADHD) and the like.

9 Claims, No Drawings

(56) References Cited

OTHER PUBLICATIONS

Malinow, et al., "AMPA Receptor Trafficking and Synaptic Plasticity", Ann. Rev. Neurosci., vol. 25, 2002, pp. 103-126.
Bowie, "Ionotropic Glutamate receptors & CNS Disorders", CNS & Neurological Disorders-Drug Targets, vol. 7, 2008, pp. 129-143.
Morrow, et al., "Recent advances in positive allosteric modulators of the AMPA receptor", Current Opinion in Drug Discovery & Development, vol. 9, 2006, pp. 571-579.
Supplemental European Search Report issued in European Application No. 13746897, Sep. 10, 2015, 2 pages.

HETEROCYCLIC COMPOUND AND USE THEREOF

TECHNICAL FIELD

The present invention relates to a heterocyclic compound, particularly a heterocyclic compound having an AMPA (α-amino-3-hydroxy-5-methyl-4-isoxazolepropionic acid) receptor function enhancing action.

BACKGROUND OF THE INVENTION

Glutamic acid is an excitatory neurotransmitter most abundantly present in the central nervous system of mammals. Glutamic acid plays an important role in the cognition, mood and control of motor function, and the neurotransmission thereof becomes unstable in mental diseases and neuropathy. Glutamic acid receptors are classified into ion ligand-gated ion channel and G protein conjugated-type receptor, and the ligand-gated ion channel is further classified into α-amino-3-hydroxy-5-methyl-4-isoxazolepropionic acid (AMPA) receptor, N-methyl-D-aspartic acid (NMDA) receptor and kainic acid (KA) receptor. (non-patent document 1)

AMPA receptor is one kind of receptor for excitatory neurotransmitter glutamic acid, and was named based on selective activation of the receptor by AMPA. AMPA receptor consists of 4 subunits (GluR1, GluR2, GluR3, GluR4). Each subunit contains flip type and flop type splicing variants. In the living body, AMPA receptor forms a homogeneous or heterogeneous tetramer consisting of such subunits. It has been reported that the physiological property of AMPA receptor varies depending on the subunits constituting the receptor. (non-patent documents 1, 2, 3)

The importance of AMPA receptor in brain physiology is well known, and a compound having an AMPA receptor function enhancing action is expected to be useful as a drug for the prophylaxis or treatment of mental diseases, neurodegenerative disease, memory disorders, sleep disorder and the like. (non-patent documents 4, 5)

As a heterocyclic compound, patent document 1 discloses disodium {4-(acetylamino)-8-[(3-{2-[4-(acetylamino)-2,2-dioxido-7-(sulfonatomethyl)-6H-pyrazolo[5,1-c][1,2,4]thiadiazin-8-yl]ethenyl}-5,5-dimethylcyclohex-2-en-1-yl)methylidene]-2,2-dioxido-8H-pyrazolo[5,1-c][1,2,4]thiadiazin-7-yl}methanesulfonate.

In addition, non-patent document 6 discloses 2,2,2-trichloro-N-(7,7-diphenyl-6,7-dihydro-5H-pyrrolo[2,1-c][1,2,4]thiadiazol-3-ylidene)acetamide.

DOCUMENT LIST

Patent Document patent document 1: JP-A-4-37742

Non-Patent Documents non-patent document 1: Pharmacological Reviews, Vol. 51, 7-61, 1999
non-patent document 2: Neuropharmacology, Vol. 34, 123-139, 1995
non-patent document 3: Ann. Rev. Neurosci., Vol. 25, 103-126, 2002
non-patent document 4: CNS & Neurological Disorders-Drug Targets, Vol. 7, 129-143, 2008
non-patent document 5: Current Opinion in Drug Discovery and Development, Vol. 9, 571-579, 2006
non-patent document 6: Journal of the Chemical Society, Perkin Transactions 1: Organic and Bio-Organic Chemistry (1993), (1), 27-29

SUMMARY OF THE INVENTION

Problems to be Solved by the Invention

The present invention aims to provide a heterocyclic compound having an AMPA receptor function enhancing action (AMPA receptor function enhancing agent (AMPA receptor potentiator); AMPA receptor function enhancing agent is sometimes also referred to as AMPA receptor positive modulator, AMPAkine, AMPA receptor allosteric modulator, AMPA receptor positive allosteric modulator or positive allosteric activator of AMPA receptor).

Means of Solving the Problems

The present inventors have found that a compound represented by the following formula (I) or a salt thereof (in the present specification, sometimes to be referred to as compound (I) or simply as the compound of the present invention) has an AMPA receptor function enhancing action, and conducted further studies, which resulted in the completion of the present invention. In this specification, compound (I) and a prodrug thereof are also sometimes collectively referred to as the compound of the present invention.

Accordingly, the present invention provides embodiments of the following respective items and the like.

[1] A compound represented by the formula (I)

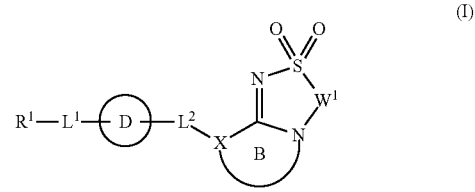

wherein
R$^1$ is an optionally substituted hydrocarbon group or an optionally substituted heterocyclic group;
L$^1$ is a bond, —O—, —CH$_2$—, —CH$_2$—O— or —O—CH$_2$—;
ring D is a further optionally substituted ring;
a partial structure:

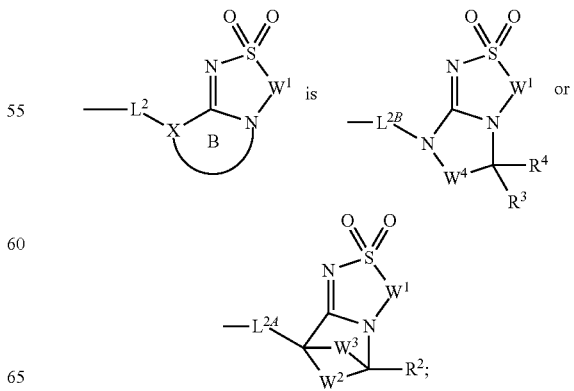

$L^{2A}$ is a bond, —O—, —CH$_2$—, —CH$_2$—O— or —O—CH$_2$—;
$L^{2B}$ is a bond, —O—, —CH$_2$— or —CH$_2$—O—;
$W^1$ is optionally substituted C$_{1-3}$ alkylene or optionally substituted C$_{2-3}$ alkenylene;
$W^2$, $W^3$ and $W^4$ are each independently optionally substituted C$_{1-3}$ alkylene; and
$R^2$, $R^3$ and $R^4$ are each independently a hydrogen atom or a substituent,
or a salt thereof;

[2] the compound of [1], wherein the partial structure:

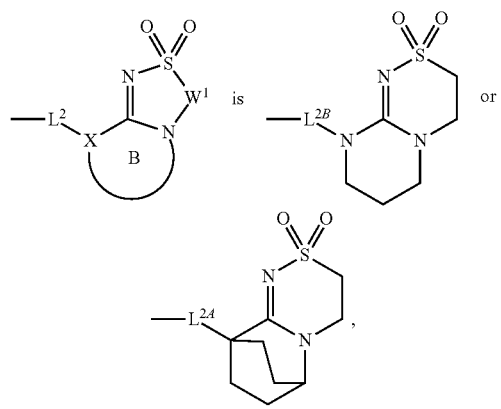

namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond or —O—CH$_2$—; and
$L^{2B}$ is a bond,
or a salt thereof;

[3] the compound of [1], wherein ring D is a benzene ring, or a m salt thereof;

[4] the compound of [1], wherein L$^1$ is a bond, —O— or —CH$_2$—O—, or a salt thereof;

[5] the compound of [1], wherein R$^1$ is
(1) C$_{1-6}$ alkyl optionally substituted by 1 to 3 substituents selected from a halogen atom and C$_{1-6}$ alkoxy;
(2) C$_{3-7}$ cycloalkyl;
(3) phenyl optionally substituted by 1 to 3 substituents selected from a halogen atom, cyano, C$_{1-6}$ alkyl optionally substituted by 1 to 3 halogen atoms and C$_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and C$_{1-6}$ alkyl optionally substituted by 1 to 3 halogen atoms;
(7) pyrimidinyl;
(8) isoxazolyl substituted by 1 to 3 C$_{1-6}$ alkyls;
(9) tetrahydrofuranyl; or
(10) pyrazolyl, or a salt thereof;

[6] the compound of [1], wherein R$^1$ is
(1) C$_{1-6}$ alkyl optionally substituted by 1 to 3 substituents selected from a halogen atom and C$_{1-6}$ alkoxy;
(2) C$_{3-7}$ cycloalkyl;
(3) phenyl optionally substituted by 1 to 3 substituents selected from a halogen atom, cyano, C$_{1-6}$ alkyl optionally substituted by 1 to 3 halogen atoms and C$_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and C$_{1-6}$ alkyl optionally substituted by 1 to 3 halogen atoms;
(7) pyrimidinyl;
(8) isoxazolyl substituted by 1 to 3 C$_{1-6}$ alkyls;
(9) tetrahydrofuranyl; or
(10) pyrazolyl;
L$^1$ is a bond, —O— or —CH$_2$—O—;
ring D is a benzene ring;
the partial structure:

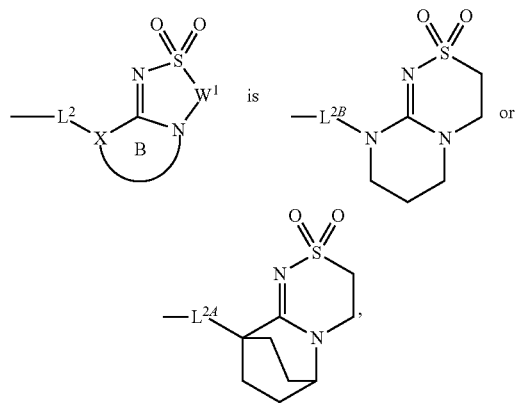

namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond or —O—CH$_2$—; or
$L^{2B}$ is a bond,
or a salt thereof;

[7] the compound of [1], wherein R$^1$ is
(1) C$_{1-6}$ alkyl;
(2) phenyl optionally substituted by 1 to 3 substituents selected from a halogen atom, cyano and C$_{1-6}$ alkyl optionally substituted by 1 to 3 halogen atoms;
(3) pyridyl substituted by 1 to 3 substituents selected from C$_{1-6}$ alkyl substituted by 1 to 3 halogen atoms;
(4) pyrimidinyl; or
(5) tetrahydrofuranyl;
L$^1$ is —O— or —CH$_2$—O—;
ring D is a benzene ring;
the partial structure:

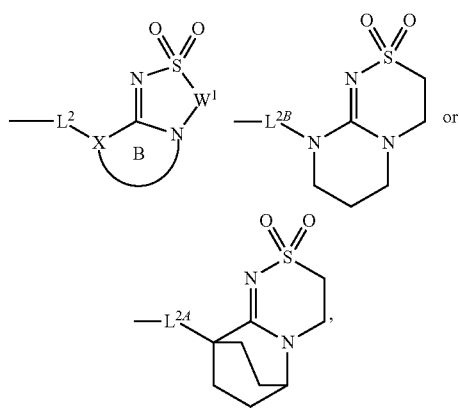

namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond; or
$L^{2B}$ is a bond,
or a salt thereof;

[8] 9-(4-(4-chlorophenoxy)phenyl)-3,4,6,7,8,9-hexahydro-6,9-ethanopyrido[2,1-c][1,2,4]thiadiazine 2,2-dioxide or a salt thereof;

[9] 9-(4-(4-chlorophenoxyl)phenyl)-3,4,6,7,8,9-hexahydropyrimido[2,1-c][1,2,4]thiadiazine 2,2-dioxide or a salt thereof;

[10] 9-(4-((6-(trifluoromethyl)pyridin-2-yl)oxy)phenyl)-3,4,6,7,8,9-hexahydro-6,9-ethanopyrido[2,1-c][1,2,4]thiadiazine 2,2-dioxide or a salt thereof;

[11] a medicament comprising the compound of [1] or a salt thereof;

[12] the medicament of [11], which is an AMPA receptor function enhancer;

[13] the medicament of [11], which is a prophylactic or therapeutic drug for depression, schizophrenia, Alzheimer's disease or attention deficit hyperactivity disorder;

[14] a method of preventing or treating depression, schizophrenia, Alzheimer's disease or attention deficit hyperactivity disorder in a mammal, comprising administering an effective amount of the compound of [1] or a salt thereof to the mammal;

[15] use of the compound of [1] or a salt thereof for the production of a prophylactic or therapeutic drug for depression, schizophrenia, Alzheimer's disease or attention deficit hyperactivity disorder;

[16] the compound of [1] or a salt thereof for use for the prophylaxis or treatment of depression, schizophrenia, Alzheimer's disease or attention deficit hyperactivity disorder;

[17] a method of enhancing AMPA receptor function of a mammal, comprising administering an effective amount of the compound of [1] or a salt thereof to the mammal.

The present invention also provides embodiments of the following respective items and the like.

[1A] A compound represented by the formula (I)

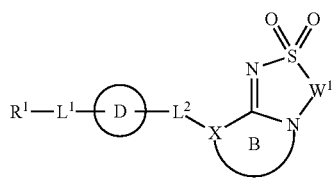

(I)

wherein $R^1$ is an optionally substituted hydrocarbon group or an optionally substituted heterocyclic group;

$L^1$ is a bond, —O—, —CH$_2$—, —CH$_2$—O— or —O—CH$_2$—;

ring D is a further optionally substituted ring;

a partial structure:

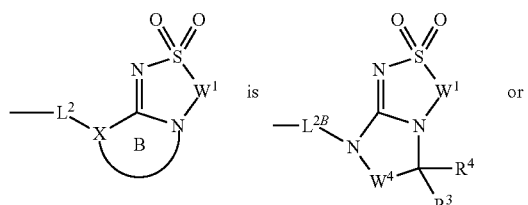

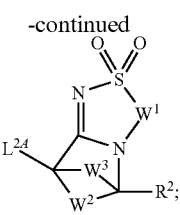

$L^{2A}$ is a bond, —O—, —CH$_2$—, —CH$_2$—O— or —O—CH$_2$—;

$L^{2B}$ is a bond, —O—, —CH$_2$— or —CH$_2$—O—;

$W^1$ is optionally substituted C$_{1-3}$ alkylene or optionally substituted C$_{2-3}$ alkenylene;

$W^2$, $W^3$ and $W^4$ are each independently optionally substituted C$_{1-3}$ alkylene;

$R^2$, $R^3$ and $R^4$ are each independently a hydrogen atom or a substituent, or a salt thereof;

[2A] a medicament comprising the compound of [1A], or a salt thereof;

[3A] the medicament of [2A], which is an AMPA receptor function enhancer;

[4A] the medicament of [2A], which is a prophylactic or therapeutic drug for depression, schizophrenia, Alzheimer's disease or attention deficit hyperactivity disorder;

The present invention also provides embodiments of the following respective items and the like.

[5A] a method of preventing or treating depression, schizophrenia, Alzheimer's disease or attention deficit hyperactivity disorder in a mammal, comprising administering an effective amount of compound (I) or compound (I-A)-(I-R) or a salt thereof to the mammal;

[6A] use of compound (I) or compound (I-A)-(I-R) or a salt thereof for the production of a prophylactic or therapeutic drug for depression, schizophrenia, Alzheimer's disease or attention deficit hyperactivity disorder;

[7A] compound (I) or compound (I-A)-(I-R) or a salt thereof for use for the prophylaxis or treatment of depression, schizophrenia, Alzheimer's disease or attention deficit hyperactivity disorder.

Effect of the Invention

According to the present invention, a compound having an AMPA receptor function enhancing action, which is useful as a prophylactic or therapeutic drug for depression, schizophrenia, Alzheimer's disease, attention deficit hyperactivity disorder (ADHD) and the like can be provided.

DETAILED DESCRIPTION OF THE INVENTION

The present invention is explained in detail in the following.

In the present specification, indication of hydrogen atom in the chemical structural formulas may be sometimes omitted according to the conventional practice in the chemical field.

In the present specification, unless otherwise specified, the "halogen atom" is, for example, fluorine, chlorine, bromine or iodine.

In the present specification, unless otherwise specified, "optionally halogenated" or "halogeno" means optionally having one or more (e.g., 1-3) halogen atoms as substituent(s).

In the present specification, unless otherwise specified, examples of the "hydrocarbon group" include non-cyclic hydrocarbon group, aromatic hydrocarbon group, and nonaromatic hydrocarbon group.

In the present specification, unless otherwise specified, the "non-cyclic hydrocarbon group" is, for example, alkyl, alkenyl or alkynyl.

In the present specification, unless otherwise specified, the "nonaromatic hydrocarbon ring" is, for example, a nonaromatic hydrocarbon ring having a carbon number of 3-8 such as $C_{3-8}$ cycloalkane, $C_{5-8}$ cycloalkene, $C_{5-8}$ cycloalkadiene, bridged ring hydrocarbon having a carbon number of 5-8 or the like.

In the present specification, unless otherwise specified, the "$C_{3-8}$ cycloalkane" is, for example, cyclopropane, cyclobutane, cyclopentane, cyclohexane, cycloheptane or cyclooctane.

In the present specification, unless otherwise specified, the "$C_{5-8}$ cycloalkene" is, for example, cyclopentene, cyclohexene, cycloheptene or cyclooctene.

In the present specification, unless otherwise specified, the "$C_{5-8}$ cycloalkadiene" is, for example, cyclopentadiene, cyclohexadiene, cycloheptadiene or cyclooctadiene.

In the present specification, unless otherwise specified, the "bridged ring hydrocarbon having a carbon number of 5-8" is, for example, bicyclo[2.1.0]pentane, bicyclo[2.2.1]heptane, bicyclo[3.2.1]octane, bicyclo[2.2.1]hept-2-ene or tricyclo[2.2.1.0]heptane.

In the present specification, unless otherwise specified, the "aromatic hydrocarbon ring" is, for example, an aromatic hydrocarbon ring having a carbon number of 6-14 (6-14-membered), as concrete examples thereof include benzene ring, naphthalene ring, anthracene ring, and phenanthrene ring. In the present specification, unless otherwise specified, the "6-10-membered aromatic hydrocarbon ring" is, for example, 6- to 10-membered aromatic hydrocarbon ring from among the above-mentioned "6- to 14-membered aromatic hydrocarbon ring".

In the present specification, unless otherwise specified, the "aromatic hydrocarbon ring" may be monocyclic, bicyclic or tricyclic.

In the present specification, unless otherwise specified, the "heterocycle" is, for example, a 3- to 14-membered heterocycle containing 1-4 hetero atoms selected from a nitrogen atom (N), a sulfur atom (S) and an oxygen atom (O).

In the present specification, unless otherwise specified, the "heterocycle" is, for example, non-aromatic heterocycle or aromatic heterocycle.

In the present specification, unless otherwise specified, the "non-aromatic heterocycle" is, for example, monocyclic non-aromatic heterocycle or fused non-aromatic heterocycle.

In the present specification, unless otherwise specified, the "monocyclic non-aromatic heterocycle" is, for example, 3-8-membered non-aromatic heterocycle such as an oxirane ring, an azetidine ring, an oxetane ring, a thietane ring, a pyrrolidine ring, a dihydrofuran ring, a tetrahydrofuran ring, a tetrahydrothiophene ring, an imidazolidine ring, an oxazolidine ring, an isooxazoline ring, a piperidine ring, a dihydropyran ring, a tetrahydropyran ring, a tetrahydrothiopyran ring, a morpholine ring, a thiomorpholine ring, a piperazine ring, a dihydrooxazine ring, a tetrahydrooxazine ring, a dihydropyrimidine ring, a tetrahydropyrimidine ring, an azepane ring, an oxepane ring, a thiepane ring, an oxazepane ring, a thiazepane ring, an azocane ring, an oxocane ring, a thiocane ring, an oxazocane ring, a thiazocane ring and the like.

In the present specification, unless otherwise specified, the "fused non-aromatic heterocycle" is, for example, monocyclic non-aromatic heterocycle fused with one or two rings selected from a nonaromatic hydrocarbon ring having a carbon number of 3-8, a benzene ring, a monocyclic non-aromatic heterocycle and a 5- or 6-membered aromatic heterocycle. Specific examples thereof include bicyclic fused non-aromatic heterocycle such as dihydroindole, dihydroisoindole, dihydrobenzofuran, dihydrobenzodioxine, dihydrobenzodioxepine, tetrahydrobenzofuran, chromene, dihydroquinoline, tetrahydroquinoline, dihydroisoquinoline, tetrahydroisoquinoline, dihydrophthalazine, tetrahydrobenzoazepine and the like.

In the present specification, unless otherwise specified, the "aromatic heterocycle" is, for example, monocyclic aromatic heterocycle or fused aromatic heterocycle.

In the present specification, unless otherwise specified, the "monocyclic aromatic heterocycle" is, for example, 5- or 6-membered aromatic heterocycle such as a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring and the like. In the present specification, unless otherwise specified, the "6-membered aromatic heterocycle" is 6-membered aromatic heterocycle from among the above-mentioned "5- or 6-membered aromatic heterocycle".

In the present specification, unless otherwise specified, the "fused aromatic heterocycle" is, for example, monocyclic aromatic heterocycle fused with 1 or 2 rings selected from a benzene ring and 5- or 6-membered aromatic heterocycle. Specific examples thereof include bicyclic fused aromatic heterocycle such as quinoline, isoquinoline, quinazoline, quinoxaline, benzofuran, benzothiophene, benzoxazole, benzisoxazole, benzothiazole, benzimidazole, benzotriazole, indole, indolizine, indazole, pyrrolopyrazine (e.g., 1H-pyrrolo[2,3-b]pyrazine, 1H-pyrrolo[2,3-b]pyrazine, pyrrolo[1,2-a]pyrazine), pyrazolopyridine (e.g., pyrazolo[1,5-a]pyridine), imidazopyridine (e.g., 1H-imidazo[4,5-b]pyridine, 1H-imidazo[4,5-c]pyridine, 2H-imidazo[1,2-a]pyridine, imidazo[1,2-a]pyridine, imidazo[1,5-a]pyridine), triazolopyridine (e.g., 1H-[1,2,3]triazolo[4,5-b]pyridine, 1H-[1,2,3]triazolo[4,5-c]pyridine, [1,2,4]triazolo[4,3-a]pyridine, [1,2,4]triazolo[1,5-a]pyridine), imidazopyrazine (e.g., 1H-imidazo[4,5-b]pyrazine, imidazo[1,2-a]pyrazine, imidazo[1,5-a]pyrazine), triazolopyrazine (e.g., [1,2,4]triazolo[1,5-a]pyrazine), pyrazolopyridine (e.g., 1H-pyrazolo[4,3-c]pyridine), pyrazolothiophene (e.g., 2H-pyrazolo[3,4-b]thiophene), pyrazolotriazine (e.g., pyrazolo[5,1-c][1,2,4]triazine) and the like.

In the present specification, unless otherwise specified, the "nitrogen-containing heterocycle" is a heterocycle containing a nitrogen atom from among the above-mentioned "heterocycle".

Unless otherwise specified, in this specification, examples of the "alkyl (group)" include $C_{1-6}$ alkyl (group).

In the present specification, unless otherwise specified, the "$C_{1-6}$ alkyl group" is, for example, methyl, ethyl, n-propyl, isopropyl, n-butyl, isobutyl, sec-butyl, tert-butyl, pentyl, isopentyl, neopentyl or hexyl.

Unless otherwise specified, in this specification, "optionally halogenated $C_{1-6}$ alkyl (group)" means $C_{1-6}$ alkyl (group) which may be substituted by halogen atom (s), and examples thereof include trifluoromethyl.

In the present specification, unless otherwise specified, the "alkenyl (group)" is, for example, $C_{2-6}$ alkenyl (group).

In the present specification, unless otherwise specified, the "$C_{2-6}$ alkenyl (group)" is, for example, vinyl, 1-propen-1-yl, 2-propen-1-yl, isopropenyl, 2-buten-1-yl, 4-penten-1-yl or 5-hexen-1-yl.

In the present specification, unless otherwise specified, the "alkynyl (group)" is, for example, a $C_{2-6}$ alkynyl group. Examples of the "$C_{2-6}$ alkynyl (group)" include ethynyl, 1-propyn-1-yl, 2-propyn-1-yl, 4-pentyn-1-yl and 5-hexyn-1-yl.

In the present specification, unless otherwise specified, the "$C_{3-7}$ cycloalkyl-$C_{2-6}$ alkynyl (group)" is, for example, cyclopropylethynyl.

In the present specification, unless otherwise specified, the "nonaromatic cyclic hydrocarbon group" is, for example, $C_{3-7}$ cycloalkyl (group), $C_{3-7}$ cycloalkenyl (group), or $C_{4-10}$ cycloalkadienyl (group), each of which is optionally fused with one or more (preferably 1 or 2) hydrocarbon rings.

Examples of the "hydrocarbon ring" include the aforementioned "nonaromatic hydrocarbon ring" and the aforementioned "aromatic hydrocarbon ring".

In the present specification, unless otherwise specified, the "$C_{3-7}$ cycloalkyl (group)" is, for example, cyclopropyl, cyclobutyl, cyclopentyl, cyclohexyl or cycloheptyl.

In the present specification, unless otherwise specified, the "$C_{3-7}$ cycloalkenyl (group)" is, for example, cyclopropenyl, cyclobutenyl, cyclopentenyl, cyclohexenyl or cycloheptenyl.

In the present specification, unless otherwise specified, the "$C_{4-10}$ cycloalkadienyl (group)" is, for example, cyclobutadienyl, cyclopentadienyl, cyclohexadienyl, cycloheptadienyl, cyclooctadienyl, cyclononadienyl or cyclodecadienyl.

In the present specification, unless otherwise specified, the "aromatic cyclic hydrocarbon group" may be monocyclic, bicyclic or tricyclic.

In the present specification, unless otherwise specified, the "aromatic cyclic hydrocarbon group" is, for example, $C_{6-14}$ aryl (group) or the like. Specific examples thereof include phenyl, 1-naphthyl, 2-naphthyl, 2-biphenylyl, 3-biphenylyl, 4-biphenylyl and 2-anthryl.

In the present specification, unless otherwise specified, the "$C_{7-16}$ aralkyl (group)" is, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl or 4-biphenylylmethyl.

In the present specification, unless otherwise specified, the "$C_{6-14}$ aryl-$C_{2-6}$ alkenyl (group)" is, for example, styryl.

In the present specification, unless otherwise specified, the "$C_{1-7}$ alkylene (group)" (that is, $C_{1-6}$ alkanediyl group) is, for example, methylene, ethylene, trimethylene, tetramethylene, 2-butenylene, 2-methyltetramethylene, pentamethylene or hexamethylene.

In the present specification, unless otherwise specified, the "$C_{2-7}$ alkylene (group)" is, for example, alkylene (group) having a carbon number of 2-7 from the aforementioned "$C_{1-7}$ alkylene (group)". Examples of the "$C_{1-3}$ alkylene (group)" include alkylene (group) having a carbon number of 1-3 from the aforementioned "$C_{1-7}$ alkylene (group)".

In the present specification, unless otherwise specified, the "$C_{2-6}$ alkenylene (group)" is, for example, —CH=CH—, —CH=C(CH$_3$)—, —C(CH$_3$)=CH—, —CH=CH—CH$_2$—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$— or —CH=C(C$_2$H$_5$)—.

In the present specification, unless otherwise specified, the "$C_{2-3}$ alkenylene (group)" is, for example, alkenylene (group) having a carbon number of 2 or 3 from the aforementioned "$C_{2-6}$ alkenylene (group)".

In the present specification, unless otherwise specified, the "$C_{2-6}$ alkynylene (group)" is, for example, —CH$_2$—C≡C—, —CH$_2$—C≡C—CH(CH$_3$)— or —CH$_2$—C≡C—CH$_2$—CH$_2$—.

In the present specification, unless otherwise specified, the "heterocyclic group" (and heterocyclic moiety in substituent) is, for example, a nonaromatic heterocyclic group or an aromatic heterocyclic group (that is, a heteroaryl group).

In the present specification, unless otherwise specified, the "heterocyclic group" may be monocyclic, bicyclic or tricyclic.

In the present specification, unless otherwise specified, the "heterocyclic group" is, for example, a 3- to 14-membered heterocyclic group containing 1 to 4 hetero atoms selected from an oxygen atom, a sulfur atom and a nitrogen atom, and the like.

In the present specification, unless otherwise specified, the "nonaromatic heterocyclic group" may be saturated or unsaturated.

In the present specification, unless otherwise specified, the "nonaromatic heterocyclic group" is, for example, a 3- to 14-membered nonaromatic heterocyclic group.

In the present specification, unless otherwise specified, examples of the "3- to 14-membered nonaromatic heterocyclic group" is, for example, a 3- to 8-membered nonaromatic heterocyclic group containing 1 to 4 hetero atoms selected from an oxygen atom, a sulfur atom and a nitrogen atom, which may be fused with a 5- or 6-membered ring.

In the present specification, unless otherwise specified, the "3- to 8-membered nonaromatic heterocyclic group containing 1 to 4 hetero atoms selected from an oxygen atom, a sulfur atom and a nitrogen atom" is, for example, tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl or 2,3-dihydro-1H-imidazo[1,2-a]imidazol-1-yl.

In the present specification, unless otherwise specified, the "5- or 6-membered ring" is, for example, a hydrocarbon ring having a carbon number of 5 or 6 (e.g., cyclopentane, cyclohexane, cyclopentene, cyclohexene, cyclopentadiene, cyclohexadiene, benzene) or 5- or 6-membered heterocycle.

In the present specification, unless otherwise specified, the "5- or 6-membered heterocycle" is, for example, the aforementioned "heterocycle" which is 5- or 6-membered.

In the present specification, unless otherwise specified, the "3- to 6-membered nonaromatic heterocyclic group containing 1 to 4 hetero atoms selected from an oxygen atom, a sulfur atom and a nitrogen atom, which is fused with a 5- or 6-membered ring" is, for example, 2,3-dihydro-1H-imidazo[1,2-a]benzimidazol-1-yl.

In the present specification, unless otherwise specified, the "aromatic heterocyclic group" is, for example, a 5- or 6-membered monocyclic aromatic heterocyclic group or a 5- to 10-membered aromatic fused heterocyclic group.

In the present specification, unless otherwise specified, the "5- or 6-membered monocyclic aromatic heterocyclic group" is, for example, a 5- or 6-membered monocyclic aromatic heterocyclic group containing 1 to 4 hetero atoms selected from an oxygen atom, a sulfur atom and a nitrogen atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl and the like.

In the present specification, unless otherwise specified, the "5- to 10-membered aromatic fused heterocyclic group" is, for example, a 5- to 10-membered aromatic fused heterocyclic group containing 1 to 4 hetero atoms selected from an oxygen atom, a sulfur atom and a nitrogen atom, such as isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl, (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzoisoxazol-3-yl, 1,2-benzoisoxazol-4-yl, 1,2-benzoisoxazol-5-yl, 1,2-benzoisoxazol-6-yl, 1,2-benzoisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzoisothiazol-3-yl, 1,2-benzoisothiazol-4-yl, 1,2-benzoisothiazol-5-yl, 1,2-benzoisothiazol-6-yl, 1,2-benzoisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like.

Unless otherwise specified, in this specification, examples of the "alkoxy (group)" include $C_{1-6}$ alkoxy (group).

Unless otherwise specified, in this specification, examples of the "$C_{1-6}$ alkoxy (group)" include methoxy, ethoxy, propoxy, isopropoxy, butoxy, isobutoxy, sec-butoxy, pentyloxy and hexyloxy.

In the present specification, unless otherwise specified, the "$C_{3-7}$ cycloalkyloxy (group)" is, for example, cyclopropyloxy, cyclobutyloxy, cyclopentyloxy or cyclohexyloxy.

In the present specification, unless otherwise specified, the "$C_{6-14}$ aryloxy (group)" is, for example, phenyloxy, 1-naphthyloxy or 2-naphthyloxy.

In the present specification, unless otherwise specified, the "$C_{7-15}$ aralkyloxy (group)" is, for example, benzyloxy or phenethyloxy.

In the present specification, unless otherwise specified, the "alkyl-carbonyloxy (group)" is, for example, alkyl-carbonyloxy (group).

In the present specification, unless otherwise specified, the "$C_{1-6}$ alkyl-carbonyloxy (group)" is, for example, acetoxy or propionyloxy.

In the present specification, unless otherwise specified, the "alkoxy-carbonyloxy (group)" is, for example, $C_{1-6}$ alkoxy-carbonyloxy (group).

In the present specification, unless otherwise specified, the "$C_{1-6}$ alkoxy-carbonyloxy (group)" is, for example, methoxycarbonyloxy, ethoxycarbonyloxy, propoxycarbonyloxy or butoxycarbonyloxy.

In the present specification, unless otherwise specified, the "mono-alkyl-carbamoyloxy (group)" is, for example, mono-$C_{1-6}$ alkyl-carbamoyloxy (group).

In the present specification, unless otherwise specified, the "mono-$C_{1-5}$ alkyl-carbamoyloxy (group)" is, for example, methylcarbamoyloxy or ethylcarbamoyloxy.

In the present specification, unless otherwise specified, the "di-alkyl-carbamoyloxy (group)" is, for example, di-$C_{1-6}$ alkyl-carbamoyloxy (group).

In the present specification, unless otherwise specified, the "di-$C_{1-6}$ alkyl-carbamoyloxy (group)" is, for example, dimethylcarbamoyloxy or diethylcarbamoyloxy.

In the present specification, unless otherwise specified, the "$C_{6-14}$ aryl-carbonyloxy (group)" is, for example, benzoyloxy or naphthylcarbonyloxy.

In the present specification, unless otherwise specified, the "mono- or di-$C_{6-14}$ aryl-carbamoyloxy (group)" is, for example, phenylcarbamoyloxy or naphthylcarbamoyloxy.

In the present specification, unless otherwise specified, the heterocyclic moiety of the "heterocyclyl-oxy (group)" is, for example, one similar to the aforementioned "heterocyclic group". Specific examples of the "heterocyclyl-oxy (group)" include a 3- to 14-membered heterocyclyl-oxy (group) containing 1 to 5 hetero atoms selected from a nitrogen atom, a sulfur atom and an oxygen atom.

In the present specification, unless otherwise specified, the aromatic heterocyclic moiety of the "aromatic heterocyclyl-oxy (group)" is, for example, one similar to the "aromatic heterocyclic group" exemplified as the aforementioned "heterocyclic group". Specific examples of the "aromatic heterocyclyl-oxy (group)" include a 5- to 14-membered aromatic heterocyclyl-oxy containing 1 to 5 hetero atoms selected from a nitrogen atom, a sulfur atom and an oxygen atom.

In the present specification, unless otherwise specified, the "$C_{1-6}$ alkylsulfonyloxy group" is, for example, methylsulfonyloxy or ethylsulfonyloxy.

In the present specification, unless otherwise specified, the "halogeno $C_{1-6}$ alkylsulfonyloxy group" is, for example, halogenomethylsulfonyloxy or halogenoethylsulfonyloxy.

In the present specification, unless otherwise specified, the "alkylsulfanyl (group)" is, for example, $C_{1-6}$ alkylsulfanyl (group).

In the present specification, unless otherwise specified, the "$C_{1-6}$ alkylsulfanyl (group)" is, for example, methylsulfanyl, ethylsulfanyl, propylsulfanyl, isopropylsulfanyl, butylsulfanyl, sec-butylsulfanyl or tert-butylsulfanyl.

In the present specification, unless otherwise specified, the "$C_{3-7}$ cycloalkylsulfanyl (group)" is, for example, cyclopropylsulfanyl, cyclobutylsulfanyl, Cyclopentylsulfanyl or cyclohexylsulfanyl.

In the present specification, unless otherwise specified, the "$C_{6-14}$ arylsulfanyl (group)" is, for example, phenylsulfanyl, 1-naphthylsulfanyl or 2-naphthylsulfanyl.

In the present specification, unless otherwise specified, the "$C_{7-16}$ aralkylsulfanyl (group)" is, for example, benzylsulfanyl or phenethylsulfanyl.

In the present specification, unless otherwise specified, the heterocyclic moiety of the "heterocyclyl-sulfanyl (group)" is, for example, one similar to the aforementioned "heterocyclic group". Specific examples of the "heterocyclyl-sulfanyl (group)" include 3- to 14-membered heterocyclyl-sulfanyl (group) containing 1 to 5 hetero atoms selected from a nitrogen atom, a sulfur atom and an oxygen atom.

In the present specification, unless otherwise specified, the "alkyl-carbonyl (group)" is, for example, $C_{1-6}$ alkyl-carbonyl.

In the present specification, unless otherwise specified, the "$C_{1-6}$ alkyl-carbonyl (group)" is, for example, acetyl, propionyl or pivaloyl.

In the present specification, unless otherwise specified, the "$C_{3-7}$ cycloalkyl-carbonyl (group)" is, for example, cyclopropylcarbonyl, cyclopentylcarbonyl or cyclohexylcarbonyl.

In the present specification, unless otherwise specified, the "$C_{6-14}$ aryl-carbonyl (group)" is, for example, benzoyl, 1-naphthoyl or 2-naphthoyl.

In the present specification, unless otherwise specified, the "$C_{7-16}$ aralkyl-carbonyl (group)" is, for example, phenylacetyl or 3-phenylpropionyl.

In the present specification, unless otherwise specified, the heterocyclic moiety of the "heterocyclyl-carbonyl (group)" is, for example, one similar to the aforementioned "heterocyclic group". Specific examples thereof include 3- to 14-membered heterocyclyl-carbonyl (group) containing 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

In the present specification, unless otherwise specified, the "optionally esterified carboxy (group)" is, for example, carboxy, optionally substituted alkoxy-carbonyl, optionally substituted $C_{6-14}$ aryloxy-carbonyl, optionally substituted $C_{7-16}$ aralkyloxy-carbonyl, optionally substituted silyloxy-carbonyl (e.g., TMS-O—CO—, TES-O—CO—, TBS-O—CO—, TIPS-O—CO—, TBDPS-O—CO—) and the like.

In the present specification, unless otherwise specified, the "alkoxy-carbonyl (group)" is, for example, "$C_{1-6}$ alkoxy-carbonyl (group)".

In the present specification, unless otherwise specified, the "$C_{1-6}$ alkoxy-carbonyl (group)" is, for example, methoxycarbonyl, ethoxycarbonyl, propoxycarbonyl or tert-butoxycarbonyl.

In the present specification, unless otherwise specified, the "$C_{5-14}$ aryloxy-carbonyl (group)" is, for example, phenoxycarbonyl.

In the present specification, unless otherwise specified, the "$C_{7-16}$ aralkyloxy-carbonyl (group)" is, for example, benzyloxycarbonyl or phenethyloxycarbonyl.

In the present specification, unless otherwise specified, the "alkylsulfonyl (group)" is, for example, $C_{1-6}$ alkylsulfonyl (group).

In the present specification, unless otherwise specified, the "$C_{1-6}$ alkylsulfonyl (group)" is, for example, methylsulfonyl or ethylsulfonyl.

In the present specification, unless otherwise specified, the "$C_{3-7}$ cycloalkylsulfonyl (group)" is, for example, cyclopropylsulfonyl, cyclobutylsulfonyl, cyclopentylsulfonyl or cyclohexylsulfonyl.

In the present specification, unless otherwise specified, the "$C_{6-14}$ arylsulfonyl (group)" is, for example, phenylsulfonyl, 1-naphthylsulfonyl or 2-naphthylsulfonyl.

In the present specification, unless otherwise specified, the heterocyclic moiety of the "heterocyclyl-sulfonyl (group)" is, for example, one similar to the aforementioned "heterocyclic group". Specific examples of the "heterocyclyl-sulfonyl (group)" include 3- to 14-membered heterocyclyl-sulfonyl (group) containing 1 to 5 hetero atoms selected from a nitrogen atom, a sulfur atom and an oxygen atom.

In the present specification, unless otherwise specified, the "alkylsulfinyl (group)" is, for example, $C_{1-5}$ alkylsulfinyl (group).

In the present specification, unless otherwise specified, the "$C_{1-5}$ alkylsulfinyl (group)" is, for example, methylsulfinyl or ethylsulfinyl.

In the present specification, unless otherwise specified, the "$C_{3-7}$ cycloalkylsulfinyl (group)" is, for example, cyclopropylsulfinyl, cyclobutylsulfinyl, cyclopentylsulfinyl or cyclohexylsulfinyl.

In the present specification, unless otherwise specified, the "$C_{5-14}$ arylsulfinyl (group)" is, for example, phenylsulfinyl, 1-naphthylsulfinyl or 2-naphthylsulfinyl.

In the present specification, unless otherwise specified, the heterocyclic moiety of the "heterocyclyl-sulfinyl (group)" is, for example, one similar to the aforementioned "heterocyclic group". Specific examples of the "heterocyclyl-sulfinyl (group)" include 3- to 14-membered heterocyclyl-sulfinyl (group) containing 1 to 5 hetero atoms selected from a nitrogen atom, a sulfur atom and an oxygen atom.

In the present specification, unless otherwise specified, the "alkyl-carbamoyl (group)" is, for example, mono- or di-$C_{1-6}$ alkyl-carbamoyl (group).

In the present specification, unless otherwise specified, the "mono- or di-$C_{1-5}$ alkyl-carbamoyl (group)" is, for example, methylcarbamoyl, dimethylcarbamoyl, ethylcarbamoyl or propylcarbamoyl.

In the present specification, unless otherwise specified, the "mono- or di-alkylamino (group)" is, for example, mono- or alkylamino (group).

In the present specification, unless otherwise specified, the "mono- or di-$C_{1-5}$ alkylamino (group)" is, for example, methylamino, ethylamino, propylamino, dimethylamino or diethylamino.

In the present specification, unless otherwise specified, the "alkyl-carbonylamino (group)" is, for example, $C_{1-6}$ alkyl-carbonylamino.

In the present specification, unless otherwise specified, the "$C_{1-6}$ alkyl-carbonylamino (group)" is, for example, acetylamino, propionylamino or pivaloylamino.

In the present specification, unless otherwise specified, the "heterocycle (group)" of the "heterocyclyl-amino (group)" is, for example, one similar to the aforementioned "heterocyclic group". Example of the "heterocyclyl-amino (group)" include 2-pyridyl-amino.

In the present specification, unless otherwise specified, the "heterocyclyl-carbonyl" of the "heterocyclyl-carbonylamino (group)" is, for example, one similar to the aforementioned "heterocyclyl-carbonyl". Examples of the "heterocyclyl-carbonylamino (group)" include pyridyl-carbonylamino.

In the present specification, unless otherwise specified, the "heterocycle (group)" of the "heterocyclyl-oxycarbonylamino (group)" is, for example, one similar to the aforementioned "heterocyclic group". Examples of the "heterocyclyl-oxycarbonylamino (group)" include 2-pyridyl-oxycarbonylamino.

In the present specification, unless otherwise specified, the "heterocycle (group)" of the "heterocyclyl-sulfonylamino (group)" is, for example, one similar to the aforementioned "heterocyclic group". Examples of the "heterocyclyl-sulfonylamino (group)" include 2-pyridyl-sulfonylamino.

In the present specification, unless otherwise specified, the "alkoxy-carbonylamino (group)" is, for example, $C_{1-6}$ alkoxy-carbonylamino (group).

In the present specification, unless otherwise specified, the "$C_{1-6}$ alkoxy-carbonylamino (group)" is, for example, methoxycarbonylamino, ethoxycarbonylamino, propoxycarbonylamino or butoxycarbonylamino.

In the present specification, unless otherwise specified, the "alkylsulfonylamino (group)" is, for example, $C_{1-6}$ alkyl-sulfonylamino (group).

In the present specification, unless otherwise specified, the "$C_{1-6}$ alkylsulfonylamino (group)" is, for example, methylsulfonylamino or ethylsulfonylamino.

In the present specification, unless otherwise specified, the "mono- or di-$C_{3-7}$ cycloalkylamino (group)" is, for example, cyclopropylamino, cyclopentylamino or cyclohexylamino.

In the present specification, unless otherwise specified, the "$C_{3-7}$ cycloalkyl-carbonylamino (group)" is, for example, cyclopropylcarbonylamino, cyclopentylcarbonylamino or cyclohexylcarbonylamino.

In the present specification, unless otherwise specified, the "$C_{3-7}$ cycloalkyloxy-carbonylamino (group)" is, for example, cyclopropoxycarbonylamino, cyclopentyloxycarbonylamino or cyclohexyloxycarbonylamino.

In the present specification, unless otherwise specified, the "$C_{3-7}$ cycloalkylsulfonylamino (group)" is, for example, cyclopropylsulfonylamino, cyclopentylsulfonylamino or cyclohexylsulfonylamino.

In the present specification, unless otherwise specified, the "mono- or di-$C_{6-14}$ arylamino (group)" is, for example, phenylamino or diphenylamino.

In the present specification, unless otherwise specified, the "mono- or di-$C_{7-16}$ aralkylamino (group)" is, for example, benzylamino.

In the present specification, unless otherwise specified, the "$C_{6-14}$ aryl-carbonylamino (group)" is, for example, benzoylamino or naphthoylamino.

In the present specification, unless otherwise specified, the "$C_{6-14}$ arylsulfonylamino (group)" is, for example, phenylsulfonylamino, 2-naphthylsulfonylamino or 1-naphthylsulfonylamino.

In the present specification, unless otherwise specified, being "optionally substituted" means being optionally substituted by 1-5 (preferably 1-3, more preferably 1 or 2) substituents selected from the following substituent group A, at substitutable position(s). When the number of the substituents is two or more, the respective substituents may be the same or different.

The substituent groups of the compounds of the present specification are explained below.
[Substituent Group A]

In the present specification, substituent group A includes substituents of the following (1)-(52).
(1) a halogen atom
(2) a nitro group
(3) a cyano group
(4) an optionally esterified carboxy group
(5) an optionally substituted alkyl group
(6) an optionally substituted alkenyl group
(7) an optionally substituted alkynyl group (e.g., an optionally substituted $C_{3-7}$ cycloalkyl-$C_{2-6}$ alkynyl group)
(8) an optionally substituted $C_{3-7}$ cycloalkyl group
(9) an optionally substituted $C_{6-14}$ aryl group
(10) an optionally substituted $C_{7-15}$ aralkyl group
(11) an optionally substituted $C_{6-14}$ aryl-$C_{2-6}$ alkenyl group
(12) an optionally substituted heterocyclic group
(13) a hydroxy group
(14) an optionally substituted alkoxy group
(15) an optionally substituted $C_{3-7}$ cycloalkyloxy group
(16) an optionally substituted $C_{6-14}$ aryloxy group
(17) an optionally substituted $C_{7-16}$ aralkyloxy group
(18) an optionally substituted alkyl-carbonyloxy group
(19) an optionally substituted alkoxy-carbonyloxy group
(20) an optionally substituted mono-alkyl-carbamoyloxy group
(21) an optionally substituted di-alkyl-carbamoyloxy group
(22) an optionally substituted $C_{6-14}$ aryl-carbonyloxy group
(23) an optionally substituted mono- or di-$C_{6-14}$ aryl-carbamoyloxy group
(24) an optionally substituted heterocyclyl-oxy group (e.g., an optionally substituted aromatic heterocyclyl-oxy group)
(25) an optionally substituted $C_{1-6}$ alkylsulfonyloxy group (e.g., an optionally substituted halogeno $C_{1-6}$ alkylsulfonyloxy group)
(26) a sulfanyl (mercapto) group
(27) an optionally substituted alkylsulfanyl group
(28) an optionally substituted $C_{3-7}$ cycloalkylsulfanyl group

(29) an optionally substituted $C_{6-14}$ arylsulfanyl group
(30) an optionally substituted $C_{7-16}$ aralkylsulfanyl group
(31) an optionally substituted heterocyclyl-sulfanyl group
(32) a formyl group
(33) an optionally substituted alkyl-carbonyl group
(34) an optionally substituted $C_{3-7}$ cycloalkyl-carbonyl group
(35) an optionally substituted $C_{6-14}$ aryl-carbonyl group
(36) an optionally substituted $C_{7-16}$ aralkyl-carbonyl group
(37) an optionally substituted heterocyclyl-carbonyl group
(38) an optionally substituted alkylsulfonyl group
(39) an optionally substituted $C_{3-7}$ cycloalkylsulfonyl group
(40) an optionally substituted $C_{6-14}$ arylsulfonyl group
(41) an optionally substituted heterocyclyl-sulfonyl group
(42) an optionally substituted alkylsulfinyl group
(43) an optionally substituted $C_{3-7}$ cycloalkylsulfinyl group
(44) an optionally substituted $C_{6-14}$ arylsulfinyl group
(45) an optionally substituted heterocyclyl-sulfinyl group
(46) a sulfo group
(47) a sulfamoyl group
(48) a sulfinamoyl group
(49) a sulfenamoyl group
(50) a thiocarbamoyl group
(51) an optionally substituted carbamoyl group [e.g., optionally substituted alkyl-carbamoyl and the like]
(52) an optionally substituted amino group
[e.g.,
amino,
an optionally substituted mono- or di-alkylamino group,
an optionally substituted mono- or di-$C_{3-7}$ cycloalkylamino group,
an optionally substituted mono- or di-$C_{5-14}$ arylamino group,
an optionally substituted mono- or di-$C_{7-15}$ aralkylamino group,
an optionally substituted heterocyclyl-amino group,
an optionally substituted $C_{6-14}$ aryl-carbonylamino group, a formylamino group,
an optionally substituted alkyl-carbonylamino group (e.g., a mono-($C_{1-6}$ alkyl-carbonyl)-amino group),
an optionally substituted $C_{3-7}$ cycloalkyl-carbonylamino group,
an optionally substituted heterocyclyl-carbonylamino group,
an optionally substituted alkoxy-carbonylamino group,
an optionally substituted $C_{3-7}$ cycloalkyloxy-carbonylamino group,
an optionally substituted heterocyclyl-oxycarbonylamino group,
an optionally substituted carbamoylamino group,
an optionally substituted alkylsulfonylamino group,
an optionally substituted $C_{3-7}$ cycloalkylsulfonylamino group,
an optionally substituted heterocyclyl-sulfonylamino group,
an optionally substituted $C_{6-14}$ arylsulfonylamino group]

As respective substituents of the "optionally substituted alkoxy-carbonyl group", "optionally substituted alkyl group", "optionally substituted alkenyl group", "optionally substituted alkynyl group", "optionally substituted alkoxy group", "optionally substituted alkyl-carbonyloxy group", "optionally substituted alkoxy-carbonyloxy group", "optionally substituted mono-alkyl-carbamoyloxy group", "optionally substituted di-alkyl-carbamoyloxy group", "optionally substituted alkylsulfanyl group", "optionally substituted alkyl-carbonyl group", "optionally substituted alkylsulfonyl group", "optionally substituted alkylsulfinyl group", "optionally substituted alkyl-carbamoyl group", "optionally substituted mono- or di-alkylamino group", "optionally substituted alkyl-carbonylamino group", "optionally substituted mono-($C_{1-6}$ alkyl-carbonyl)-amino group", "optionally substituted alkoxy-carbonylamino group" and "optionally substituted alkylsulfonylamino group" in substituent group A, substituents selected from the following substituent group B can be mentioned. The number of the substituents is one to maximum substitutable number, more preferably 1-3, further preferably 1.

In addition, as respective substituents of the "optionally substituted $C_{6-14}$ aryloxy-carbonyl group", "optionally substituted $C_{7-16}$ aralkyloxy-carbonyl group", "optionally substituted $C_{3-7}$ cycloalkyl-$C_{2-6}$ alkynyl group", "optionally substituted $C_{3-7}$ cycloalkyl group", "optionally substituted $C_{6-14}$ aryl group", "optionally substituted $C_{7-16}$ aralkyl group", "optionally substituted $C_{6-14}$ aryl-$C_{2-6}$ alkenyl group", "optionally substituted heterocyclic group", "optionally substituted $C_{3-7}$ cycloalkyloxy group", "optionally substituted $C_{6-14}$ aryloxy group", "optionally substituted $C_{7-16}$ aralkyloxy group", "optionally substituted $C_{6-14}$ arylcarbonyloxy group", "optionally substituted mono- or di-$C_{6-14}$ aryl-carbamoyloxy group", "optionally substituted heterocyclyl-oxy group", "optionally substituted aromatic heterocyclyl-oxy group", "optionally substituted $C_{3-7}$ cycloalkylsulfanyl group", "optionally substituted $C_{6-14}$ arylsulfanyl group", "optionally substituted $C_{7-16}$ aralkylsulfanyl group", "optionally substituted heterocyclyl-sulfanyl group", "optionally substituted $C_{3-7}$ cycloalkyl-carbonyl group", "optionally substituted $C_{6-14}$ aryl-carbonyl group", "optionally substituted $C_{7-16}$ aralkyl-carbonyl group", "optionally substituted heterocyclyl-carbonyl group", "optionally substituted $C_{3-7}$ cycloalkylsulfonyl group", "optionally substituted $C_{6-14}$ arylsulfonyl group", "optionally substituted heterocyclyl-sulfonyl group", "optionally substituted $C_{3-7}$ cycloalkylsulfinyl group", "optionally substituted $C_{6-14}$ arylsulfinyl group", "optionally substituted heterocyclyl-sulfinyl group", "optionally substituted carbamoyl group", "optionally substituted amino group", "optionally substituted mono- or di-$C_{3-8}$ cycloalkylamino group", "optionally substituted mono- or di-$C_{6-14}$ arylamino group", "optionally substituted mono- or di-$C_{7-16}$ aralkylamino group", "optionally substituted heterocyclyl-amino group", "optionally substituted $C_{6-14}$ aryl-carbonylamino group", "optionally substituted $C_{3-8}$ cycloalkyl-carbonylamino group", "optionally substituted heterocyclyl-carbonylamino group", "optionally substituted $C_{3-8}$ cycloalkoxy-carbonylamino group", "optionally substituted heterocyclyl-oxycarbonylamino group", "optionally substituted carbamoylamino group", "optionally substituted alkylsulfonylamino group", "optionally substituted $C_{3-8}$ cycloalkylsulfonylamino group", "optionally substituted heterocyclyl-sulfonylamino group" and "optionally substituted $C_{6-14}$ arylsulfonylamino group" in substituent group A, for example, substituents selected from the following substituent group B and the following substituent group B' can be mentioned. The number of the substituents is one to maximum substitutable number, more preferably 1-3, further preferably 1.

[Substituent Group B]

In the present specification, substituent group B includes substituents of the following (a)-(bb).

(a) a halogen atom
(b) a hydroxy group
(c) a nitro group
(d) a cyano group
(e) an optionally substituted $C_{6-14}$ aryl group [e.g., a $C_{6-14}$ aryl group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-15}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(f) an optionally substituted $C_{6-14}$ aryloxy group [e.g., $C_{6-14}$ aryloxy group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{5-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(g) an optionally substituted $C_{7-16}$ aralkyloxy group [e.g., a $C_{7-16}$ aralkyloxy group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(h) an optionally substituted 5- to 10-membered heterocyclic m group containing 1 to 4 hetero atoms selected from a nitrogen atom, a sulfur atom and an oxygen atom [e.g., a 5- to 10-membered heterocyclic group containing 1 to 4 hetero atoms selected from a nitrogen atom, a sulfur atom and an oxygen atom (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinolin-2-yl) optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(i) an optionally substituted amino group [e.g., an amino group optionally substituted by 1 or 2 substituents selected from the group consisting of $C_{1-6}$ alkyl, $C_{2-6}$ alkenyl, $C_{6-14}$ aryl, $C_{7-16}$ aralkyl, a heterocyclic group and heterocyclyl-alkyl, each being optionally substituted (examples of the substituent of the "$C_{1-6}$ alkyl, $C_{2-6}$ alkenyl, $C_{6-14}$ aryl, $C_{7-16}$ aralkyl, heterocyclic group and heterocyclyl-alkyl, each being optionally substituted" include a halogen atom, hydroxy, cyano, amino, optionally halogenated $C_{1-6}$ alkyl (excluding substituents of alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, mono- or di-$C_{6-14}$ aryl-carbamoyl and the like. The number of the substituents is one or more (e.g., 1-5). The "heterocyclic group" and "heterocyclyl-" of "heterocyclyl-alkyl" are exemplified by those similar to the aforementioned "heterocyclic group".)

(j) $C_{3-7}$ cycloalkyl (k) an optionally substituted $C_{1-6}$ alkoxy group [e.g., a $C_{1-6}$ alkoxy group optionally substituted by one or more (e.g., 1-5) substituents selected from the group consisting of a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, trimethylsilyl (TMS) and the like]

(l) a formyl group
(m) a $C_{1-6}$ alkyl-carbonyl group (e.g., acetyl and the like)
(n) a $C_{3-7}$ cycloalkyl-carbonyl group
(o) a $C_{6-14}$ aryl-carbonyl group
(p) a $C_{7-16}$ aralkyl-carbonyl group
(q) a $C_{1-6}$ alkoxy-carbonyl group
(r) a $C_{6-14}$ aryloxy-carbonyl group
(s) a $C_{7-16}$ aralkyloxy-carbonyl group
(t) a $C_{1-6}$ alkylsulfanyl group
(u) a $C_{1-6}$ alkylsulfinyl group
(v) a $C_{1-6}$ alkylsulfonyl group
(w) a carbamoyl group
(x) a thiocarbamoyl group
(y) a mono-$C_{1-6}$ alkyl-carbamoyl group (e.g., methylcarbamoyl, ethylcarbamoyl and the like)
(z) a di-$C_{1-6}$ alkyl-carbamoyl group (e.g., dimethylcarbamoyl, diethylcarbamoyl, ethylmethylcarbamoyl and the like)
(aa) a mono- or di-$C_{6-14}$ aryl-carbamoyl group (e.g., phenylcarbamoyl, 1-naphthylcarbamoyl, 2-naphthylcarbamoyl and the like)
(bb) a mono- or di-5- to 7-membered heterocyclyl containing 1 to 4 hetero atoms selected from a nitrogen atom, a sulfur atom and an oxygen atom-carbamoyl group (e.g., 2-pyridylcarbamoyl, 3-pyridylcarbamoyl, 4-pyridylcarbamoyl, 2-thienylcarbamoyl, 3-thienylcarbamoyl and the like)

[Substituent Group B']

In the present specification, substituent group B' comprises substituents in the following (a)-(c).

(a) an optionally substituted $C_{1-6}$ alkyl group [e.g., a $C_{1-6}$ alkyl group optionally substituted by one or more (e.g., 1-5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(b) an optionally substituted $C_{2-6}$ alkenyl group [e.g., a $C_{2-6}$ alkenyl group optionally substituted by one or more (e.g., 1-5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like]

(c) an optionally substituted $C_{2-6}$ alkynyl group [e.g., a $C_{2-6}$ alkynyl group optionally substituted by one or more (e.g., 1-5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

[Substituent group C]

In the present specification, substituent group $C_1$ includes substituents of the following (1)-(6).
(1) an oxo group
(2) an imino group
(3) an imino group optionally substituted by one substituent selected from an optionally substituted alkyl group, an optionally substituted $C_{3-7}$ cycloalkyl group, an optionally substituted $C_{6-14}$ aryl group, an optionally substituted $C_{7-16}$ aralkyl group, an optionally substituted heterocyclic group, a hydroxy group, an optionally substituted alkoxy group, an optionally substituted $C_{3-7}$ cycloalkyloxy group, an optionally substituted $C_{6-14}$ aryloxy group, an optionally substituted $C_{7-16}$ aralkyloxy group and an optionally substituted heterocyclyl-oxy group
(4) a methylidene group optionally substituted by 1 or 2 substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group and an optionally substituted heterocyclic group
(5) an optionally substituted $C_{3-7}$ cycloalkylidene group
(6) a $C_{2-7}$ alkylene group optionally substituted by one or more (e.g., 1-3) substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group and an optionally substituted heterocyclic group (when the $C_{2-7}$ alkylene group is present as a divalent group on one carbon atom, in other words, when the $C_{2-7}$ alkylene group substitutes two hydrogen atoms on the aforementioned carbon atom, the $C_{2-7}$ alkylene group forms $C_3$-8 cycloalkane together with the aforementioned carbon atom)

Examples of the "optionally substituted alkyl group", "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted alkoxy group", "optionally substituted $C_{3-7}$ cycloalkyloxy group", "optionally substituted $C_{6-14}$ aryloxy group", "optionally substituted $C_{7-16}$ aralkyloxy group" and "optionally substituted heterocyclyl-oxy group", as the substituents of the substituents constituting substituent group C, include those similar to the substituents described as the substituent constituting substituent group A.

In addition, examples of the substituent of the "optionally substituted $C_{3-7}$ cycloalkylidene group" include substituents selected from the above-mentioned substituent group B and the above-mentioned substituent group B'. The number of the substituents is one-maximum substitutable number, more preferably 1-3, more preferably 1.

The symbols in the formula (I) are explained below.

$R^1$ is an optionally substituted hydrocarbon group or an optionally substituted heterocyclic group.

Examples of the "hydrocarbon group" of the "optionally substituted hydrocarbon group" for $R^1$ include non-cyclic hydrocarbon groups (e.g., $C_{1-6}$ alkyl group), aromatic hydrocarbon ring groups (e.g., $C_{6-14}$ aryl group), and nonaromatic hydrocarbon ring groups (e.g., $C_{3-7}$ cycloalkyl group). Preferred are $C_{1-6}$ alkyl groups (e.g., methyl, ethyl, propyl, isopropyl, butyl, isobutyl, sec-butyl), $C_{6-14}$ aryl groups (e.g., phenyl), and $C_{3-7}$ cycloalkyl groups (e.g., cycloheptyl).

Examples of the "substituent" of the "optionally substituted hydrocarbon group" for $R^1$ include halogen atoms (e.g., fluorine atom, chlorine atom, bromine atom), cyano, optionally substituted $C_{1-6}$ alkyl groups (e.g., methyl, ethyl), optionally substituted $C_{1-6}$ alkoxy groups (e.g., methoxy), optionally substituted $C_{6-14}$ aryl groups (e.g., phenyl), optionally substituted nonaromatic heterocyclic groups (e.g., tetrahydrofuryl), and optionally substituted aromatic heterocyclic groups (e.g., oxazolyl). Preferred are halogen atoms (e.g., fluorine atom, chlorine atom, bromine atom), cyano, $C_{1-6}$ alkyl groups (e.g., methyl, ethyl) optionally substituted by a halogen atom (e.g., fluorine atom), $C_{1-6}$ alkoxy groups (e.g., methoxy), $C_{6-14}$ aryl groups (e.g., phenyl) optionally substituted by a halogen atom (e.g., fluorine atom, chlorine atom), nonaromatic heterocyclic groups (e.g., tetrahydrofuryl), and aromatic heterocyclic groups (e.g., oxazolyl) optionally substituted by a $C_{1-6}$ alkyl group (e.g., methyl).

Preferred as the "optionally substituted hydrocarbon group" for $R^1$ are (1) $C_{1-6}$ alkyl groups (e.g., methyl, ethyl, propyl, isopropyl, butyl, isobutyl, sec-butyl) optionally substituted by substituent(s) selected from halogen atoms (e.g., a fluorine atom), $C_{1-6}$ alkoxy groups (e.g., methoxy), $C_{6-14}$ aryl groups (e.g., phenyl) optionally substituted by a halogen atom (e.g., fluorine atom, chlorine atom), nonaromatic heterocyclic groups (e.g., tetrahydrofuryl) and aromatic heterocyclic groups (e.g., oxazolyl) optionally substituted by a $C_{1-6}$ alkyl group (e.g., methyl), (2) $C_{6-14}$ aryl groups (e.g., phenyl) optionally substituted by substituent(s) selected from halogen atoms (e.g., fluorine atom, chlorine atom, bromine atom), cyano, $C_{1-6}$ alkyl groups (e.g., methyl, ethyl) optionally substituted by a halogen atom (e.g., fluorine atom) and $C_{1-6}$ alkoxy groups (e.g., methoxy), and (3) $C_{3-7}$ cycloalkyl groups (e.g., cycloheptyl).

Examples of the "heterocyclic group" of the "optionally substituted heterocyclic group" for $R^1$ include nonaromatic heterocyclic groups (e.g., 3- to 14-membered nonaromatic heterocyclic group), and aromatic heterocyclic groups (e.g., 5- or 6-membered monocyclic aromatic heterocyclic group, 5- to 10-membered aromatic fused heterocyclic group). Preferred are 3- to 14-membered nonaromatic heterocyclic groups (e.g., pyrrolidinyl, tetrahydrofuryl, tetrahydropyranyl, dihydropyridazinyl, dihydrobenzofuranyl, benzodioxolyl), and 5- or 6-membered monocyclic aromatic heterocyclic groups (e.g., thienyl, pyrazolyl, oxazolyl, pyridyl, pyrimidinyl).

Examples of the "substituent" of the "optionally substituted heterocyclic group" for $R^1$ include halogen atoms (e.g., fluorine atom, chlorine atom), cyano, oxo, optionally substituted $C_{1-6}$ alkyl groups (e.g., methyl), and optionally substituted $C_{1-6}$ alkoxy groups (e.g., methoxy). Preferred are halogen atoms (e.g., fluorine atom, chlorine atom), cyano, oxo, $C_{1-6}$ alkyl groups (e.g., methyl) optionally substituted by a halogen atom (e.g., fluorine atom), and $C_{1-6}$ alkoxy groups (e.g., methoxy).

Preferred as the "optionally substituted heterocyclic group" for $R^1$ are (1) 3- to 14-membered nonaromatic heterocyclic groups (e.g., pyrrolidinyl, tetrahydrofuryl, tetrahydropyranyl, dihydropyridazinyl, dihydrobenzofuranyl, benzodioxolyl) optionally substituted by substituent(s) selected from halogen atoms (e.g., fluorine atom), oxo and $C_{1-6}$ alkyl groups (e.g., methyl), and (2) 5- or 6-membered monocyclic aromatic heterocyclic groups (e.g., thienyl, pyrazolyl, oxazolyl, pyridyl, pyrimidinyl) optionally substituted by substituent(s) selected from halogen atoms (e.g., fluorine atom, chlorine atom), cyano, $C_{1-6}$ alkyl groups (e.g., methyl) optionally substituted by a halogen atom (e.g., fluorine atom) and $C_{1-6}$ alkoxy groups (e.g., methoxy).

In one embodiment of the present invention, $R^1$ is preferably
(1) an optionally substituted non-cyclic hydrocarbon group;
(2) an optionally substituted aromatic hydrocarbon ring group;
(3) an optionally substituted nonaromatic hydrocarbon ring group; or
(4) an optionally substituted heterocyclic group, more preferably
(1) optionally substituted $C_{1-6}$ alkyl;
(2) optionally substituted $C_{3-7}$ cycloalkyl;
(3) optionally substituted phenyl;
(4) optionally substituted dihydrobenzofuranyl;
(5) optionally substituted benzodioxolyl;
(6) optionally substituted pyridyl;
(7) optionally substituted pyrimidinyl;
(8) optionally substituted isoxazolyl;
(9) optionally substituted tetrahydrofuranyl;
(10) optionally substituted thienyl;
(11) optionally substituted pyrazolyl;
(12) optionally substituted pyrrolidinonyl;
(13) optionally substituted tetrahydropyranyl; or
(14) optionally substituted dihydropyridazinonyl,
further preferably
(1) $C_{1-6}$ alkyl optionally substituted by 1-5 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom, cyano, and $C_{1-6}$ alkyl optionally substituted by 1 to 3 halogen atoms;
(7) pyrimidinyl optionally substituted by 1 to 3 halogen atoms or cyano;
(8) isoxazolyl substituted by 1 to 3 $C_{1-6}$ alkyls;
(9) tetrahydrofuranyl;
(10) thienyl optionally substituted by 1 to 3 substituents selected from a halogen atom, cyano and $C_{1-6}$ alkyl;
(11) pyrazolyl optionally substituted by 1 to 3 substituents selected from a halogen atom, cyano, $C_{1-6}$ alkyl optionally substituted by 1 to 3 halogen atoms, and $C_{1-6}$ alkoxy;
(12) pyrrolidinonyl optionally substituted by 1 to 3 halogen atoms;
(13) tetrahydropyranyl; or
(14) dihydropyridazinonyl substituted by 1 to 3 $C_{1-6}$ alkyls, further preferably, (1) phenyl optionally substituted by 1 to 3 substituents selected from a halogen atom, cyano, $C_{1-6}$ alkyl optionally substituted by 1 to 3 halogen atoms and $C_{1-6}$ alkoxy;
(2) benzodioxolyl substituted by 1 to 3 halogen atoms;
(3) pyridyl optionally substituted by 1 to 3 substituents selected from a halogen atom, cyano, and $C_{1-6}$ alkyl optionally substituted by 1 to 3 halogen atoms;
(4) thienyl optionally substituted by 1 to 3 substituents selected from a halogen atom, cyano and $C_{1-6}$ alkyl;
(5) pyrazolyl optionally substituted by 1 to 3 substituents selected from a halogen atom, cyano, $C_{1-6}$ alkyl optionally substituted by 1 to 3 halogen atoms, and $C_{1-6}$ alkoxy;
(6) pyrrolidinonyl optionally substituted by 1 to 3 halogen atoms;
(7) tetrahydropyranyl; or
(8) dihydropyridazinonyl substituted by 1 to 3 $C_{1-6}$ alkyls,
particularly preferably
(1) phenyl optionally substituted by 1 to 3 substituents selected from a halogen atom, cyano, $C_{1-6}$ alkyl optionally substituted by 1 to 3 halogen atoms and $C_{1-6}$ alkoxy;
(2) benzodioxolyl substituted by 1 to 3 halogen atoms;
(3) pyridyl optionally substituted by 1 to 3 substituents selected from a halogen atom and $C_{1-6}$ alkyl optionally substituted by 1 to 3 halogen atoms; or
(4) thienyl optionally substituted by 1 to 3 substituents selected from a halogen atom, cyano and $C_{1-6}$ alkyl.

In another embodiment of the present invention, $R^1$ is preferably.
(1) $C_{1-6}$ alkyl optionally substituted by 1 to 3 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and $C_{1-6}$ alkyl optionally substituted by 1 to 3 halogen atoms;
(7) pyrimidinyl;
(8) isoxazolyl substituted by 1 to 3 $C_{1-6}$ alkyls;
(9) tetrahydrofuranyl; or
(10) pyrazolyl, more preferably
(1) $C_{3-7}$ cycloalkyl;
(2) phenyl optionally substituted by 1 to 3 substituents selected from a halogen atom, cyano, $C_{1-6}$ alkyl optionally substituted by 1 to 3 halogen atoms and $C_{1-6}$ alkoxy;
(3) dihydrobenzofuranyl;
(4) benzodioxolyl substituted by 1 to 3 halogen atoms;
(5) pyridyl substituted by 1 to 3 substituents selected from $C_1$-6 alkyl substituted by 1 to 3 halogen atoms; or
(6) pyrazolyl; or
(1) $C_{1-6}$ alkyl;
(2) phenyl optionally substituted by 1 to 3 substituents selected from a halogen atom, cyano and $C_{1-6}$ alkyl optionally substituted by 1 to 3 halogen atoms;
(3) pyridyl substituted by 1 to 3 "$C_{1-6}$ alkyl groups substituted by 1 to 3 halogen atoms";
(4) pyrimidinyl; or
(5) tetrahydrofuranyl.

$L^1$ is a bond, —O—, —CH$_2$—, —CH$_2$—O— or —O—CH$_2$—.

As $L^1$, a bond, —O— or —CH$_2$—O— is preferable.

In one embodiment of the present invention, $L^1$ is preferably a bond, —O—, —CH$_2$—O— or —O—CH$_2$—, more preferably a bond, —O— or —CH$_2$—O—, further preferably a bond or —O—.

In another embodiment of the present invention, $L^1$ is preferably —O— or —CH$_2$—O—.

Ring D is a further optionally substituted ring.

Examples of the "ring" of the "further optionally substituted ring" for ring D include aromatic hydrocarbon rings (e.g., 6- to 10-membered aromatic hydrocarbon ring), and aromatic heterocycles (e.g., 6-membered aromatic heterocycle). Preferred are 6- to 10-membered aromatic hydrocarbon rings (e.g., a benzene ring) and 6-membered aromatic heterocycles (e.g., a pyridine ring).

Examples of the "substituent" of the "further optionally substituted ring" for ring D include halogen atoms (e.g., fluorine atom). Preferred is a fluorine atom.

As ring D, (1) 6- to 10-membered aromatic hydrocarbon rings (e.g., benzene ring) optionally substituted by a halogen atom (e.g., fluorine atom), and (2) 6-membered aromatic heterocycles (e.g., pyridine ring) are preferable.

In one embodiment of the present invention, ring D is preferably
(1) an optionally substituted 6- to 14-membered aromatic hydrocarbon ring, or
(2) an optionally substituted 5- or 6-membered aromatic heterocycle,
more preferably
(1) an optionally substituted 6-10-membered aromatic hydrocarbon ring, or
(2) an optionally substituted 6-membered aromatic heterocycle, further preferably
(1) an optionally substituted benzene ring, or
(2) an optionally substituted pyridine ring,
particularly preferably a benzene ring.

A partial structure:

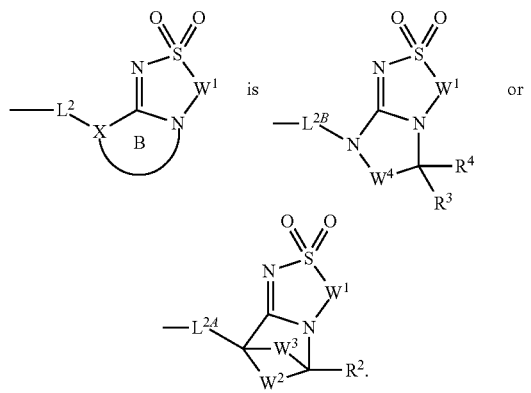

$L^{2A}$ is a bond, —O—, —CH$_2$—, —CH$_2$—O— or —O—CH$_2$—.

As $L^{2A}$, a bond or —O—CH$_2$— is preferable.

In one embodiment of the present invention, $L^{2A}$ is preferably a bond, —O— or —O—CH$_2$—, more preferably a bond or —O—CH$_2$—, particularly preferably a bond.

$L^{2B}$ is a bond, —O—, —CH$_2$— or —CH$_2$—O—.

As $L^{2B}$, a bond is preferable.

In one embodiment of the present invention, $L^{2B}$ is preferably a bond or —CH$_2$—, more preferably a bond.

$W^1$ is optionally substituted $C_{1-3}$ alkylene or optionally substituted $C_{2-3}$ alkenylene.

As $W^1$, optionally substituted $C_{1-3}$ alkylene (e.g., ethylene (—CH$_2$—CH$_2$—)) is preferable, $C_{1-3}$ alkylene (e.g., ethylene (—CH$_2$—CH$_2$—)) is more preferable, and ethylene (—CH$_2$—CH$_2$—) is particularly preferable.

$W^2$, $W^3$ and $W^4$ are each independently optionally substituted $C_{1-3}$ alkylene.

As $W^2$, $C_{1-3}$ alkylene (e.g., ethylene (—CH$_2$—CH$_2$—)) is preferable, and ethylene (—CH$_2$—CH$_2$—) is more preferable.

As $W^3$, $C_{1-3}$ alkylene (e.g., ethylene (—CH$_2$—CH$_2$—)) is preferable, and ethylene (—CH$_2$—CH$_2$—) is more preferable.

As $W^4$, $C_{1-3}$ alkylene (e.g., ethylene (—CH$_2$—CH$_2$—)) optionally substituted by a $C_{1-6}$ alkyl group (e.g., methyl) is preferable, and ethylene (—CH$_2$—CH$_2$—) optionally substituted by methyl is more preferable.

In one embodiment of the present invention, $W^2$, $W^3$ and $W^4$ are preferably each independently ethylene (—CH$_2$—CH$_2$—) optionally substituted by 1 to 3 substituents selected from
(a) a halogen atom;
(b) hydroxy;
(c) $C_{1-6}$ alkyl optionally substituted by 1 to 3 halogen atoms;
(d) $C_{1-6}$ alkoxy; and
(e) $C_{1-6}$ alkyl-carbonyl,
more preferably each independently ethylene (—CH$_2$—CH$_2$—) optionally substituted by 1 to 3 $C_{1-6}$ alkyls optionally substituted by 1 to 3 halogen atoms, further preferably ethylene (—CH$_2$—CH$_2$—).

$R^2$, $R^3$ and $R^4$ are each independently a hydrogen atom or a substituent.

$R^2$, $R^3$ and $R^4$ are each preferably a hydrogen atom.

Preferable examples of the substituent, partial structure, ring and the like explained in the present specification are more preferably used in combination.

In the present invention, preferable compound (I) includes the following compounds.

[Compound I-1]
Compound (I) wherein the partial structure:

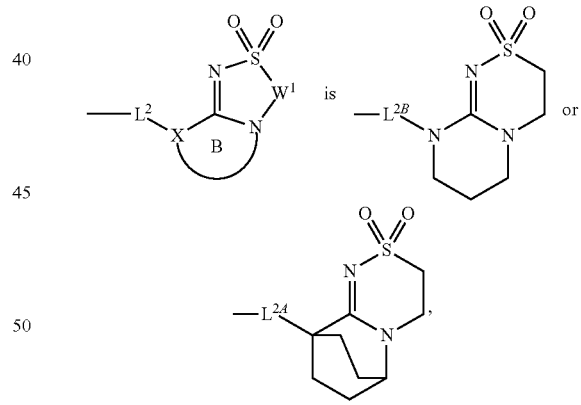

namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond or —O—CH$_2$—;
$L^{2B}$ is a bond,
or a salt thereof.

[Compound I-2]
Compound (I) or compound (I-1) wherein ring D is a benzene ring, or a salt thereof.

[Compound I-3]
Compound (I), compound (I-1) or compound (I-2) wherein $L^1$ is a bond, —O— or —CH$_2$—O—, or a salt thereof.

[Compound I-4]
Compound (I), compound (I-1), compound (I-2) or compound (I-3) wherein $R^1$ is
(1) $C_{1-6}$ alkyl optionally substituted by 1 to 3 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and $C_{1-6}$ alkyl optionally substituted by 1 to 3 halogen atoms;
(7) pyrimidinyl;
(8) isoxazolyl substituted by 1 to 3 $C_{1-6}$ alkyls;
(9) tetrahydrofuranyl; or
(10) pyrazolyl;
or a salt thereof.

[Compound I-5]
Compound (I), compound (I-1), compound (I-2), compound (I-3) or compound (I-4) wherein $R^1$ is
(1) $C_{3-7}$ cycloalkyl;
(2) phenyl optionally substituted by 1 to 3 substituents selected from a halogen atom, cyano, $C_{1-6}$ alkyl optionally substituted by 1 to 3 halogen atoms and $C_{1-6}$ alkoxy;
(3) dihydrobenzofuranyl;
(4) benzodioxolyl substituted by 1 to 3 halogen atoms;
(5) pyridyl substituted by 1 to 3 substituents selected from $C_{1-6}$ alkyl substituted by 1 to 3 halogen atoms; or
(6) pyrazolyl;
or a salt thereof.

[Compound I-6]
Compound (I), compound (I-1), compound (I-2), compound (I-3) or compound (I-4) wherein $R^1$ is
(1) $C_{1-6}$ alkyl optionally substituted by 1 to 3 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and $C_{1-6}$ alkyl optionally substituted by 1 to 3 halogen atoms;
(7) pyrimidinyl;
(8) isoxazolyl substituted by 1 to 3 $C_{1-6}$ alkyls;
(9) tetrahydrofuranyl; or
(10) pyrazolyl;
$L^1$ is a bond, —O— or —CH$_2$—O—;
ring D is a benzene ring;
the partial structure:

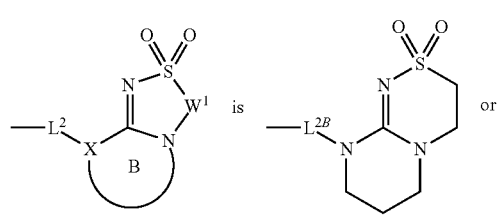

is

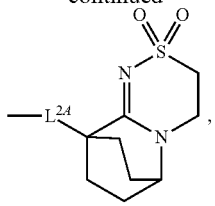

or namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond or —O—CH$_2$—; or
$L^{2B}$ is a bond,
or a salt thereof.

[Compound I-7]
Compound (I), compound (I-1), compound (I-2), compound (I-3), compound (I-4), compound (I-5) or compound (I-6) wherein $R^1$ is
(1) $C_{3-7}$ cycloalkyl;
(2) phenyl optionally substituted by 1 to 3 substituents selected from a halogen atom, cyano, $C_{1-6}$ alkyl optionally substituted by 1 to 3 halogen atoms and $C_{1-6}$ alkoxy;
(3) dihydrobenzofuranyl;
(4) benzodioxolyl substituted by 1 to 3 halogen atoms;
(5) pyridyl substituted by 1 to 3 substituents selected from $C_{1-6}$ alkyl substituted by 1 to 3 halogen atoms; or
(6) pyrazolyl;
$L^1$ is a bond, or —O—;
ring D is a benzene ring;
the partial structure:

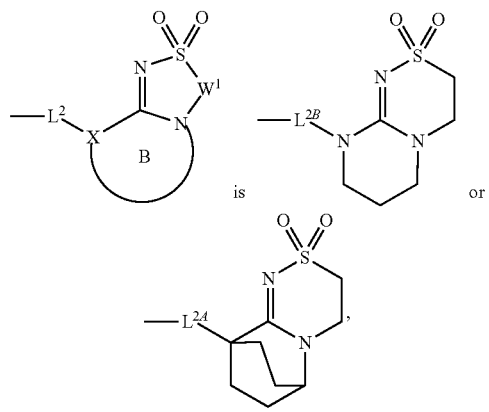

namely,
$W^1$, $W^2$, $W^3$ and $W^4$ are each ethylene (—CH$_2$—CH$_2$—);
$R^2$, $R^3$ and $R^4$ are each a hydrogen atom;
$L^{2A}$ is a bond or —O—CH$_2$—; or
$L^{2B}$ is a bond,
or a salt thereof.

[Compound I-8]
Compound (I), compound (I-1), compound (I-2), compound (I-3), compound (I-4) or compound (I-6) wherein $R^1$ is
(1) $C_{1-6}$ alkyl;
(2) phenyl optionally substituted by 1 to 3 substituents selected from a halogen atom, cyano and $C_{1-6}$ alkyl optionally substituted by 1 to 3 halogen atoms;
(3) pyridyl substituted by 1 to 3 substituents selected from $C_{1-6}$ alkyl substituted by 1 to 3 halogen atoms;

(4) pyrimidinyl; or
(5) tetrahydrofuranyl;
  $L^1$ is —O— or —CH$_2$—O—;
  ring D is a benzene ring;
  the partial structure:

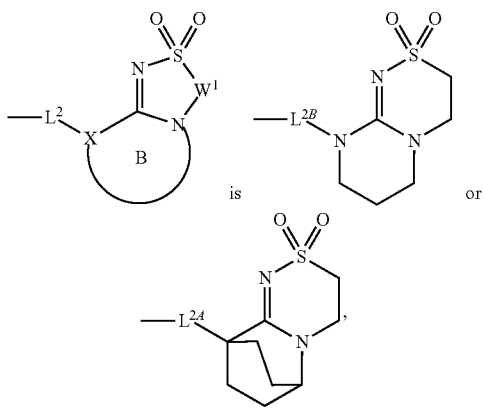

namely,
  $W^2$, $W^3$ and $W^4$ are each ethylene (—CH$_2$—CH$_2$—);
  $R^2$, $R^3$ and $R^4$ are each a hydrogen atom;
  $L^{2A}$ is a bond; or
  $L^{2B}$ is a bond,
or a salt thereof.

In another embodiment of the present invention, preferable compound (I) includes the following compounds.

[Compound (I-A)]
  Compound (I) wherein $R^1$ is
(1) an optionally substituted non-cyclic hydrocarbon group;
(2) an optionally substituted aromatic hydrocarbon ring group;
(3) an optionally substituted nonaromatic hydrocarbon ring group; or
(4) an optionally substituted heterocyclic group, or a salt thereof.

[Compound (I-B)]
  Compound (I) or compound (I-A) wherein the partial structure:

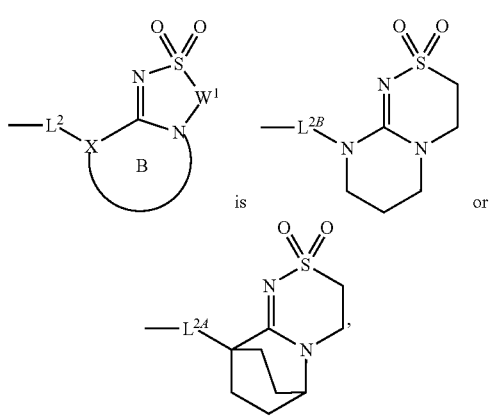

namely,

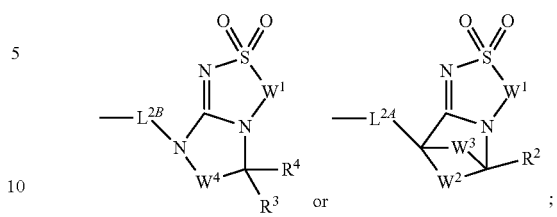

wherein (same in the following description),
  $W^1$, $W^2$, $W^3$ and $W^4$ are each ethylene (—CH$_2$—CH$_2$—);
  $R^2$, $R^3$ and $R^4$ are each a hydrogen atom; and
  ethylene (—CH$_2$—CH$_2$—) for $W^2$, $W^3$ or $W^4$ is optionally substituted by 1 to 3 substituents selected from
  (a) a halogen atom;
  (b) hydroxy;
  (c) C$_{1-6}$ alkyl optionally substituted by 1 to 3 halogen atoms;
  (d) C$_{1-6}$ alkoxy; and
  (e) C$_{1-6}$ alkyl-carbonyl,
or a salt thereof.

[Compound (I-C)]
  Compound (I), compound (I-A) or compound (I-B) wherein the partial structure:

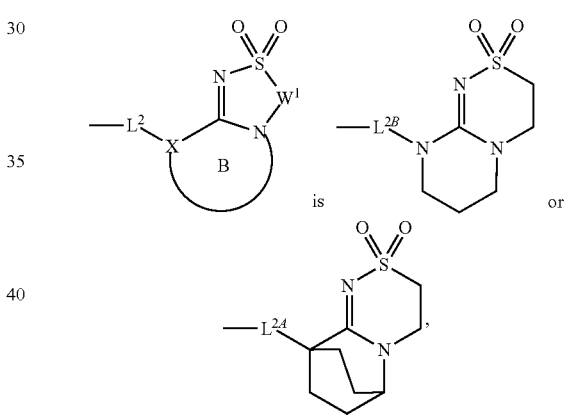

namely,
  $W^1$, $W^2$, $W^3$ and $W^4$ are each ethylene (—CH$_2$—CH$_2$—);
  $R^2$, $R^3$ and $R^4$ are each a hydrogen atom; and
  ethylene (—CH$_2$—CH$_2$—) for $W^2$, $W^3$ or $W^4$ is optionally substituted by 1 to 3 C$_{1-6}$ alkyls optionally substituted by 1 to 3 halogen atoms,
or a salt thereof.

[Compound (I-D)]
  Compound (I), compound (I-A), compound (I-B) or compound (I-C) wherein the partial structure:

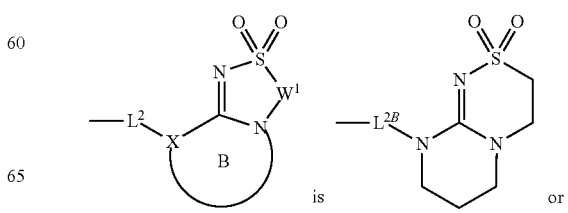

-continued

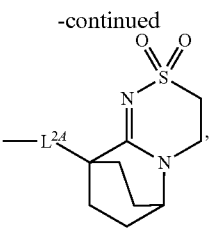

namely,
W$^1$, W$^2$, W$^3$ and W$^4$ are each ethylene (—CH$_2$—CH$_2$—);
R$^2$, R$^3$ and R$^4$ are each a hydrogen atom;
L$^{2A}$ is a bond, —O—, —CH$_2$—, —CH$_2$—O— or —O—CH$_2$—; and L$^{2B}$ is a bond, —O—, —CH$_2$— or —CH$_2$—O—,
or a salt thereof.
[Compound (I-E)]
Compound (I), compound (I-A), compound (I-B), compound (I-C) or compound (I-D) wherein the partial structure:

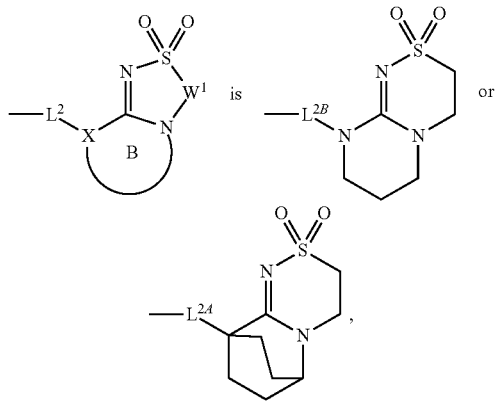

namely,
W$^1$, W$^2$, W$^3$ and W$^4$ are each ethylene (—CH$_2$—CH$_2$—);
R$^2$, R$^3$ and R$^4$ are each a hydrogen atom;
L$^{2A}$ is a bond or —O—CH$_2$—; and
L$^{2B}$ is a bond,
or a salt thereof.
[Compound (I-F)]
Compound (I), compound (I-A), compound (I-B), compound (I-C), compound (I-D) or compound (I-E) wherein ring D is
(1) an optionally substituted 6-14-membered aromatic hydrocarbon ring, or
(2) an optionally substituted 5- or 6-membered aromatic heterocycle,
or a salt thereof.
[Compound (I-G)]
Compound (I), compound (I-A), compound (I-B), compound (I-C), compound (I-D), compound (I-E) or compound (I-F) wherein ring D is
(1) an optionally substituted 6- to 10-membered aromatic hydrocarbon ring, or
(2) an optionally substituted 6-membered aromatic heterocycle,
or a salt thereof.
[Compound (I-H)]
Compound (I), compound (I-A), compound (I-B), compound (I-C), compound (I-D), compound (I-E), compound (I-F) or compound (I-G) wherein ring D is
(1) an optionally substituted benzene ring, or
(2) an optionally substituted pyridine ring,
or a salt thereof.
[Compound (I-I)]
Compound (I), compound (I-A), compound (I-B), compound (I-C), compound (I-D), compound (I-E), compound (I-F), compound (I-G) or compound (I-H) wherein L$^1$ is a bond, —O—, —CH$_2$—O— or —O—CH$_2$—,
or a salt thereof.
[Compound (I-J)]
Compound (I), compound (I-A), compound (I-B), compound (I-C), compound (I-D), compound (I-E), compound (I-F), compound (I-G), compound (I-H) or compound (I-I) wherein L$^1$ is a bond, —O— or —CH$_2$—O—,
or a salt thereof.
[Compound (I-K)]
Compound (I), compound (I-A), compound (I-B), compound (I-C), compound (I-D), compound (I-E), compound (I-F), compound (I-G), compound (I-H), compound (I-I) or compound (I-J) wherein L$^1$ is a bond or —O—,
or a salt thereof.
[Compound (I-L)]
Compound (I), compound (I-A), compound (I-B), compound (I-C), compound (I-D), compound (I-E), compound (I-F), compound (I-G), compound (I-H), compound (I-I), compound (I-J) or compound (I-K) wherein R$^1$ is
(1) optionally substituted C$_{1-6}$ alkyl;
(2) optionally substituted C$_{3-7}$ cycloalkyl;
(3) optionally substituted phenyl;
(4) optionally substituted dihydrobenzofuranyl;
(5) optionally substituted benzodioxolyl;
(6) optionally substituted pyridyl;
(7) optionally-substituted pyrimidinyl;
(8) optionally substituted isoxazolyl;
(9) optionally substituted tetrahydrofuranyl;
(10) optionally substituted thienyl;
(11) optionally substituted pyrazolyl;
(12) optionally substituted pyrrolidinonyl;
(13) optionally substituted tetrahydropyranyl; or
(14) optionally substituted dihydropyridazinonyl,
or a salt thereof.
[Compound (I-M)]
Compound (I), compound (I-A), compound (I-B), compound (I-C), compound (I-D), compound (I-E), compound (I-F), compound (I-G), compound (I-H), compound (I-I), compound (I-J), compound (I-K) or compound (I-L) wherein R$^1$ is
(1) C$_{1-6}$ alkyl optionally substituted by 1-5 substituents selected from a halogen atom and C$_{1-6}$ alkoxy;
(2) C$_{3-7}$ cycloalkyl;
(3) phenyl optionally substituted by 1 to 3 substituents selected from a halogen atom, cyano, C$_{1-6}$ alkyl optionally substituted by 1 to 3 halogen atoms and C$_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom, cyano, and C$_{1-6}$ alkyl optionally substituted by 1 to 3 halogen atoms;
(7) pyrimidinyl optionally substituted by 1 to 3 halogen atoms or cyano;
(8) isoxazolyl substituted by 1 to 3 C$_{1-6}$ alkyls;
(9) tetrahydrofuranyl;
(10) thienyl optionally substituted by 1 to 3 substituents selected from a halogen atom, cyano and C$_{1-6}$ alkyl;
(11) pyrazolyl optionally substituted by 1 to 3 substituents selected from a halogen atom, cyano, C$_{1-6}$ alkyl optionally substituted by 1 to 3 halogen atoms, and C$_{1-6}$ alkoxy;

(12) pyrrolidinonyl optionally substituted by 1 to 3 halogen atoms;
(13) tetrahydropyranyl; or
(14) dihydropyridazinonyl substituted by 1 to 3 $C_{1-6}$ alkyls, or a salt thereof.

[Compound (I-N)]

Compound (I), compound (I-A), compound (I-B), compound (I-C), compound (I-D), compound (I-E), compound (I-F), compound (I-G), compound (I-H), compound (I-I), compound (I-J), compound (I-K), compound (I-L) or compound (I-M) wherein $R^1$ is
(1) phenyl optionally substituted by 1 to 3 substituents selected from a halogen atom, cyano, $C_{1-6}$ alkyl optionally substituted by 1 to 3 halogen atoms and $C_{1-6}$ alkoxy;
(2) benzodioxolyl substituted by 1 to 3 halogen atoms;
(3) pyridyl optionally substituted by 1 to 3 substituents selected from a halogen atom and $C_{1-6}$ alkyl optionally substituted by 1 to 3 halogen atoms; or
(4) thienyl optionally substituted by 1 to 3 substituents selected from a halogen atom, cyano and $C_{1-6}$ alkyl, or a salt thereof.

[Compound (I-O)]

Compound (I), compound (I-A), compound (I-B), compound (I-F), compound (I-I) or compound (I-L) wherein $R^1$ is
(1) optionally substituted $C_{1-6}$ alkyl;
(2) optionally substituted $C_{3-7}$ cycloalkyl;
(3) optionally substituted phenyl;
(4) optionally substituted dihydrobenzofuranyl;
(5) optionally substituted benzodioxolyl;
(6) optionally substituted pyridyl;
(7) optionally substituted pyrimidinyl;
(8) optionally substituted isoxazolyl;
(9) optionally substituted tetrahydrofuranyl;
(10) optionally substituted thienyl;
(11) optionally substituted pyrazolyl;
(12) optionally substituted pyrrolidinonyl;
(13) optionally substituted tetrahydropyranyl; or
(14) optionally substituted dihydropyridazinonyl;
$L^1$ is a bond, —O—, —O—$CH_2$— or —$CH_2$—O—;
ring D is
(1) an optionally substituted 6-14-membered aromatic hydrocarbon ring, or
(2) an optionally substituted 5- or 6-membered aromatic heterocycle;
the partial structure:

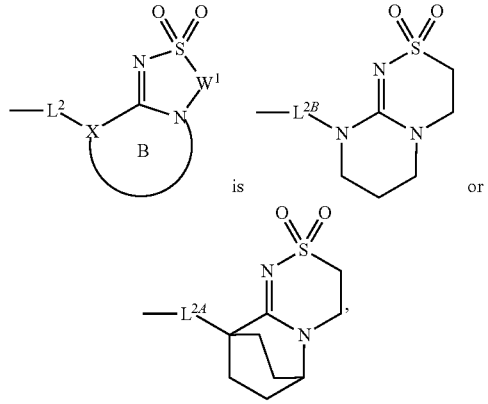

namely,
$W^1$, $W^2$, $W^3$ and $W^4$ are each ethylene (—$CH_2$—$CH_2$—);
$R^2$, $R^3$ and $R^4$ are each a hydrogen atom;
ethylene (—$CH_2$—$CH_2$—) for $W^2$, $W^3$ or $W^4$ is optionally substituted by 1 to 3 substituents selected from
(a) a halogen atom;
(b) hydroxy;
(c) $C_{1-6}$ alkyl optionally substituted by 1 to 3 halogen atoms;
(d) $C_{1-6}$ alkoxy; and
(e) $C_{1-6}$ alkyl-carbonyl;
$L^{2A}$ is a bond, —O—, —$CH_2$—, —$CH_2$—O— or —O—$CH_2$—; and
$L^{2B}$ is a bond or —$CH_2$—,
or a salt thereof.

[Compound (I-P)]

Compound (I), compound (I-A), compound (I-B), compound (I-F), compound (I-G), compound (I-H), compound (I-I), compound (I-J), compound (I-L), compound (I-M) or compound (I-O) wherein $R^1$ is
(1) $C_{1-6}$ alkyl optionally substituted by 1-5 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom, cyano, and $C_{1-6}$ alkyl optionally substituted by 1 to 3 halogen atoms;
(7) pyrimidinyl optionally substituted by 1 to 3 halogen atoms or cyano;
(8) isoxazolyl substituted by 1 to 3 $C_{1-6}$ alkyls;
(9) tetrahydrofuranyl;
(10) thienyl optionally substituted by 1 to 3 substituents selected from a halogen atom, cyano and $C_{1-6}$ alkyl;
(11) pyrazolyl optionally substituted by 1 to 3 substituents selected from a halogen atom, cyano, $C_{1-6}$ alkyl optionally substituted, by 1 to 3 halogen atoms, and $C_{1-6}$ alkoxy;
(12) pyrrolidinonyl optionally substituted by 1 to 3 halogen atoms;
(13) tetrahydropyranyl; or
(14) dihydropyridazinonyl substituted by 1 to 3 $C_{1-6}$ alkyls;
$L^1$ is a bond, —O— or —$CH_2$—O—;
ring D is
(1) an optionally substituted benzene ring, or
(2) an optionally substituted pyridine ring;
the partial structure:

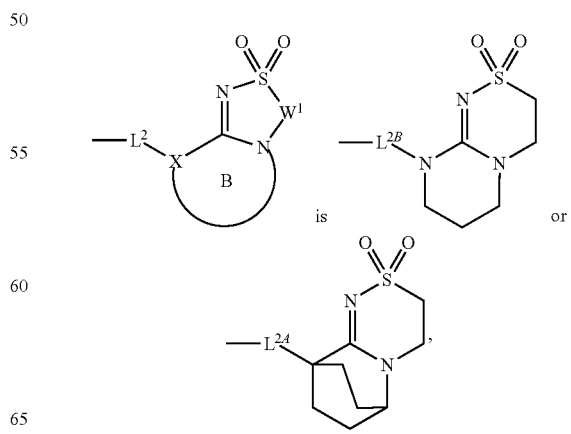

namely,
W¹, W², W³ and W⁴ are each ethylene (—CH₂—CH₂—);
R², R³ and R⁴ are each a hydrogen atom;
ethylene (—CH₂—CH₂—) for W², W³ or W⁴ is optionally substituted by 1 to 3 substituents selected from
(a) a halogen atom;
(b) hydroxy;
(c) $C_{1-5}$ alkyl optionally substituted by 1 to 3 halogen atoms;
(d) $C_{1-6}$ alkoxy; and
(e) $C_{1-5}$ alkyl-carbonyl;
$L^{2A}$ is a bond, —O— or —O—CH₂—; and
$L^{2B}$ is a bond or —CH₂—,
or a salt thereof.

[Compound (I-Q)]

Compound (I), compound (I-A), compound (I-B), compound (I-C), compound (I-F), compound (I-G), compound (I-H), compound (I-I), compound (I-J), compound (I-K), compound (I-L), compound (I-M), compound (I-O) or compound (I-P) wherein $R^1$ is
(1) $C_{1-6}$ alkyl optionally substituted by 1-5 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom, cyano, and $C_{1-6}$ alkyl optionally substituted by 1 to 3 halogen atoms;
(7) pyrimidinyl optionally substituted by 1 to 3 halogen atoms or cyano;
(8) isoxazolyl substituted by 1 to 3 $C_{1-6}$ alkyls;
(9) tetrahydrofuranyl;
(10) thienyl optionally substituted by 1 to 3 substituents selected from a halogen atom, cyano and $C_{1-6}$ alkyl;
(11) pyrazolyl optionally substituted by 1 to 3 substituents selected from a halogen atom, cyano, $C_{1-6}$ alkyl optionally substituted by 1 to 3 halogen atoms, and $C_{1-6}$ alkoxy;
(12) pyrrolidinonyl optionally substituted by 1 to 3 halogen atoms;
(13) tetrahydropyranyl; or
(14) dihydropyridazinonyl substituted by 1 to 3 $C_{1-6}$ alkyls;
$L^1$ is a bond, —O— or —CH₂—O—;
ring D is
(1) an optionally substituted benzene ring, or
(2) an optionally substituted pyridine ring;
the partial structure:

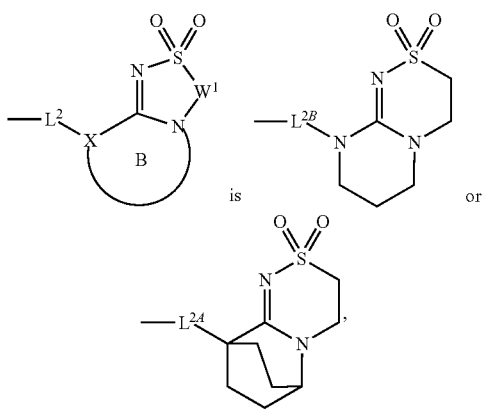

namely,
W¹, W², W³ and W⁴ are each ethylene (—CH₂CH₂—);
R², R³ and R⁴ are each a hydrogen atom;
ethylene (—CH₂—CH₂—) for W², W³ or W⁴ is optionally substituted by 1 to 3 $C_{1-6}$ alkyls optionally substituted by 1 to 3 halogen atoms;
$L^{2A}$ is a bond or —O—CH₂—; and
$L^{2B}$ is a bond,
or a salt thereof.

[Compound (I-R)]

Compound (I), compound (I-A), compound (I-B), compound (I-C), compound (I-F), compound (I-G), compound (I-H), compound (I-I), compound (I-J), compound (I-K), compound (I-L), compound (I-M), compound (I-O), compound (I-P) or compound (I-Q) wherein $R^1$ is
(1) phenyl optionally substituted by 1 to 3 substituents selected from a halogen atom, cyano, $C_{1-6}$ alkyl optionally substituted by 1 to 3 halogen atoms and $C_{1-6}$ alkoxy;
(2) benzodioxolyl substituted by 1 to 3 halogen atoms;
(3) pyridyl optionally substituted by 1 to 3 substituents selected from a halogen atom, cyano, and $C_{1-6}$ alkyl optionally substituted by 1 to 3 halogen atoms;
(4) thienyl optionally substituted by 1 to 3 substituents selected from a halogen atom, cyano and $C_{1-6}$ alkyl;
(5) pyrazolyl optionally substituted by 1 to 3 substituents selected from a halogen atom, cyano, $C_{1-6}$ alkyl optionally substituted by 1 to 3 halogen atoms, and $C_{1-6}$ alkoxy;
(6) pyrrolidinonyl optionally substituted by 1 to 3 halogen atoms;
(7) tetrahydropyranyl; or
(8) dihydropyridazinonyl substituted by 1 to 3 $C_{1-6}$ alkyls;
$L^1$ is a bond or —O—;
ring D is
(1) an optionally substituted benzene ring, or
(2) an optionally substituted pyridine ring;
the partial structure:

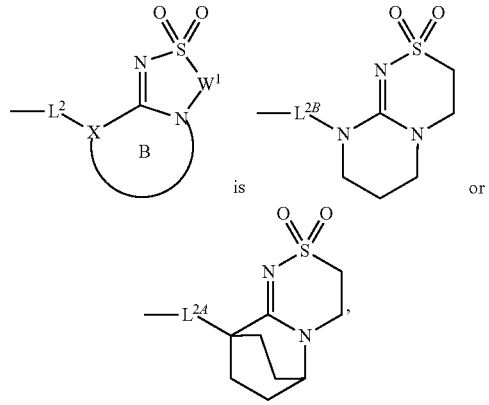

namely,
W¹, W², W³ and W⁴ are each ethylene (—CH₂CH₂—);
R², R³ and R⁴ are each a hydrogen atom;
ethylene (—CH₂—CH₂—) for W², W³ or W⁴ is optionally substituted by 1 to 3 $C_{1-6}$ alkyls optionally substituted by 1 to 3 halogen atoms;
$L^{2A}$ is a bond or —O—CH₂—; and
$L^{2B}$ is a bond,
or a salt thereof.

Specific examples of compound (I) are Example compounds. Among these, 9-(4-(4-chlorophenoxyl)phenyl)-3,4,6,7,8,9-hexahydro-6,9-ethanopyrido[2,1-c][1,2,4]thiadiazine 2,2-dioxide or a salt thereof (Example 1);

9-(4-(4-chlorophenoxyl)phenyl)-3,4,6,7,8,9-hexahydropyrimido[2,1-c][1,2,4]thiadiazine 2,2-dioxide or a salt thereof (Example 45); or 9-(4-((6-(trifluoromethyl)pyridin-2-yl)oxy)phenyl)-3,4,6,7,8,9-hexahydro-6,9-ethanopyrido[2,1-c][1,2,4]thiadiazine 2,2-dioxide or a salt thereof (Example 69);

is preferable.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmaceutically acceptable are preferable. For example, in the case when acidic functional group are present in the compound, for example, inorganic salts including alkali metal salts (e.g., sodium salts, potassium salt, etc.) and alkali earth metal salts (e.g., calcium salts, magnesium salts, barium salts, etc.) and ammonium salts are preferable. In the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (I) includes isomers such as tautomers, optical isomers, stereoisomers, position isomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method.

The compound (I) may be a solvate (e.g., hydrate) or a non-solvate and both are included in the compound (I).

Compounds labeled with or substituted by isotopes (e.g., $^2$H, $^3$H, $^{11}$C, $^{14}$C, $^{18}$F, $^{35}$S, $^{125}$I, etc.) are also included in compound (I). Compound (I) labeled with or substituted by isotopes can be used as, for example, a tracer used for Positron Emission Tomography (PET) (PET tracer), and are useful in the field of medical diagnosis and the like.

The production methods of the compound (I) or a salt thereof of the present invention are explained below.

The compound (I) of the present invention can be obtained by, for example, the methods shown by the following reaction schemes or a method analogous thereto, and the like. In the following, each symbol relating to the compounds in the schematic drawings of the reaction schemes is as defined above, unless particularly indicated. The compounds in the reaction schemes also include salts, and examples of the salt include those similar to compound (I) and the like.

The product resulting from each step in the form of a reaction mixture or a crude product can also be used for the next reaction, or can be isolated from the reaction mixture according to a conventional method and easily purified by a separation means such as recrystallization, distillation, chromatography, and the like.

The reagents and reactants used for each reaction may be an easily available commercially product, or can also be produced by a method known per se, or a method analogous thereto, or the methods described in the Examples. For example, the reagents and reactants described in the Examples can be used.

Unless particularly indicated, the solvent used in each reaction is not particularly limited as long as the reaction proceeds, and the reaction may be performed in a solvent inert to the reaction, or without solvent, where two or more kinds of solvents may be used by mixing them at an appropriate ratio. For example, the solvents described in the Examples can be used.

Unless particularly indicated, the equivalents of the reagents and reactants used for each reaction is 0.001 equivalent-100 equivalents relative to the substrate of each reaction. For example, the equivalents of the reagents and reactants described in the Examples can be used.

Unless particularly indicated, the reaction time of each reaction is generally 5 min-72 hr. For example, the reaction time described in the Examples can be employed.

Unless particularly indicated, the reaction temperature of each reaction is from −78° C. to 300° C. For example, the reaction can be performed at a reaction temperature described in the Examples.

In the following Reaction Schemes, halogenation reaction, acylation reaction, sulfonylation reaction, alkylation reaction, hydrolysis reaction, amination reaction, amidation reaction, esterification reaction, etherification reaction, oxidation reaction, reduction reaction and the like are carried out according to a method known per se. Examples of the method include the methods described in ORGANIC FUNCTIONAL GROUP PREPARATIONS, 2nd edition, Academic Press Inc., 1989, or Comprehensive Organic Transformations: A Guide to Functional Group Preparations, 2nd edition, Wiley-VCH, 1999, ShinJikken Kagaku Kouza (Courses in Experimental Chemistry) (The Chemical Society of Japan ed.), Jikken Kagaku Kouza (The Chemical Society of Japan ed.) and the like, and the like.

In the following Reaction Schemes, when the starting compound has an amino group, a carboxy group, a hydroxy group, a carbonyl group or a sulfanyl group, a protecting group generally used in the peptide chemistry etc. may be introduced into these functional groups, and the object compound can be obtained by removing the protecting group as necessary after the reaction. A reaction to introduce a protecting group into these functional groups is indicated as "protection reaction" and a reaction to remove the protecting group is indicated as "deprotection reaction". The introduction method of a protecting group (protection reaction) and a removal method of a protecting group (deprotection reaction) can be a method known per se, for example, the method described in Greene's PROTECTIVE GROUPS in ORGANIC SYNTHESIS, 4th Edition, Wiley-Interscience, 2006, or the like, or the method described in the Examples or the like.

When desired, this reaction can also be carried out under microwave irradiation by using a microwave irradiation apparatus (e.g., INITIATOR manufactured by Biotage, etc.).

Compound (I) can be produced as described in, for example, the following reaction scheme 1, by reacting compound (IIa) with compound (IIIa), or compound (IIa) with compound (IIIb).

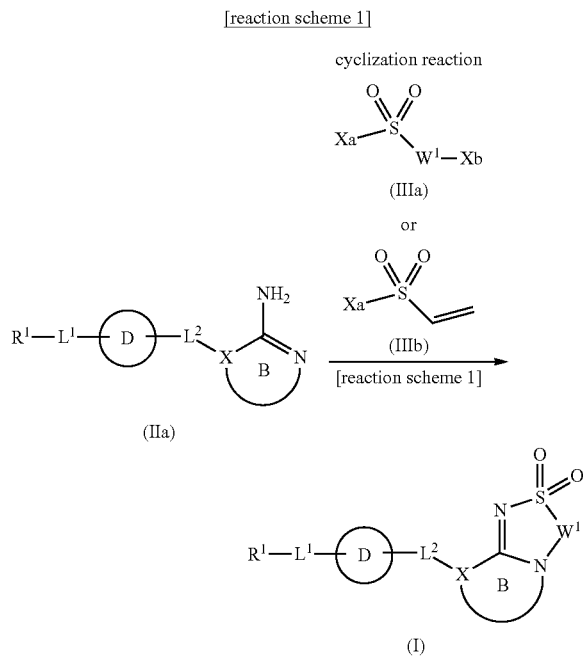

wherein Xa and Xb are leaving groups, and other symbols are as defined above.

Examples of the "leaving group" for Xa or Xb include optionally substituted acyloxy groups (e.g., acetyloxy, benzoyloxy etc.), halogen atoms (e.g., fluorine, chlorine, bromine, iodine etc.), optionally halogenated $C_{1-6}$ alkylsulfonyloxy (e.g., methanesulfonyloxy, ethanesulfonyloxy, trichloromethanesulfonyloxy, trifluoromethanesulfonyloxy [triflate] etc.), optionally substituted $C_{6-14}$ arylsulfonyloxy and the like. Examples of the "optionally substituted $C_{6-14}$ arylsulfonyloxy" include $C_{6-14}$ arylsulfonyloxy optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.), nitro, and the like. Specific examples thereof include benzenesulfonyloxy, m-nitrobenzenesulfonyloxy, p-toluenesulfonyloxy, naphthylsulfonyloxy and the like.

The amount of compound (IIIa) or compound (IIIb) to be used is about 0.1 to 50 mol, preferably 0.8 to 10 mol, per 1 mol of compound (IIa).

This reaction may be performed in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IIa).

It is advantageous to perform the reaction without solvent or in a solvent inert to the reaction. The solvent is not particularly limited as long as the reaction proceeds, and the preferable example thereof include ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

Compound (I) can be produced as described in, for example, the following reaction scheme 2, by intramolecular cyclization of compound (IIb).

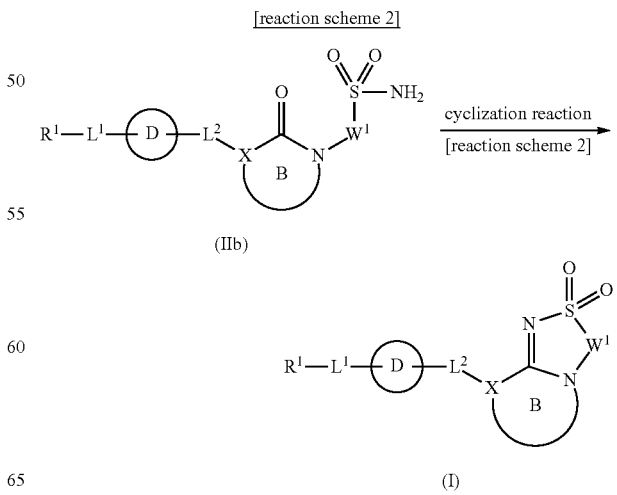

This reaction is performed in the co-presence of halogenated phosphoryls such as phosphorus oxychloride, phosphorus oxybromide and the like, arylphosphinic chlorides such as diphenylphosphinic chloride and the like, and the like.

The amount of the "halogenated phosphoryls and arylphosphinic chlorides" to be used is 0.1- to 300-fold, preferably 1- to 30-fold, in weight ratio relative to compound (IIb), or about 0.1 to 500 mol, preferably 1 to 100 mol, per 1 mol of compound (IIb).

It is advantageous to perform the reaction without solvent or in a solvent inert to the reaction. The solvent is not particularly limited as long as the reaction proceeds, and preferable example thereof include hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

Compound (I) can be produced as described in, for example, the following reaction scheme 3, by reacting compound (IIc) with compound (IIIc).

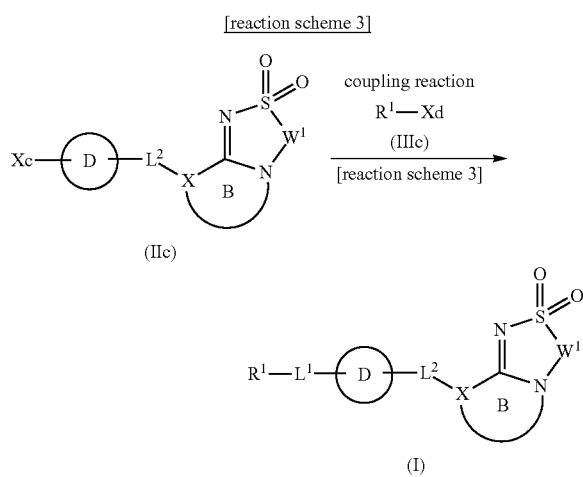

wherein Xc and Xd are leaving groups or functional groups, and other symbols are as defined above.

Examples of the "leaving group" for Xc or Xd include hydrogen, optionally substituted acyloxy group (e.g., acetyloxy, benzoyloxy etc.), a halogen atom (e.g., fluorine, chlorine, bromine, iodine etc.), an optionally halogenated $C_{1-6}$ alkylsulfonyloxy (e.g., methanesulfonyloxy, ethanesulfonyloxy, trichloromethanesulfonyloxy, trifluoromethanesulfonyloxy [triflate] etc.), a boronyl group, an optionally substituted $C_{1-6}$ alkylboranyl group, an optionally substituted $C_{2-6}$ alkenylboranyl group, an optionally substituted $C_{1-6}$ alkoxyboranyl group, an optionally substituted $C_{6-14}$ arylboranyl group, an optionally substituted $C_{1-6}$ alkylstannyl group (e.g., tributylstannyl and the like), an optionally substituted $C_{2-6}$ alkenylstannyl group, an optionally substituted $C_{6-14}$ arylstannyl group, a metal-containing substituent (e.g., magnesium halide, zinc halide etc.), an optionally substituted $C_{6-14}$ arylsulfonyloxy and the like. Examples of the "optionally substituted $C_{6-14}$ arylsulfonyloxy" include $C_{6-14}$ arylsulfonyloxy optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.) and nitro, and the like, and specific examples thereof include, benzenesulfonyloxy, m-nitrobenzenesulfonyloxy, p-toluenesulfonyloxy, naphthylsulfonyloxy and the like.

Examples of the "functional group" for Xc or Xd include hydroxy group, hydroxymethyl group, hydroxyethyl group, alkyl halide group (e.g., chloromethyl, chloroethyl, bromomethyl etc.), optionally halogenated $C_{1-6}$ alkylsulfonyloxyalkyl group (e.g., methanesulfonyloxymethyl, ethanesulfonyloxymethyl, trichloromethanesulfonyloxymethyl, trifluoromethanesulfonyloxy[triflate]methyl etc.) and the like can be mentioned.

The amount of compound (IIIc) to be used is about 0.1 to 30 mol, preferably 0.8 to 10 mol, per 1 mol of compound (IIc).

This reaction may be carried out in the presence of a base, a desiccant, an additive and a metal catalyst, as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IIc).

Examples of the "desiccant" include molecular sieves such as molecular sieves 4A, molecular sieves 3A and the like, inorganic salts such as anhydrous sodium sulfates, anhydrous magnesium sulfate and the like, and the like.

The amount of the "desiccant" to be used is about 0.1- to 500-fold weight, preferably 0.1- to 30-fold weight, relative to compound (IIc).

Examples of the "additive" include cyclohexyl-1,2-diamine, N,N'-dimethylcyclohexyl-1,2-diamine, picolinic acid and the like.

The amount of the "additive" to be used is about 0.01 to 30 mol, preferably 0.01 to 10 mol, per 1 mol of compound (IIc).

Examples of the "metal catalyst" include a complex composed of a metal (e.g., nickel, palladium, copper etc.) and a ligand, and the like. Examples of the complex composed of a metal and a ligand include tetrakis(triphenylphosphine)palladium(0), bis(triphenylphosphine)palladium(II) dichloride, tris(dibenzylideneacetone)dipalladium(0), trans-dichlorobis(tri-o-tolylphosphine)palladium(II), palladium (II) trifluoroacetate, palladium(II) acetate, nickel(II) acetylacetonate, nickel chloride 1,2-bis(diphenylphosphino)

ethane complex, copper iodide, copper bromide, copper chloride, copper acetate and the like. In addition, examples of the ligand include an acyloxy group (e.g., acetyloxy, benzoyloxy etc.), a halogen atom (e.g., fluorine, chlorine, bromine, iodine etc.), triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',-4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like.

The amount of the "metal catalyst" to be used is generally about 0.01 to 1000 wt %, preferably about 1 to 20 wt %, relative to compound (IIc).

When desired, this reaction can also be carried out under microwave irradiation by using a microwave irradiation apparatus (e.g., INITIATOR manufactured by Biotage, etc.).

This reaction is advantageously carried out without solvent or in a solvent inert to reaction. The solvent is not particularly limited as long as the reaction proceeds, and preferable example thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably about 0 to 180° C. The reaction time is generally about 5 min to 72 hr, preferably about 5 min to 24 hr.

This reaction may be carried out under an atmosphere of, for example, nitrogen, argon and the like, as necessary.

Compound (I) can be produced as described in, for example, the following reaction scheme 4, by reacting compound (IId) with compound (IIId).

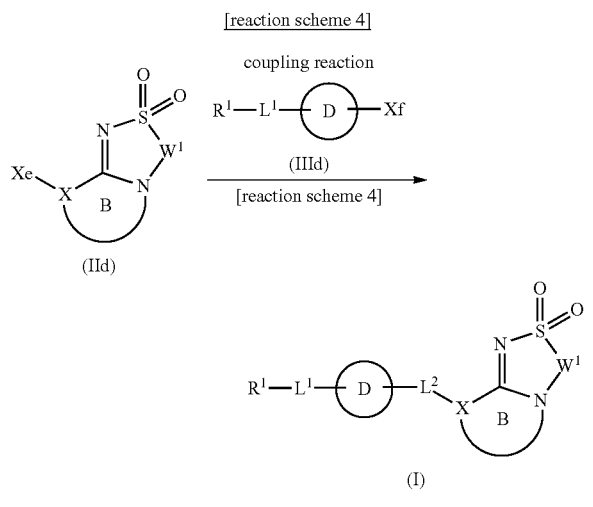

wherein Xe and Xf are leaving groups or functional groups, and other symbols are as defined above.

Examples of the "leaving group" for Xe or Xf include optionally substituted acyloxy groups (e.g., acetyloxy, benzoyloxy etc.), halogen atoms (e.g., fluorine, chlorine, bromine, iodine etc.), optionally halogenated $C_{1-6}$ alkylsulfonyloxy (e.g., methanesulfonyloxy, ethanesulfonyloxy, trichloromethanesulfonyloxy, trifluoromethanesulfonyloxy [triflate] etc.), optionally substituted $C_{6-14}$ arylsulfonyloxy and the like. Examples of the "optionally substituted $C_{6-14}$ arylsulfonyloxy" include $C_{6-14}$ arylsulfonyloxy optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.) and nitro, and the like. Specific examples thereof include benzenesulfonyloxy, m-nitrobenzenesulfonyloxy, p-toluenesulfonyloxy, naphthylsulfonyloxy and the like.

Examples of the "functional group" for Xe or Xf include hydroxy group, hydroxymethyl group, hydroxyethyl group, alkyl halide groups (e.g., chloromethyl, chloroethyl, bromomethyl etc.), optionally halogenated $C_{1-6}$ alkylsulfonyloxyalkyl groups (e.g., methanesulfonyloxymethyl, ethanesulfonyloxymethyl, trichloromethanesulfonyloxymethyl, trifluoromethanesulfonyloxy[triflate]methyl etc.) and the like.

The amount of compound (IIId) to be used is about 0.1 to 30 mol, preferably 0.8 to 10 mol, per 1 mol of compound (IId).

This reaction may be performed in the co-presence of a base and a hydroxy group activator as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IId).

Examples of the "hydroxy group activator" include cyanomethylenetri-n-butylphosphorane, diisopropyl azodicarboxylate and triphenylphosphine, diethyl azodicarboxylate and triphenylphosphine, 1,1'-(azodicarbonyl)dipiperidine and tributylphosphine and the like.

The amount of the "hydroxy group activator" to be used is about 0.1 to 30 mol, preferably 0.8 to 10 mol, per 1 mol of compound (IId).

When desired, this reaction can also be performed under microwave irradiation using a microwave irradiation apparatus (for example, INITIATOR manufactured by Biotage etc.).

It is advantageous to perform the reaction without solvent or in a solvent inert to the reaction. The solvent is not particularly limited as long as the reaction proceeds, and preferable example thereof include ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably about 0 to 180° C. The reaction time is generally about 5 min to 72 hr, preferably about 5 min to 24 hr.

This reaction may also be performed under an atmosphere of nitrogen, argon and the like as necessary.

Compound (IIa) can be produced by the method described in, for example, the following reaction scheme 5. That is, compound (IVa) and compound (V) are reacted to synthesize compound (IVb), an intramolecular cyclization reaction of compound (IVb) is performed in the presence of a base to induce compound (IVc), and compound (IVd) is synthesized using a sulfurizing reagent. Subsequently, an alkylating reagent is used to induce compound (IVe), which is subjected to an amination reaction to give compound (IIa).

[reaction scheme 5]

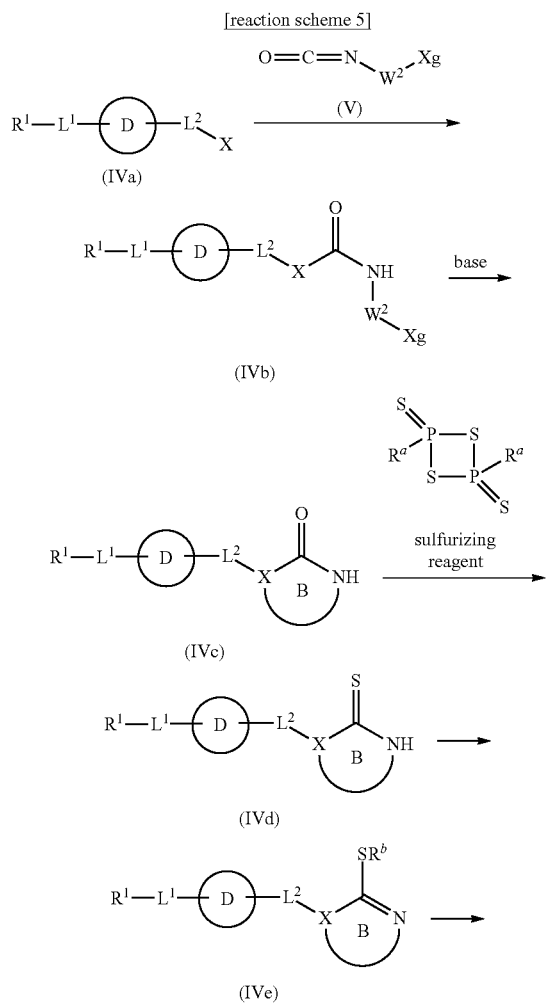

-continued

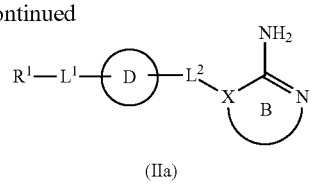

(IIa)

wherein Xg is a leaving group, $R^a$ and $R^b$ are functional groups, and other symbols are as defined above.

Examples of the "leaving group" for Xg include optionally substituted acyloxy groups (e.g., acetyloxy, benzoyloxy etc.), halogen atoms (e.g., fluorine, chlorine, bromine, iodine etc.), optionally halogenated $C_{1-6}$ alkylsulfonyloxy (e.g., methanesulfonyloxy, ethanesulfonyloxy, trichloromethanesulfonyloxy, trifluoromethanesulfonyloxy[triflate] etc.), optionally substituted $C_{6-14}$ arylsulfonyloxy and the like.

Examples of the "functional group" for $R^a$ include optionally substituted $C_{6-14}$ aryl groups (e.g., phenyl group, 4-methoxyphenyl group, 4-phenoxyphenyl group and the like), $C_{1-6}$ alkyl groups (e.g., methyl group, ethyl group, isopropyl group), benzyl group and the like.

Examples of the "functional group" for $R^b$ include $C_{1-6}$ alkyl groups (e.g., methyl group, ethyl group, propyl group, isopropyl group etc.) and the like.

Compounds (IVa) and (V) are easily obtainable as commercially available products, or can also be produced by the methods known per se described in known documents including ShinJikken Kagaku Koza (Courses in Experimental Chemistry) (The Chemical Society of Japan ed.), Jikken Kagaku Kouza (The Chemical Society of Japan ed.), and the like, or a method analogous thereto.

The amount of compound (V) to be used is about 0.1 to 30 mol, preferably 0.8 to 10 mol, per 1 mol of compound (IVa).

The reaction of compound (IVa) and compound (V) may be performed in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVa).

It is advantageous to perform the reaction without solvent or in a solvent inert to the reaction. The solvent is not particularly limited as long as the reaction proceeds, and preferable example thereof include ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IVc) from compound (IVb) advantageously proceeds in the co-presence of a base.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVb).

It is advantageous to perform the reaction without solvent or in a solvent inert to the reaction. The solvent is not particularly limited as long as the reaction proceeds, and preferable example thereof include ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IVd) from compound (IVc) advantageously proceeds in the co-presence of a sulfurizing reagent.

Examples of the "sulfurizing reagent" include Lawesson reagent (2,4-bis(4-methoxyphenyl)-1,3,2,4-dithiadiphosphetane 2,4-disulfide), Davy's reagent (2,4-dimethyl-1,3,2,4-dithiadiphosphetane 2,4-disulfide, 2,4-diethyl-1,3,2,4-dithiadiphosphetane 2,4-disulfide, 2,4-diisopropyl-1,3,2,4-dithiadiphosphetane 2,4-disulfide, 2,4-dibenzyl-1,3,2,4-dithiadiphosphetane 2,4-disulfide), Japanese reagent (2,4-diphenyl-1,3,2,4-dithiadiphosphetane 2,4-disulfide), Belleau's reagent (2,4-bis(4-phenoxyphenyl)-1,3,2,4-dithiadiphosphetane 2,4-disulfide) and the like.

The amount of the "sulfurizing reagent" to be used is about 0.1 to 100 mol, preferably 0.8 to 10 mol, per 1 mol of compound (IVc).

It is advantageous to perform the reaction without solvent or in a solvent inert to the reaction. The solvent is not particularly limited as long as the reaction proceeds, and preferable example thereof include ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IVe) from compound (IVd) advantageously proceeds in the co-presence of an alkylating reagent.

Examples of the "alkylating reagent" include methyl iodide, ethyl iodide, benzyl bromide and the like.

The amount of the "alkylating reagent" to be used is about 0.1 to 100 mol, preferably 0.8 to 10 mol, per 1 mol of compound (IVd).

It is advantageous to perform the reaction without solvent or in a solvent inert to the reaction. The solvent is not particularly limited as long as the reaction proceeds, and preferable example thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The amination reaction to synthesize compound (IIa) from compound (IVe) advantageously proceeds in the co-presence of an aminating reagent and, where necessary, a base.

Examples of the "aminating reagent" include aqueous ammonia, ammonia, inorganic ammonium salt (e.g., ammonium acetate, ammonium carbonate etc.), and urea.

The amount of the "aminating reagent" to be used is 0.1 to 10000 in weight ratio relative to compound (IVe), or about 0.1 to 500 mol, preferably 0.8 to 100 mol, per 1 mol of compound (IVe).

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVe).

It is advantageous to perform the reaction without solvent or in a solvent inert to the reaction. The solvent is not particularly limited as long as the reaction proceeds, and preferable example thereof include ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

Compound (IIb) can be produced by the method described in, for example, the following reaction scheme 6. That is, for example, compound (IVg) synthesized by reacting compound (IVf) with acrylates (e.g., $C_{1-6}$ alkyl ester of acrylic acid such as methyl acrylate, ethyl acrylate and the like) in the presence of a base shown in Example 1, heating or hydrolyzing same in lithium chloride and DMSO, followed by a decarboxylation reaction, or compound (IVg) synthesized by a combination of methods known per se, which are described in ORGANIC FUNCTIONAL GROUP PREPARATIONS, 2nd edition, Academic Press Inc., 1989 or Comprehensive Organic Transformations: A Guide to Functional Group Preparations, 2nd edition, Wiley-VCH, 1999, Shin-Jikken Kagaku Koza (edited by the Chemical Society of Japan), Jikken Kagaku Koza (edited by the Chemical Society of Japan) or the like (e.g., alkylation reaction, hydrolysis reaction, amination reaction, amidation reaction, esterification reaction, etherification reaction, oxidation reaction, reduction reaction, cyclization reaction, coupling reaction, the aforementioned protection reaction, deprotection reaction etc.) is reacted with compound (VI) to synthesize compound (IVh). Subsequently, an intramolecular cyclization reaction of compound (IVh) is performed, for example, under heating conditions to convert same to compound (IVi) and, where necessary, a conversion reaction of functional group Y is performed by a combination of methods known per se, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction and the like, followed by a coupling reaction of compound (IVi) and compound (IIIc) to give compound (IIb).

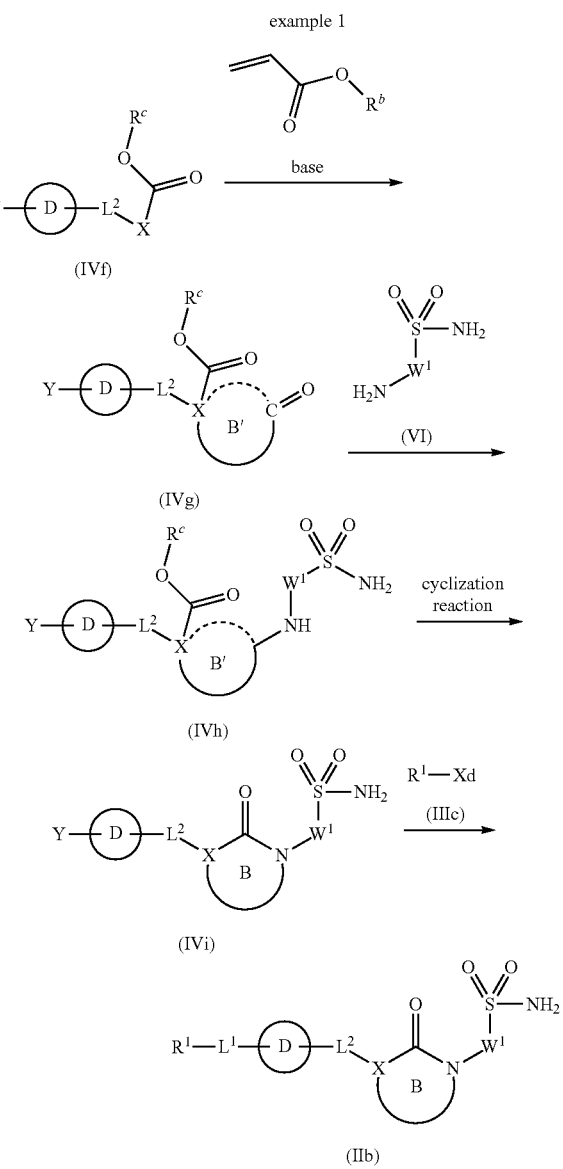

[reaction scheme 6]

wherein Y is a leaving group or functional group, $R^c$ is a functional group, B' is a 5- to 8-membered ring group cyclized at a part shown with a broken line, which optionally has 1 to 3 hetero atoms selected from a nitrogen atom and an oxygen atom and is optionally substituted, or optionally substituted formyl $C_{1-3}$ alkyl group, or optionally substituted formyl $C_{2-3}$ alkenyl group, and other symbols are as defined above.

Examples of the "leaving group" for Y include optionally substituted acyloxy groups (e.g., acetyloxy, benzoyloxy etc.), halogen atoms (e.g., fluorine, chlorine, bromine, iodine etc.), optionally halogenated $C_{1-6}$ alkylsulfonyloxy (e.g., methanesulfonyloxy, ethanesulfonyloxy, trichloromethanesulfonyloxy, trifluoromethanesulfonyloxy[triflate] etc.), optionally substituted $C_{6-14}$ arylsulfonyloxy and the like.

Examples of the "functional group" for Y include $C_{1-6}$ alkoxy groups (e.g., methoxy group, ethoxy group, isopropoxy group etc.), optionally substituted benzyloxy group, acyloxy groups (e.g., acetyloxy, benzoyloxy etc.), halogen atoms (e.g., fluorine, chlorine, bromine, iodine etc.), optionally halogenated $C_{1-6}$ alkylsulfonyloxy (e.g., methanesulfonyloxy, ethanesulfonyloxy, trichloromethanesulfonyloxy, trifluoromethanesulfonyloxy[triflate] etc.), optionally substituted $C_{6-14}$ arylsulfonyloxy, $C_{1-6}$ alkyloxycarbonyl groups (e.g., methoxycarbonyl group, ethoxycarbonyl group, isopropoxycarbonyl group etc.), carboxyl group, hydroxy group, hydroxymethyl group, hydroxyethyl group, alkyl halide groups (e.g., chloromethyl, chloroethyl, bromomethyl etc.), optionally halogenated $C_{1-6}$ alkylsulfonyloxyalkyl groups (e.g., methanesulfonyloxymethyl, ethanesulfonyloxymethyl, trichloromethanesulfonyloxymethyl, trifluoromethanesulfonyloxy[triflate]methyl etc.), optionally substituted $C_{6-14}$ aralkyloxyalkyl groups (e.g., benzyloxymethyl group, 4-methoxybenzyloxymethyl group and the like), formyl group and the like.

Examples of the "functional group" for $R^c$ include optionally substituted $C_{6-14}$ aryl groups (e.g., phenyl group, 4-methoxyphenyl group, 4-phenoxyphenyl group and the like), $C_{1-6}$ alkyl groups (e.g., methyl group, ethyl group, isopropyl group) or benzyl group and the like.

Examples of the "optionally substituted 5- to 8-membered ring group optionally having 1 to 3 hetero atoms selected from a nitrogen atom and an oxygen atom" for B' include optionally substituted $C_{5-8}$ cycloalkyl groups (e.g., cyclopentyl group, cyclohexyl group and the like) and the like.

Examples of the "optionally substituted formyl $C_{1-3}$ alkyl group or optionally substituted formyl $C_{2-3}$ alkenyl group" for B' include optionally substituted formylmethyl group, formylethyl group, formylpropyl group, formylethynyl group, formylpropenyl group and the like.

Compounds (IVf) and (VI) are easily obtainable as commercially available products, or can also be produced by the methods known per se described in known documents including ShinJikken Kagaku Koza (Courses in Experimental Chemistry) (The Chemical Society of Japan ed.), Jikken Kagaku Kouza (The Chemical Society of Japan ed.), and the like, or a method analogous thereto.

The reaction of compound (IVf) with acrylate (e.g., $C_{1-6}$ alkyl ester of acrylic acid such as methyl acrylate, ethyl acrylate and the like) advantageously proceeds in the co-presence of a base.

Examples of the "base" include inorganic bases such as sodium hydroxide, barium hydroxide, potassium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVf).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

After the reaction of compound (IVf) and acrylate, the mixture is heated in the presence of an inorganic salt to synthesize compound (IVg).

Examples of the "inorganic salt" include lithium chloride and the like can be mentioned.

The amount of the "inorganic salt" to be used is about 0.01 to 30 mol, preferably 0.1 to 10 mol, per 1 mol of compound (IVf).

This reaction is advantageously carried out without solvent or in a solvent inert to the reaction. The solvent is not particularly limited as long as the reaction proceeds, and preferable examples thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane, cyclopentyl methyl ether and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about 30 to 250° C., preferably 50 to 180° C. Where necessary, a temperature not less than or not more than that can be selected. The reaction time is generally about 5 min to 72 hr, preferably about 5 min to 24 hr. Where necessary, a time not less than or not more than that can be selected.

Alternatively, after the reaction of compound (IVf) and acrylates, a hydrolysis reaction is performed using a base, and a decarboxylation reaction is performed to synthesize compound (IVg).

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVf).

This reaction is advantageously carried out in a solvent inert to the reaction. The solvent is not particularly limited as long as the reaction proceeds, and preferable examples thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about 0 to 300° C., preferably 60 to 230° C. Where necessary, a temperature not less than or not more than that can be selected. The reaction time is generally about 5 min to 72 hr, preferably about 5 min to 24 hr. Where necessary, a time not less than or not more than that can be selected.

The reductive amination reaction to synthesize compound (IVh) from compound (IVg) and compound (VI) advantageously proceeds in the co-presence of a reducing agent and, where necessary, an additive.

The amount of compound (VI) to be used is about 0.1 to 30 mol, preferably 0.8 to 10 mol, per 1 mol of compound (IVg).

Examples of the "reducing agent" include sodium triacetoxyborohydride, sodium cyanoborohydride, 2-picoline-borane and the like.

The amount of the "reducing agent" to be used is about 0.1 to 30 mol, preferably 0.8 to 10 mol, per 1 mol of compound (IVg).

Examples of the "additive" include organic acids such as formic acid, acetic acid, propionic acid and the like, and the like.

The amount of the "additive" to be used is about 0.1 to 30 mol, preferably 0.8 to 10 mol, per 1 mol of compound (IVg).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IVi) from compound (IVh) advantageously proceeds heating conditions in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVh).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic m hydrocarbons such as pyridine, lutidine, quinoline and the like; water and the like, a mixed solvent thereof and the like.

The reaction temperature is about 0 to 300° C., preferably 60 to 230° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IIb) from compound (IVi) and compound (IIIc) may be performed in the co-presence of a base, a desiccant, an additive and a metal catalyst as necessary.

The amount of compound (IIIc) to be used is about 0.1 to 30 mol, preferably 0.8 to 10 mol, per 1 mol of compound (IVi).

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVi).

Examples of the "desiccant" include molecular sieves such as molecular sieves 4A, molecular sieves 3A and the like, inorganic salts such as anhydrous sodium sulfate, anhydrous magnesium sulfate and the like, and the like.

The amount of the "desiccant" to be used is about 0.1- to 500-fold, preferably 0.1- to 3 0-fold, in weight ratio relative to compound (IVi).

Examples of the "additive" include cyclohexyl-1,2-diamine, N,N'-dimethylcyclohexyl-1,2-diamine, picolinic acid and the like.

The amount of the "additive" to be used is about 0.01 to 30 mol, preferably 0.01 to 10 mol, per 1 mol of compound (IVi).

Examples of the "metal catalyst" include a complex composed of a metal such as nickel, palladium, copper and the like, and a ligand, and the like. Examples of the complex composed of a metal and a ligand include tetrakis(triphenylphosphine)palladium(0), bis(triphenylphosphine)palladium(II)dichloride, tris(dibenzylideneacetone)dipalladium(0), trans-dichlorobis(tri-o-tolylphosphine)palladium(II), palladium(II) trifluoroacetate, palladium(II) acetate, nickel(II) acetylacetonate, nickel chloride 1,2-bis(diphenylphosphino)ethane complex, copper iodide, copper bromide, copper chloride, copper acetate and the like, and examples of the ligand include acyloxy groups (e.g., acetyloxy, benzoyloxy etc.), halogen atoms (e.g., fluorine, chlorine, bromine, iodine etc.), triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like.

The amount of the "metal catalyst" to be used is generally about 0.01 to 1000 wt %, preferably about 1 to 20 wt %, relative to compound (IVi).

When desired, this reaction can also be carried out under microwave irradiation by using a microwave irradiation apparatus (e.g., INITIATOR manufactured by Biotage, etc.).

This reaction is advantageously carried out without solvent or in a solvent inert to the reaction. The solvent is not particularly limited as long as the reaction proceeds, and preferable examples thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably about 0 to 180° C. The reaction time is generally about 5 min to 72 hr, preferably about 5 min to 24 hr.

This reaction may be carried out under an atmosphere of, for example, nitrogen, argon and the like, as necessary.

Compound (IIc) can be produced by the method described in, for example, the following reaction scheme 7. That is, an intramolecular cyclization reaction of compound (IVi) is performed and, where necessary, a conversion reaction of functional group Y is performed by a combination of methods known per se, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction and the like to give compound (IIc).

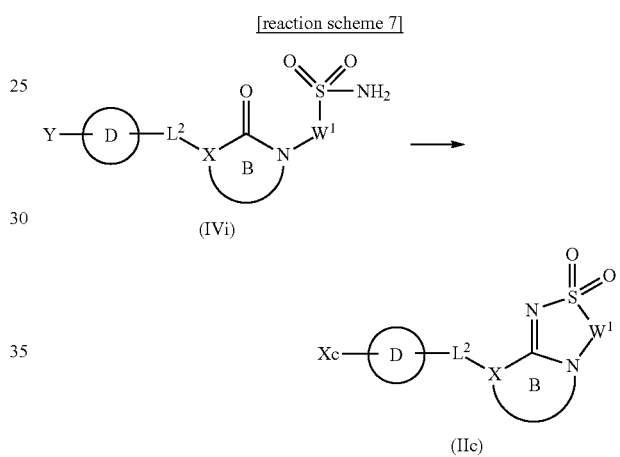

[reaction scheme 7]

wherein the symbols are as defined above.

This reaction is performed in the co-presence of halogenated phosphoryls such as phosphorus oxychloride, phosphorus oxybromide and the like, arylphosphinic chlorides such as diphenylphosphinic chloride and the like, and the like.

The amount of the "halogenated phosphoryls and arylphosphinic chlorides" to be used is 0.1- to 300-fold, preferably 1- to 30-fold, in weight ratio relative to compound (IVi), or about 0.1 to 500 mol, preferably 1 to 100 mol, per 1 mol of compound (IVi).

This reaction is advantageously carried out without solvent or in a solvent inert to the reaction. The solvent is not particularly limited as long as the reaction proceeds, and preferable examples thereof include hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

Compound (IId) can be produced by the method described in, for example, the following reaction scheme 8. That is, compound (IVj) described in method 1 and compound (VI) are reacted to synthesize compound (IVk). Alternatively, compound (IVj) described in method 2 is converted to an amine derivative by an amination reaction, and reacted with compound (VII) known per se in the presence of a base, and a deprotection reaction is performed using an acid to synthesize compound (IVk) ($W^1$ is ethylene (—$CH_2$—$CH_2$—)). Subsequently, an intramolecular cyclization reaction of compound (IVk) is performed, for example, under heating conditions to induce compound (IVl) and, where necessary, a conversion reaction of functional group Y is performed by a combination of methods known per se, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction and the like. Subsequently, an intramolecular cyclization reaction of compound (IVl) is performed and, where necessary, a conversion reaction of functional group Y is performed by a combination of methods known per se, for example, halogenation reaction, acylation reaction, sulfonylation reaction, alkylation reaction, hydrolysis reaction, amination reaction, amidation reaction, esterification reaction, etherification reaction, oxidation reaction, reduction reaction, protection reaction, deprotection reaction, coupling reaction and the like to give compound (IId).

Compound (IVl) can be produced by the method described in, for example, method 3 of the following reaction scheme 8. That is, compound (IVj) and compound (VIII) are reacted to synthesize compound (IVm). Subsequently, an intramolecular cyclization reaction of compound (IVm) is performed, for example, under heating conditions to induce compound (IVn), which is subjected to a deprotection reaction using an acid to synthesize compound (IVl).

[reaction scheme 8]

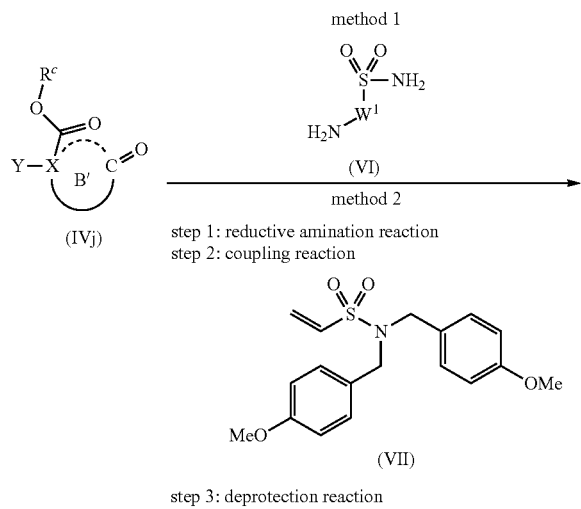

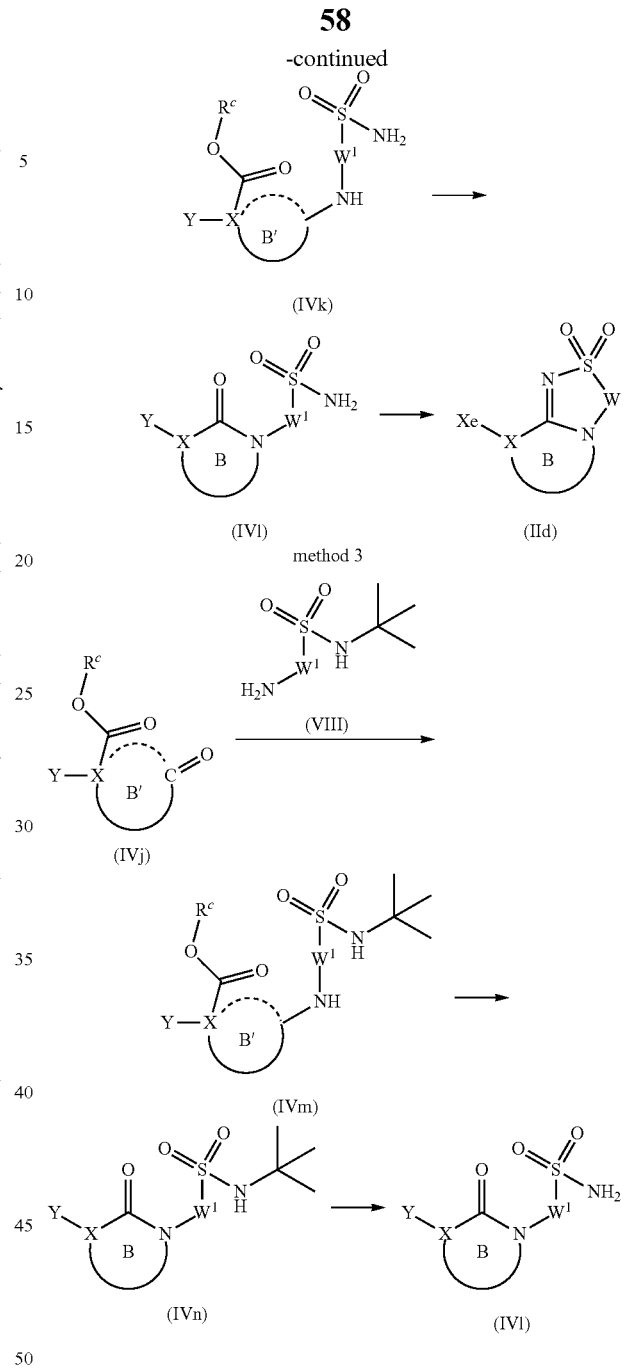

wherein the symbols are as defined above.

Compound (IVj) can also be produced by the methods known per se described in known documents including Synthetic Communications, vol. 14, pages 401-406 (1984) or Tetrahedron, vol. 3, page 175 (1958) or Journal of Organic Chemistry, vol. 20, 1702-1707 (1955) or ShinJikken Kagaku Koza (Courses in Experimental Chemistry) (The Chemical Society of Japan ed.), Jikken Kagaku Kouza (The Chemical Society of Japan ed.) and the like, or a method analogous thereto.

compound (VII) can also be produced by the methods known per se described in known documents including Journal of Organic Chemistry, vol. 56, 3549-3556 (1991) or WO 2009/11851 or ShinJikken Kagaku Koza (Courses in Experimental Chemistry) (The Chemical Society of Japan ed.), Jikken Kagaku Kouza (The Chemical Society of Japan ed.) and the like or a method analogous thereto.

The reductive amination reaction of (method 1) to synthesize compound (IVk) from compound (IVj) and compound (VI) advantageously proceeds in the co-presence of a reducing agent and, where necessary, an additive.

The amount of compound (VI) to be used is about 0.1 to 30 mol, preferably 0.8 to 10 mol, per 1 mol of compound (IVj).

Examples of the "reducing agent" include sodium triacetoxyborohydride, sodium cyanoborohydride, 2-picolineborane and the like.

The amount of the "reducing agent" to be used is about 0.1 to 30 mol, preferably 0.8 to 10 mol, per 1 mol of compound (IVj).

Examples of the "additive" include organic acids such as formic acid, acetic acid, propionic acid and the like, and the like.

The amount of the "additive" to be used is about 0.1 to 30 mol, preferably 0.8 to 10 mol, per 1 mol of compound (IVj).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

In (method 2) to synthesize compound (IVk) from compound (IVj) and compound (VII), the reductive amination reaction in the first step advantageously proceeds in the co-presence of an ammonium salt, a reducing agent and, where necessary, an additive.

The amount of compound (VII) to be used is about 0.1 to 30 mol, preferably 0.8 to 10 mol, per 1 mol of compound (IVj).

Examples of the "ammonium salt" include ammonium acetate, ammonium formate, ammonium chloride and the like.

The amount of the "ammonium salt" to be used is about 0.1 to 30 mol, preferably 0.8 to 10 mol, per 1 mol of compound (IVj).

Examples of the "reducing agent" include sodium triacetoxyborohydride, sodium cyanoborohydride, 2-picolineborane and the like.

The amount of the "reducing agent" to be used is about 0.1 to 30 mol, preferably 0.8 to 10 mol, per 1 mol of compound (IVj).

Examples of the "additive" include organic acids such as formic acid, acetic acid, propionic acid and the like, and the like.

The amount of the "additive" to be used is about 0.1 to 30 mol, preferably 0.8 to 10 mol, per 1 mol of compound (IVj).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

In (method 2) to synthesize compound (IVk) from compound (IVj) and compound (VII), the coupling reaction in the second step advantageously proceeds in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVj).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably about −10 to 180° C. Where necessary, a temperature not less than or not more than that can be selected. The reaction time is generally about 5 min to 72 hr, preferably about 5 min to 24 hr. Where necessary, a time not less than or not more than that can be selected.

In (method 2) to synthesize compound (IVk) from compound (IVj) and compound (VII), the deprotection reaction in the third step advantageously proceeds in the co-presence of an acid.

Examples of the "acid" include trifluoroacetic acid and the like.

The amount of the "acid" to be used is about 0.1- to 300-fold, preferably 0.8- to 50-fold, in weight ratio relative to compound (IVj).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; organic acids such as formic acid, acetic acid and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

The reaction to synthesize compound (IVl) from compound (IVk) advantageously proceeds under heating conditions and in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVk).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about 0 to 300° C., preferably 60 to 230° C. Where necessary, a temperature not less than or not more than that can be selected. The reaction time is generally about 5 min to 72 hr, preferably about 5 min to 24 hr. Where necessary, a time not less than or not more than that can be selected.

The intramolecular cyclization reaction of compound (IVl) is performed in the co-presence of halogenated phosphoryls such as phosphorus oxychloride, phosphorus oxybromide and the like, arylphosphinic chlorides such as diphenylphosphinic chloride and the like, and the like.

The amount of the "halogenated phosphoryls and arylphosphinic chlorides" to be used is 0.1- to 300-fold, preferably 1- to 30-fold, in weight ratio relative to compound (IVl), or about 0.1 to 500 mol, preferably 1 to 100 mol, per 1 mol of compound (IVl).

This reaction is advantageously carried out without solvent or in a solvent inert to the reaction. The solvent is not particularly limited as long as the reaction proceeds, and preferable examples thereof include hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

In (method 3) to synthesize compound (IVm) from compound (IVj) and compound (VIII), the reductive amination reaction advantageously proceeds in the co-presence of a reducing agent and, where necessary, an additive.

The amount of compound (VIII) to be used is about 0.1 to 30 mol, preferably 0.8 to 10 mol, per 1 mol of compound (IVj).

Examples of the "reducing agent" include sodium triacetoxyborohydride, sodium cyanoborohydride, 2-picolineborane and the like.

The amount of the "reducing agent" to be used is about 0.1 to 30 mol, preferably 0.8 to 10 mol, per 1 mol of compound (IVj)

Examples of the "additive" include organic acids such as formic acid, acetic acid, propionic acid and the like, and the like.

The amount of the "additive" to be used is about 0.1 to 30 mol, preferably 0.8 to 10 mol, per 1 mol of compound (IVj).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

In (method 3) to synthesize compound (IVn) from compound (IVm), the reaction advantageously proceeds under heating conditions and in the co-presence of a base as necessary.

Examples of the "base" include inorganic bases such as sodium hydroxide, barium hydroxide and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (IVk).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like.

The reaction temperature is about 0 to 300° C., preferably 60 to 230° C. Where necessary, a temperature not less than or not more than that can be selected. The reaction time is generally about 5 min to 72 hr, preferably about 5 min to 24 hr. Where necessary, a time not less than or not more than that can be selected.

In (method 3) to synthesize compound (IVl) from compound (IVn), the deprotection reaction advantageously proceeds in the co-presence of an acid.

Examples of the "acid" include trifluoroacetic acid and the like.

The amount of the "acid" to be used is about 0.1- to 300-fold, preferably 0.8- to 50-fold, in weight ratio relative to compound (IVn).

This reaction is advantageously carried out without solvent or in a solvent inert to the reaction. The solvent is not particularly limited as long as the reaction proceeds, and preferable examples thereof include ethers such as diethyl ether, tetrahydrofuran, dioxane, 1,2-dimethoxyethane, cyclopentyl methyl ether and the like; hydrocarbons such as benzene, toluene, xylene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; organic acids such as formic acid, acetic acid and the like; water and the like, a mixed solvent thereof, and the like.

The reaction temperature is about −40 to 250° C., preferably −10 to 180° C. Where necessary, a temperature not less than or not more than that can be selected. The reaction time is generally about 5 min to 72 hr, preferably about 5 min to 24 hr. Where necessary, a time not less than or not more than that can be selected.

Compound (I) or an intermediate therefor can also be converted to an optically active compound (I) or an optically active intermediate therefor by optical resolution by a known method or a method analogous thereto. For example, the method of optical resolution may be a method known per se, such as a fractional recrystallization method, a chiral column method, a diastereomer method etc. As the "fractional recrystallization method, a method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer can be mentioned. As the "chiral column method", a method wherein a racemate or a salt thereof is applied to a column for separation of an optical isomer (a chiral column) to allow separation. In the case of a liquid chromatography, for example, a racemate is applied to a chiral column such as ENANTIO-OVM (manufactured by Tosoh Corporation), CHIRAL series (manufactured by Daicel Chemical Industries, Ltd.) and the like, and developed with water, buffers (e.g., phosphate buffer, etc.) and organic solvents (e.g., hexane, ethanol, methanol, isopropanol, acetonitrile, trifluoroacetic acid, diethylamine, triethylamine etc.), solely or as a mixed solvent thereof to separate the optical isomer can be mentioned. In the case of a gas chromatography, for example, a chiral column such as CP-Chirasil-DeX CB (manufactured by GL Sciences Inc.) and the like is used to allow separation. As the "diastereomer method", a method including reacting a racemate and an optically active reagent to obtain a mixture of diastereomers, which is then subjected to a general separation means (e.g., fractional recrystallization, chromatography method etc.) to give one of the diastereomers, which is then subjected to a chemical reaction (e.g., acid hydrolysis reaction, base hydrolysis reaction, hydrogenolysis reaction etc.) to separate the optically active reagent moiety to give a desired optical isomer can be mentioned. Examples of the "optically active reagent" include optically active organic acids such as MTPA [α-methoxy-α-(trifluoromethyl)phenylacetic acid], (−)-menthoxyacetic acid and the like; optically active alkoxymethyl halides such as (1R-endo)-2-(chloromethoxy)-1,3,3-trimethylbicyclo[2.2.1]heptane and the like, and the like.

Compound (I) obtained by the aforementioned methods or an intermediate therefor can be isolated or purified by the ordinary separation means such as recrystallization, distillation, chromatography and the like. When compound (I) is obtained in a free form, it can be converted to a salt by a known method or a comparable method (e.g., neutralization, etc.). Conversely, when it is obtained as a salt, it can be converted to a free form or other salt by a method known per se or by a comparable method.

As a salt of compound (I) or an intermediate therefor, for example, a pharmacologically acceptable salt and the like are used. Examples thereof include salts with inorganic bases, salts with organic bases, salts with inorganic acids, salts with organic acids, salts with basic or acidic amino acids and the like can be mentioned. As preferable examples of the salts with inorganic bases, alkali metal salts such as sodium salt, potassium salt and the like; alkaline earth metal salts such as calcium salt, magnesium salt and the like; aluminum salt, ammonium salt and the like can be mentioned. As preferable examples of the salts with organic bases, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like can be mentioned. As preferable examples of the salts with inorganic acids, salts with hydrochloric acid, hydrobromic acid, nitric acid, sulfuric acid, phosphoric acid and the like can be mentioned. As preferable examples of the salts with organic acids, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acids, salts with arginine, lysine, ornithine and the like can be mentioned. Preferable examples of the salts with acidic amino acids include salts with aspartic acid, glutamic acid and the like. Of these, a pharmaceutically acceptable salt is preferable. When compound (I) or an intermediate therefor contains a basic functional group, examples thereof include salts with inorganic acids such as hydrochloric acid, hydrobromic acid, nitric acid, sulfuric acid, phosphoric acid and the like, salts with organic acids such as acetic acid, phthalic acid, fumaric acid, tartaric acid, maleic acid, citric acid, succinic acid, methanesulfonic acid, p-toluenesulfonic acid and the like. When compound (I) or an intermediate therefor contains an acidic functional group, examples thereof include alkali metal salts such as sodium salt, potassium salt and the like, alkaline earth metal salts such as calcium salt, magnesium salt and the like, ammonium salt and the like.

When compound (I) has isomers, such isomers can be obtained as independent products by a synthesis means or a separation means (concentration, solvent extraction, column chromatography, recrystallization and the like) known per se.

The compound of the present invention is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), neurosis, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington chorea, multi-infarct dementia, frontotemporal dementia, frontotemporal dementia Parkinson's Type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis], (3) age-related cognition memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, stress gastrointestinal disorder, and the like.

Since the compound of the present invention has a superior RMPA receptor function enhancing action, a superior prophylactic or therapeutic effect for the above-mentioned diseases can be expected.

A prodrug of compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity and the like). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with schizophrenia (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following, benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, $5\text{-}HT_{1A}$ agonist (buspirone hydrochloride, tandospirone citrate, osemozotan hydrocloride etc.), $5\text{-}HT_3$ antagonist (Cyamemazine etc.), heart non-selective 1 inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), $5\text{-}HT_{2A}$ antagonist, $5\text{-}HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like. The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5)

administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination drug of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Preparation Examples. However, the examples do not limit the present invention and the present invention can be modified within the scope of the present invention.

The "room temperature" in the following Examples is generally about 10° C. to about 35° C. % means wt % unless otherwise specified.

In silica gel column chromatography, the indication of basic means use of aminopropylsilane-bonded silica gel. In HPLC (high performance liquid chromatography), the indication of C18 means use of octadecyl-bonded silica gel.

In the following Examples, the following abbreviations are used.
DMF: N,N-dimethylformamide
THF: tetrahydrofuran
DMSO: dimethyl sulfoxide
IPE: diisopropyl ether
TFA: trifluoroacetic acid
N: normality
M: mol/l
$^1$H NMR (proton nuclear magnetic resonance spectrum) was measured by Fourier-transform type NMR. For the analysis, ACD/SpecManager (trade name) and the like were used. Very mild peaks showing protons of hydroxyl group, amino group and the like are not described.

The following abbreviations are used to show measurement results of $^1$H NMR.
  s: singlet, d: doublet, dd: double doublet, dt: double triplet, t: triplet, q: quartet, m: multiplet, brs: broad singlet, spt: septet, quin: quintet, sxt: sixtet, J: coupling constant, Hz: Hertz.

MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data shows Found.

Example 1

9-(4-(4-chlorophenoxyl)phenyl)-3,4,6,7,8,9-hexahydro-6,9-ethanopyrido[2,1-c][1,2,4]thiadiazine 2,2-dioxide

A) methyl (4-methoxyphenyl)acetate

A mixture of methyl (4-hydroxyphenyl)acetate (66.4 g), DMF (500 ml), potassium carbonate (82.8 g) and iodomethane (85.2 g) was stirred at room temperature for 24 hr. The reaction mixture was poured into ice water (1500 ml), and the mixture was extracted three times with ethyl acetate (200 ml). The obtained organic layers were combined, dried over anhydrous sodium sulfate and concentrated under reduced pressure. The residue was purified by silica gel column chromatography (ethyl acetate/petroleum ether) to give the title compound (60.0 g) as a colorless oily liquid.
MS (ESI+). found: 181.0.

B) dimethyl 4-hydroxy-1-(4-methoxyphenyl)cyclohex-3-en-1,3-dicarboxylate

To a mixture of methyl (4-methoxyphenyl)acetate (36.0 g), methyl acrylate (34.4 g) and THF (300 ml) was added, under ice-cooling, potassium tertbutoxide (67.2 g) and the mixture was stirred at room temperature for 4 hr. To the reaction mixture was added water (300 ml), and the mixture was extracted twice with ethyl acetate (200 ml). The obtained organic layers were combined, dried over anhydrous sodium sulfate and concentrated under reduced pressure to give the title compound (70.0 g) as a yellow oily liquid.
$^1$H NMR (400 MHz, CDCl$_3$) δ 2.15 (2H, m), 2.40 (2H, m), 2.69 (1H, d, J=16 Hz), 3.03 (1H, d, J=16 Hz), 3.63 (3H, s), 3.79 (3H, s), 3.81 (3H,$), 6.85 (2H, d, J=9.2 Hz), 7.26 (2H, d, J=9.2 Hz), 12.11 (1H, s).

C) methyl 1-(4-methoxyphenyl)-4-oxocyclohexanecarboxylate

To a mixture of dimethyl 4-hydroxy-1-(4-methoxyphenyl)cyclohex-3-en-1,3-dicarboxylate (70.0 g), water (200 ml), THF (200 ml) and methanol (200 ml) was added potassium hydroxide (18.4 g) and the mixture was heated under reflux for 12 hr. The reaction mixture was cooled to room temperature, and extracted twice with ethyl acetate (200 ml). The obtained organic layers were combined, dried over anhydrous sodium sulfate and concentrated under reduced pressure. The residue was crystallized from ethyl acetate/petroleum ether to give the title compound (30.0 g) as a white solid.
MS (ESI+). found: 263.0.

D) methyl 1-(4-methoxyphenyl)-4-((2-sulfamoylethyl)amino)cyclohexanecarboxylate To a mixture of methyl 1-(4-methoxyphenyl)-4-oxocyclohexanecarboxylate (2.4 g), 2-aminoethanesulfonamide (1.1 g), acetic acid (0.6 g) and acetonitrile (20 ml) was added, under ice-cooling, sodium triacetoxyborohydride (3.9 g) and the mixture was stirred at room temperature for 4 hr. To the reaction mixture was added 1N aqueous sodium hydroxide solution (30 ml), and the mixture was extracted three times with ethyl acetate (30 ml). The obtained organic layers were combined, dried over anhydrous sodium sulfate and concentrated under reduced pressure to give the title compound (3.1 g) as a yellow oily liquid.
MS (ESI+). found: 370.9.

E) 2-(4-(4-methoxyphenyl)-3-oxo-2-azabicyclo[2.2.2]oct-2-yl)ethanesulfonamide A mixture of methyl 1-(4-methoxyphenyl)-4-((2-sulfamoylethyl)amino)cyclohexanecarboxylate (15.0 g) and methanol (75 ml) was placed in a sealed pressure container, and the mixture was stirred at 200° C. for 48 hr. The reaction mixture was cooled to room temperature, and concentrated under reduced pressure. The residue was purified by silica gel column chromatography (methanol/dichloromethane) to give the title compound (2.9 g) as a yellow oily liquid.
MS (ESI+). found: 338.9.

F) 9-(4-methoxyphenyl)-3,4,6,7,8,9-hexahydro-6,9-ethanopyrido[2,1-c][1,2,4]thiadiazine 2,2-dioxide A mixture of 2-(4-(4-methoxyphenyl)-3-oxo-2-azabicyclo[2.2.2]oct-2-yl)ethanesulfonamide (5.0 g) and phosphorus oxychloride (50 ml) was heated under reflux for 4 hr. The reaction mixture was cooled to room temperature, 4M aqueous sodium hydrogen carbonate solution (50 ml) was added, and the mixture was extracted four times with dichloromethane (50 ml). The obtained organic layers were combined, dried over anhydrous sodium sulfate and concentrated under reduced pressure to give the title compound (4.5 g) as a white solid.
MS (ESI+). found: 321.0.

G) 4-(2,2-dioxido-3,4,7,8-tetrahydro-6,9-ethanopyrido[2,1-c][1,2,4]thiadiazin-9(6H)-yl)phenol To a mixture of 9-(4-methoxyphenyl)-3,4,6,7,8,9-hexahydro-6,9-ethanopyrido[2,1-c][1,2,4]thiadiazine 2,2-dioxide (5.4 g) and dichloromethane (100 ml) was added a 3M solution (14 ml) of boron tribromide in dichloromethane, and the mixture was heated under reflux for 4 hr. The reaction mixture was cooled to room temperature, and poured into crushed ice (100 g). The mixture was alkalified (pH=8-9) with sodium hydrogen carbonate, and the precipitated solid was collected by filtration to give the title compound (3.0 g) as a pale-yellow solid.
$^1$H NMR (400 MHz, DMSO-d$_6$) δ 1.77-1.94 (6H, m), 2.05-2.08 (2H, m), 3.20 (2H, t, J=6.4 Hz), 3.78 (1H, s), 3.91 (2H, t, J=6.4 Hz), 6.70 (2H, d, J=8.4 Hz), 7.09 (2H, d, J=8.4 Hz), 9.26 (1H, s).

H) 9-(4-(4-chlorophenoxyl)phenyl)-3,4,6,7,8,9-hexahydro-6,9-ethanopyrido[2,1-c][1,2,4]thiadiazine 2,2-dioxide To a mixture of 4-(2,2-dioxido-3,4,7,8-tetrahydro-6,9-ethanopyrido[2,1-c][1,2,4]thiadiazin-9(6H)-yl)phenol (20 mg), pyridine (155 mg), molecular sieve 4A (200 mg), cesium carbonate (21 mg), 4-chlorophenylboronic acid (51 mg) and acetonitrile (2 ml) was added copper(II) acetate (36 mg), and the mixture was stirred at room temperature for 15 hr. To the reaction mixture were added THF and silica gel and the mixture was concentrated under reduced pressure. The residue was purified by basic silica gel column chromatography (methanol/ethyl acetate), and crystallized from THF/IPE to give the title compound (7.2 mg) as white crystals.

MS (API+). found: 417.1.

$^1$H NMR (300 MHz, DMSO-$d_6$) δ 1.74-1.84 (2H, m), 1.88-1.99 (4H, m), 2.06-2.19 (2H, m), 3.19-3.25 (2H, m), 3.77-3.84 (1H, m), 3.87-3.96 (2H, m), 6.93-7.00 (2H, m), 7.02-7.10 (2H, m), 7.29-7.37 (2H, m), 7.39-7.49 (2H, m).

Example 2

9-(4-(3-(1,1-difluoroethyl)phenoxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 1-bromo-3-(1,1-difluoroethyl)benzene (108 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 3 hr. After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from ethyl acetate/hexane to give the title compound (63.6 mg) as white crystals.

MS (API+). found: 447.2.

$^1$H NMR (300 MHz, DMSO-$d_6$) δ 1.74-2.18 (11H, m), 3.18-3.26 (2H, m), 3.76-3.85 (1H, m), 3.88-3.97 (2H, m), 6.92-7.02 (2H, m), 7.09-7.17 (1H, m), 7.20-7.25 (1H, m), 7.28-7.40 (3H, m), 7.46-7.59 (1H, m).

Example 3

9-(4-phenoxyphenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), iodobenzene (100 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 10 hr. After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from THF/IPE to give the title compound (63.7 mg) as white crystals.

MS (API+). found: 383.1.

$^1$H NMR (300 MHz, DMSO-$d_6$) δ 1.73-1.85 (2H, m), 1.86-2.01 (4H, m), 2.05-2.19 (2H, m), 3.18-3.26 (2H, m), 3.78-3.85 (1H, m), 3.88-3.97 (2H, m), 6.89-6.97 (2H, m), 7.00-7.08 (2H, m), 7.11-7.19 (1H, m), 7.29-7.35 (2H, m), 7.36-7.45 (2H, m).

Example 4

9-(4-(4-(1,1-difluoroethyl)phenoxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 1-bromo-4-(1,1-difluoroethyl)benzene (108 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 6 hr. After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from ethyl acetate/hexane to give the title compound (64.9 mg) as white crystals.

MS (API+). found: 447.2.

$^1$H NMR (300 MHz, DMSO-$d_6$) b 1.71-2.21 (11H, m), 3.17-3.28 (2H, m), 3.78-3.85 (1H, m), 3.87-4.03 (2H, m), 7.01 (2H, d, J=9.1 Hz), 7.10 (2H, d, J=8.7 Hz), 7.36 (2H, d, J=9.1 Hz), 7.59 (2H, d, J=8.7 Hz).

Example 5

9-(4-(3-chlorophenoxyl)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 1-chloro-3-iodobenzene (117 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 6 hr. After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from THF/IPE to give the title compound (68.0 mg) as white crystals.

MS (API+). found: 417.1.

$^1$H NMR (300 MHz, DMSO-$d_6$) δ 1.72-2.03 (6H, m), 2.05-2.20 (2H, m), 3.17-3.26 (2H, m), 3.77-3.85 (1H, m), 3.88-3.99 (2H, m), 6.93-7.04 (3H, m), 7.05-7.12 (1H, m), 7.21 (1H, dd, J=7.8, 1.7 Hz), 7.29-7.49 (3H, m).

Example 6

9-(4-(3,4-dichlorophenoxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 1,2-dichloro-4-iodobenzene (134 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 6 hr.

After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from THF/IPE to give the title compound (68.0 mg) as white crystals.

MS (API+). found: 451.1.

$^{1}$H NMR (300 MHz, DMSO-$d_6$) δ 1.71-1.86 (2H, m), 1.87-2.03 (4H, m), 2.04-2.21 (2H, m), 3.18-3.26 (2H, m), 3.76-3.86 (1H, m), 3.88-3.97 (2H, m), 6.96-7.09 (3H, m), 7.29-7.41 (3H, m), 7.56-7.71 (1H, m).

Example 7

9-(4-(3-chloro-4-fluorophenoxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 4-bromo-2-chloro-1-fluorobenzene (103 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was added copper(I) iodide (25 mg), and the mixture was stirred under a nitrogen atmosphere at 130° C. for 6 hr. After cooling to room temperature, to the reaction mixture was added ethyl acetate and the mixture was filtered through celite. Water was added to the filtrate, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and fractionated by HPLC (C18, mobile phase: water/acetonitrile (0.1% TFA-containing system)). To the obtained fraction was added saturated aqueous sodium carbonate solution, and the mixture was extracted with ethyl acetate. The extract was dried over anhydrous magnesium sulfate and concentrated under reduced pressure. The obtained residue was crystallized from THF/IPE to give the title compound (45.3 mg) as white crystals.

MS (API+). found: 435.1.

$^{1}$H NMR (300 MHz, DMSO-$d_6$) δ 1.70-2.02 (6H, m), 2.03-2.21 (2H, m), 3.16-3.26 (2H, m), 3.76-3.84 (1H, m), 3.86-3.98 (2H, m), 6.90-7.02 (2H, m), 7.03-7.12 (1H, m), 7.26-7.38 (3H, m), 7.45 (1H, t, J=9.0 Hz).

Example 8

9-(4-(cycloheptyloxy)phenyl)-3,4,6,7,8,9-hexahydro-6,9-ethanopyrido[2,1-c][1,2,4]thiadiazine 2,2-dioxide A mixture of potassium carbonate (135 mg), bromocycloheptane (116 mg), 4-(2,2-dioxido-3,4,7,8-tetrahydro-6,9-ethanopyrido[2,1-c][1,2,4]thiadiazin-9(6H)-yl)phenol (100 mg) and DMSO (2 ml) was stirred at 130° C. overnight. After cooling to room temperature, water was added to the reaction mixture, and the mixture was extracted with ethyl acetate. The organic layer was washed with saturated brine, silica gel was added and the mixture was concentrated under reduced pressure. The residue was purified by basic silica gel column chromatography (methanol/ethyl acetate), and crystallized from THF/IPE to give the title compound (14.7 mg) as white crystals.

MS (API+). found: 403.2.

$^{1}$H NMR (300 MHz, DMSO-$d_6$) δ 1.43-2.13 (20H, m), 3.15-3.24 (2H, m), 3.74-3.83 (1H, m), 3.85-3, 98 (2H, m), 4.47 (1H, tt, J=8.0, 4.1 Hz), 6.81 (2H, d, J=8.9 Hz), 7.19 (2H, d, J=8.9 Hz).

Example 9

9-(4-(3-methoxyphenoxyl)phenyl)-3,4,6,7,8,9-hexahydro-6,9-ethanopyrido[2,1-c][1,2,4]thiadiazine 2,2-dioxide To a mixture of 2-picolinic acid (24 mg), tripotassium phosphate (312 mg), 1-iodo-3-methoxybenzene (172 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was added copper(I) iodide (37 mg), and the mixture was stirred under a nitrogen atmosphere at 130° C. overnight. The reaction mixture was purified by basic silica gel column chromatography (methanol/ethyl acetate), water was added and the mixture was extracted with ethyl acetate. The organic layer was washed with saturated brine, dried over anhydrous sodium sulfate, and concentrated under reduced pressure. The obtained residue was crystallized from THF/IPE to give the title compound (105.5 mg) as white crystals.

MS (API+). found: 413.2.

$^{1}$H NMR (300 MHz, DMSO-$d_6$) δ 1.70-2.01 (6H, m), 2.02-2.22 (2H, m), 3.19-3.26 (2H, m), 3.74 (3H, s), 3.77-3.84 (1H, m), 3.87-3.96 (2H, m), 6.54-6.64 (2H, m), 6.68-6.77 (1H, m), 6.88-7.00 (2H, m), 7.22-7.37 (3H, m).

Example 10

9-(4-(2-chlorophenoxyl)phenyl)-3,4,6,7,8,9-hexahydro-6,9-ethanopyrido[2,1-c][1,2,4]thiadiazine 2,2-dioxide To a mixture of 2-picolinic acid (24 mg), tripotassium phosphate (312 mg), 1-chloro-2-iodobenzene (175 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was added copper(I) iodide (37 mg), and the mixture was stirred under a nitrogen atmosphere at 130° C. overnight. The reaction mixture was purified by basic silica gel column chromatography (methanol/ethyl acetate), and crystallized from THF/IPE to give the title compound (45.9 mg) as white crystals.

MS (API+). found: 417.1.

$^{1}$H NMR (300 MHz, DMSO-$d_6$) δ 1.71-1.98 (6H, m), 2.02-2.18 (2H, m), 3.18-3.25 (2H, m), 3.76-3.85 (1H, m), 3.87-3.96 (2H, m), 6.83-6.91 (2H, m), 7.16 (1H, dd, J=8.1, 1.5 Hz), 7.20-7.27 (1H, m), 7.28-7.42 (3H, m), 7.61 (1H, dd, J=7.9, 1.5 Hz).

Example 11

9-(4-(2-methylphenoxyl)phenyl)-3,4,6,7,8,9-hexahydro-6,9-ethanopyrido[2,1-c][1,2,4]thiadiazine 2,2-dioxide To a mixture of 2-picolinic acid (24 mg), tripotassium phosphate (312 mg), 2-bromotoluene (126 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was added copper(I) iodide (37 mg), and the mixture was stirred under a nitrogen atmosphere at 130° C. overnight. The reaction mixture was purified by basic silica gel column chromatography (methanol/ethyl acetate), and crystallized from THF/IPE to give the title compound (11.2 mg) as white crystals.

MS (API+). found: 397.2.

$^1$H NMR (300 MHz, DMSO-d$_6$) δ 1.76-1.97 (6H, m), 2.03-2.14 (2H, m), 2.19 (3H, s), 3.16-3.25 (2H, m), 3.77-3.84 (1H, m), 3.87-3.96 (2H, m), 6.77-6.85 (2H, m), 6.94 (1H, dd, J=8.0, 1.2 Hz), 7.07-7.15 (1H, m), 7.17-7.37 (4H, m).

Example 13

9-(4-(2,3-dihydro-1-benzofuran-6-yloxy)phenyl)-3,4,6,7,8,9-hexahydro-6,9-ethanopyrido[2,1-c][1,2,4]thiadiazine 2,2-dioxide To a mixture of 2-picolinic acid (24 mg), tripotassium phosphate (312 mg), 6-bromo-2,3-dihydrobenzofuran (146 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was added copper(I) iodide (37 mg), and the mixture was stirred under a nitrogen atmosphere at 130° C. for 6 hr. The reaction mixture was purified by basic silica gel column chromatography (methanol/ethyl acetate), and crystallized from THF/IPE to give the title compound (12.8 mg) as white crystals.

MS (API+). found: 425.2.

$^1$H NMR (300 MHz, DMSO-d$_6$) δ 1.73-1.97 (6H, m), 2.04-2.18 (2H, m), 3.10-3.25 (4H, m), 3.76-3.84 (1H, m), 3.88-3.96 (2H, m), 4.57 (2H, t, J=8.6 Hz), 6.41-6.51 (2H, m), 6.86-6.95 (2H, m), 7.17-7.34 (3H, m).

Example 14

9-(4-(4-(trifluoromethyl)phenoxy)phenyl)-3,4,6,7,8,9-hexahydro-6,9-ethanopyrido[2,1-c][1,2,4]thiadiazine 2,2-dioxide To a mixture of 2-picolinic acid (24 mg), tripotassium phosphate (312 mg), 1-bromo-4-(trifluoromethyl)benzene (165 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was added copper(I) iodide (37 mg), and the mixture was stirred under a nitrogen atmosphere at 130° C. overnight. After cooling to room temperature, water was added to the reaction mixture, and the mixture was extracted with ethyl acetate. The organic layer was washed with saturated brine, dried over anhydrous sodium sulfate and concentrated under reduced pressure. The residue was purified by basic silica gel column chromatography (methanol/ethyl acetate), and crystallized from ethyl acetate/hexane to give the title compound (110.0 mg) as white crystals.

MS (API+). found: 451.1.

$^1$H NMR (300 MHz, DMSO-d$_6$) δ 1.70-1.87 (2H, m), 1.88-2.03 (4H, m), 2.06-2.21 (2H, m), 3.23 (2H, s), 3.78-3.85 (1H, m), 3.87-3.98 (2H, m), 7.02-7.11 (2H, m), 7.17 (2H, d, J=8.3 Hz), 7.33-7.44 (2H, m), 7.75 (2H, d, J=8.3 Hz).

Example 15

9-(4-((4-(trifluoromethyl)pyridin-2-yl)oxy)phenyl)-3,4,6,7,8,9-hexahydro-6,9-ethanopyrido[2,1-c][1,2,4]thiadiazine 2,2-dioxide A mixture of potassium carbonate (81 mg), 2-fluoro-4-(trifluoromethyl)pyridine (97 mg), 4-(2,2-dioxido-3,4,7,8-tetrahydro-6,9-ethanopyrido[2,1-c][1,2,4]thiadiazin-9(6H)-yl)phenol (150 mg) and DMSO (3 ml) was stirred at 130° C. overnight. After cooling to room temperature, water was added to the reaction mixture, and the mixture was extracted with ethyl acetate. The organic layer was washed with saturated brine, dried over anhydrous sodium sulfate and concentrated under reduced pressure. The residue was crystallized from THF-ethyl acetate/IPE to give the title compound (165.5 mg) as white crystals.

MS (API+). found: 452.2.

$^1$H NMR (300 MHz, DMSO-d$_6$) δ 1.72-1.87 (2H, m), 1.90-2.04 (4H, m), 2.07-2.21 (2H, m), 3.19-3.26 (2H, m), 3.78-3.86 (1H, m), 3.88-3.99 (2H, m), 7.14 (2H, d, J=8.7 Hz), 7.38 (2H, d, J=8.7 Hz), 7.45-7.52 (2H, m), 8.44 (1H, d, J=5.5 Hz).

Example 16

3-(4-(2,2-dioxido-3,4,7,8-tetrahydro-6,9-ethanopyrido[2,1-c][1,2,4]thiadiazin-9(6H)-yl)phenoxy)benzonitrile To a mixture of 2-picolinic acid (16 mg), tripotassium phosphate (208 mg), 3-bromobenzonitrile (89 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. for 8 hr. After cooling to room temperature, water was added to the reaction mixture, and the mixture was extracted with ethyl acetate. The organic layer was washed with saturated brine, dried over anhydrous sodium sulfate and concentrated under reduced pressure. The residue was purified by basic silica gel column chromatography (methanol/ethyl acetate), and crystallized from ethyl acetate/hexane to give the title compound (46.9 mg) as white crystals.

MS (API+). found: 408.1.

$^1$H NMR (300 MHz, DMSO-d$_6$) δ 1.78-2.01 (6H, m), 2.06-2.21 (2H, m), 3.18-3.26 (2H, m), 3.77-3.85 (1H, m), 3.89-3.97 (2H, m), 6.97-7.06 (2H, m), 7.31-7.42 (3H, m), 7.48-7.54 (1H, m), 7.58-7.65 (2H, m).

Example 18

9-(4-(3-(difluoromethyl)phenoxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 1-bromo-3-(difluoromethyl)benzene (101 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. for 8 hr. After cooling to room temperature, water was added to the reaction mixture, and the mixture was extracted with ethyl acetate. The organic layer was washed with saturated brine, dried over anhydrous sodium sulfate and concentrated under reduced pressure. The residue was purified by basic silica gel column chromatography (methanol/ethyl acetate), and crystallized from THF/IPE to give the title compound (61.2 mg) as white crystals.

MS (API+). found: 433.1.

$^1$H NMR (300 MHz, DMSO-d$_6$) δ 1.72-1.86 (2H, m), 1.87-2.02 (4H, m), 2.06-2.21 (2H, m), 3.19-3.26 (2H, m), 3.77-3.85 (1H, m), 3.87-3.97 (2H, m), 6.81-7.24 (5H, m), 7.30-7.40 (3H, m), 7.49-7.62 (1H, m).

Example 19

9-(4-(4-(difluoromethyl)phenoxy)phenyl)-3,4,6,7,8, 9-hexahydro-6,9-ethanopyrido[2,1-c][1,2,4]thiadiazine 2,2-dioxide To a mixture of 2-picolinic acid (16 mg), tripotassium phosphate (208 mg), 1-bromo-4-(difluoromethyl)benzene (101 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. for 8 hr. After cooling to room temperature, water was added to the reaction mixture, and the mixture was extracted with ethyl acetate. The organic layer was washed with saturated brine, dried over anhydrous sodium sulfate and concentrated under reduced pressure. The residue was purified by basic silica gel column chromatography (methanol/ethyl acetate), and crystallized from THF/IPE to give the title compound (61.2 mg) as white crystals.

MS (API+). found: 433.1.

$^1$H NMR (300 MHz, DMSO-$d_6$) δ 1.66-2.29 (8H, m), 3.16-3.26 (2H, m), 3.77-3.86 (1H, m), 3.88-3.99 (2H, m), 6.83-7.21 (5H, m), 7.37 (2H, d, J=8.5 Hz), 7.60 (2H, d, J=8.5 Hz).

Example 20

9-(4-(2-(trifluoromethyl)phenoxy)phenyl)-3,4,6,7,8, 9-hexahydro-6,9-ethanopyrido[2,1-c][1,2,4]thiadiazine 2,2-dioxide To 4-(2,2-dioxido-3,4,7,8-tetrahydro-6,9-ethanopyrido[2,1-c][1,2,4]thiadiazin-9(6H)-yl)phenol (25 mg) were added a mixture of 1-bromo-2-(trifluoromethyl)benzene (36 mg) and DMSO (0.5 ml), copper(I) iodide (6 mg), 2-picolinic acid (4 mg) and tripotassium phosphate (51 mg) and the mixture was stirred under a nitrogen atmosphere at 130° C. overnight. To the reaction mixture were added water (1 ml) and ethyl acetate (3 ml) and the mixture was stirred. The organic layer was passed through a phase separation filter, and the solvent was evaporated from the separated liquid by an air blowing apparatus. The residue was purified by HPLC (column: YMC Triart C18, mobile phase: acetonitrile/10 mM aqueous ammonium acetate solution) to give the title compound (1.6 mg).

Examples 21-25

By a method similar to that in Example 20, the compounds of Examples 21-25 were produced.

Example 26

9-(4-(2,2,2-trifluoroethoxyl)phenyl)-3,4,6,7,8,9-hexahydro-6,9-ethanopyrido[2,1-c][1,2,4]thiadiazine 2,2-dioxide To 4-(2,2-dioxido-3,4,7,8-tetrahydro-6,9-ethanopyrido[2,1-c][1,2,4]thiadiazin-9(6H)-yl)phenol (25 mg) were added a mixture of 2-bromo-1,1,1-trifluoroethane (26 mg) and DMSO (0.5 ml) and potassium carbonate (33 mg), and the mixture was stirred at 130° C. overnight. To the reaction mixture were added water (1 ml) and ethyl acetate (3 ml) and the mixture was stirred. The organic layer was passed through a phase separation filter, and the solvent was evaporated from the separated liquid by an air blowing apparatus. The residue was purified by HPLC (column: YMC Triart C18, mobile phase: acetonitrile/10 mM aqueous ammonium acetate solution) to give the title compound (5.1 mg).

Examples 27-28

By a method similar to that in Example 26, the compounds of Examples 27-28 were produced.

Example 30

By a method similar to that in Example 26, the compound of Example 30 was produced.

Examples 32-36

By a method similar to that in Example 26, the compounds of Examples 32-36 were produced.

Examples 38-39

By a method similar to that in Example 26, the compounds of Examples 38-39 were produced.

Example 40

9-(4-(4-chloro-2-methoxyphenoxy)phenyl)-3,4,6,7,8, 9-hexahydro-6,9-ethanopyrido[2,1-c][1,2,4]thiadiazine 2,2-dioxide To a mixture of 2-picolinic acid (16 mg), tripotassium phosphate (208 mg), 1-bromo-4-chloro-2-methoxybenzene (108 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. overnight. After cooling to room temperature, water was added to the reaction mixture, and the mixture was extracted with ethyl acetate. Silica gel was added to the organic layer, and the mixture was concentrated under reduced pressure. The residue was purified by basic silica gel column chromatography (methanol/ethyl acetate), and crystallized from THF/IPE to give the title compound (24.6 mg) as white crystals.

MS (API+). found: 447.1.

$^1$H NMR (300 MHz, DMSO-$d_6$) δ 1.73-1.83 (2H, m), 1.86-1.99 (4H, m), 2.02-2.17 (2H, m), 3.18-3.24 (2H, m), 3.70-3.83 (4H, m), 3.87-3.96 (2H, m), 6.81 (2H, d, J=9.1 Hz), 7.12 (1H, d, J=2.5 Hz), 7.16-7.31 (4H, m).

Example 41

9-(4-((2,2-difluoro-1,3-benzodioxol-5-yl)oxy)phenyl)-3,4,6,7,8,9-hexahydro-6,9-ethanopyrido[2,1-c][1,2,4]thiadiazine 2,2-dioxide To a mixture of 2-picolinic acid (16 mg), tripotassium phosphate (208 mg), 5-bromo-2,2-difluorobenzo[d][1,3]dioxole (116 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. overnight. After cooling to room temperature, water was added to the reaction mixture and the mixture was extracted with ethyl acetate. Silica gel was added to the organic layer, and the mixture was concentrated under reduced pressure. The residue was purified by basic silica gel column chromatography (methanol/ethyl acetate), and crystallized from THF/IPE-hexane to give the title compound (48.6 mg) as white crystals.

MS (API+). found: 463.0.

$^1$H NMR (300 MHz, DMSO-$d_6$) δ 1.72-1.84 (2H, m), 1.87-2.01 (4H, m), 2.05-2.19 (2H, m), 3.17-3.25 (2H, m), 3.77-3.84 (1H, m), 3.87-3.97 (2H, m), 6.81-6.98 (3H, m), 7.25-7.46 (4H, m).

Example 44

9-(4-phenoxyphenyl)-3,4,6,7,8,9-hexahydropyrimido[2,1-c][1,2,4]thiadiazine 2,2-dioxide A) 1-(3-chloropropyl)-3-(4-phenoxyphenyl)urea To a mixture of 4-phenoxyaniline (3.9 g) and THF (40 ml) was added, under ice-cooling, 3-chloropropylisocyanate (2.7 g), and the mixture was stirred at room temperature overnight. The reaction mixture was concentrated under reduced pressure, and the residue was washed with diethyl ether and IPE to give the title compound (6.1 g) as a gray-white solid.

MS (API+). found: 305.1.

B) 1-(4-phenoxyphenyl)tetrahydropyrimidin-2(1H)-one

To a mixture of 60% sodium hydride (2.5 g) and THF (100 ml) was added dropwise, at room temperature, a mixture of 1-(3-chloropropyl)-3-(4-phenoxyphenyl)urea (8.8 g) and THF (180 ml), and the mixture was stirred at room temperature for 3 hr. Under ice-cooling, water was added to the reaction mixture to stop the reaction, water (500 ml) was added, and the precipitated solid was collected by filtration and dried under reduced pressure to give the title compound (7.6 g) as a gray white solid.

MS (API+). found: 269.1.

C) 1-(4-phenoxyphenyl)tetrahydropyrimidine-2(1H)-thione

To a mixture of 1-(4-phenoxyphenyl)tetrahydropyrimidin-2(1H)-one (1.0 g), cyclopentyl methyl ether (15 ml) and toluene (7 ml) was added a Lawesson reagent (2.3 g), and the mixture was stirred at 120° C. overnight. To the reaction mixture was added silica gel, and the mixture was concentrated under reduced pressure. The residue was purified by silica gel column chromatography (ethyl acetate/hexane), and crystallized from THF/IPE to give the title compound (502 mg) as white crystals.

MS (API+). found: 285.0.

D) 9-(4-phenoxyphenyl)-3,4,6,7,8,9-hexahydropyrimido[2,1-c][1,2,4]thiadiazine 2,2-dioxide To a mixture of 1-(4-phenoxyphenyl)tetrahydropyrimidine-2(1H)-thione (502 mg), THF (5 ml) and methanol (5 ml) was added iodomethane (752 mg), and the mixture was stirred at 60° C. for 15 hr. The reaction mixture was concentrated under reduced pressure, and acetonitrile (10 ml), THF (5 ml), triethylamine (894 mg) and ammonium acetate (550 mg) were added to the residue, and the mixture was stirred at 60° C. for 3 days. To the reaction mixture was added ammonium acetate (550 mg), and the mixture was stirred at 70° C. for 2 days. The reaction mixture was divided into two and one of them was concentrated under reduced pressure. The obtained residue was suspended in THF (10 ml), and the suspension was added dropwise to a mixture of 2-chloroethanesulfonyl chloride (500 mg), 60% sodium hydride (307 mg) and THF (10 ml) under ice-cooling. The reaction mixture was stirred at 45° C. overnight, water was added under ice-cooling, and the mixture was extracted with ethyl acetate. The organic layer was washed with saturated brine, dried over anhydrous magnesium sulfate and concentrated under reduced pressure. The residue was purified by basic silica gel column chromatography (methanol/ethyl acetate), and crystallized from ethyl acetate/hexane to give the title compound (2.9 mg) as white crystals.

MS (API+). found: 358.1.

$^1$H NMR (300 MHz, DMSO-$d_6$) δ 1.99-2.14 (2H, m), 3.09-3.19 (2H, m), 3.44 (2H, t, J=5.7 Hz), 3.55 (2H, t, J=5.7 Hz), 3.66-3.78 (2H, m), 6.90-7.01 (2H, m), 7.02-7.10 (2H, m), 7.12-7.26 (3H, m), 7.36-7.47 (2H, m).

Example 45

9-(4-(4-chlorophenoxyl)phenyl)-3,4,6,7,8,9-hexahydropyrimido[2,1-c][1,2,4]thiadiazine 2,2-dioxide A) 1-(4-(4-chlorophenoxyl)phenyl)-3-(3-chloropropyl)urea To a mixture of 4-(4-chlorophenoxy)aniline (8.8 g) and THF (50 ml) was added, under ice-cooling, 3-chloropropylisocyanate (5.0 g) and the mixture was stirred at room temperature overnight. The reaction mixture was concentrated under reduced pressure, and the residue was washed with IPE to give the title compound (13.1 g) as a white solid.

MS (API+). found: 339.0.

B) 1-(4-(4-chlorophenoxyl)phenyl)tetrahydropyrimidin-2(1H)-one

To a mixture of 60% sodium hydride (3.4 g) and THF (145 ml) was added dropwise, under ice-cooling, a mixture of 1-(4-(4-chlorophenoxyl)phenyl)-3-(3-chloropropyl)urea (13.1 g) and THF (150 ml), and the mixture was stirred at room temperature for 2 hr. Under ice-cooling, water was added to the reaction mixture to stop the reaction, water (1000 ml) was added, and the precipitated solid was collected by filtration and dried under reduced pressure to give the title compound (12.0 g) as a white solid.

MS (API+). found: 303.0.

C) 1-(4-(4-chlorophenoxyl)phenyl)tetrahydropyrimidine-2(1H)-thione

To a mixture of 1-(4-(4-chlorophenoxyl)phenyl)tetrahydropyrimidin-2(1H)-one (11.7 g), cyclopentyl methyl ether (200 ml) and toluene (80 ml) was added a Lawesson reagent (23.5 g), and the mixture was stirred at 120° C. overnight. The reaction mixture was cooled to room temperature, and the precipitated solid was collected by filtration and dried under reduced pressure to give the title compound (5.5 g) as a white solid.

MS (API+). found: 319.0.

D) 9-(4-(4-chlorophenoxyl)phenyl)-3,4,6,7,8,9-hexahydropyrimido[2,1-c][1,2,4]thiadiazine 2,2-dioxide To a mixture of 1-(4-(4-chlorophenoxyl)phenyl)tetrahydropyrimidine-2(1H)-thione (5.5 g), THF (70 ml), methanol (70 ml) and acetonitrile (15 ml) was added iodomethane (7.4 g), and the mixture was stirred at 60° C. for 3 hr. The reaction mixture was concentrated under reduced pressure, acetonitrile (60 ml), THF (30 ml) and triethylamine (17.5 g) were added to the residue, and the mixture was stirred at room temperature for 10 min. To the reaction mixture was added ammonium acetate (10.6 g), and the mixture was stirred at 75° C. for 1 hr, and at 70° C. for 4 days. The reaction mixture was concentrated under reduced pressure, 3.0 g of the obtained residue was suspended in THF (30 ml), and the suspension was added dropwise, under ice-cooling, to a mixture of 2-chloroethanesulfonyl chloride (8.2 g), 60% sodium hydride (4.0 g) and THF (100 ml). The reaction mixture was stirred at room temperature overnight, and at 50° C. overnight. Under ice-cooling, water was added, and the mixture was extracted with ethyl acetate. Basic silica gel was added to the organic layer and the mixture was concentrated under reduced pressure. The residue was purified by basic silica gel column chromatography (methanol/ethyl acetate), and crystallized from THF-acetonitrile/IPE to give the title compound (64.0 mg) as white crystals.

MS (API+). found: 392.1.

$^1$H NMR (300 MHz, DMSO-$d_6$) δ 2.02-2.13 (2H, m), 3.09-3.17 (2H, m), 3.44 (2H, t, J=6.0 Hz), 3.55 (2H, t, J=5.9 Hz), 3.68-3.76 (2H, m), 6.98-7.12 (4H, m), 7.19-7.27 (2H, m), 7.41-7.49 (2H, m).

Example 46

5-bromo-2-(4-(2,2-dioxido-3,4,7,8-tetrahydro-6,9-ethanopyrido[2,1-c][1,2,4]thiadiazin-9(6H)-yl)phenoxy)benzonitrile To a mixture of 2-picolinic acid (16 mg), tripotassium phosphate (208 mg), 5-bromo-2-fluorobenzonitrile (98 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. for 10 hr. After cooling to room temperature, to the reaction mixture was added ethyl acetate and the mixture was filtered through celite. Water was added to the filtrate, and the mixture was extracted with ethyl acetate. The organic layer was washed with saturated brine, dried over anhydrous sodium sulfate and concentrated under reduced pressure. The residue was purified by basic silica gel column chromatography (ethyl acetate), and crystallized from THF/IPE to give the title compound (21.2 mg) as pale-yellow crystals.

Example 47

5-(4-(2,2-dioxido-3,4,7,8-tetrahydro-6,9-ethanopyrido[2,1-c][1,2,4]thiadiazin-9(6H)-yl)phenoxy)-2-methylbenzonitrile To a mixture of 2-picolinic acid (16 mg), tripotassium phosphate (208 mg), 5-bromo-2-methylbenzonitrile (96 mg), 4-(2,2-dioxido-3,4,7,8-tetrahydro-6,9-ethanopyrido[2,1-c][1,2,4]thiadiazin-9(6H)-yl)phenol (100 mg) and DMSO (3 ml) was added copper(I) iodide (25 mg), and the mixture was stirred under a nitrogen atmosphere at 130° C. for 10 hr. After cooling to room temperature, to the reaction mixture was added ethyl acetate and the mixture was filtered through celite. Water was added to the filtrate, and the mixture was extracted with ethyl acetate. The organic layer was washed with saturated brine, dried over anhydrous sodium sulfate and concentrated under reduced pressure. The residue was purified by basic silica gel column chromatography (ethyl acetate), and crystallized from THF/IPE to give the title compound (46.3 mg) as pale-yellow crystals.

MS (API+). found: 422.2.

$^1$H NMR (300 MHz, DMSO-$d_6$) δ 1.77-1.85 (2H, m), 1.86-2.02 (4H, m), 2.04-2.21 (2H, m), 2.46 (3H, s), 3.17-3.26 (2H, m), 3.76-3.84 (1H, m), 3.86-4.00 (2H, m), 6.80-7.05 (2H, m), 7.19-7.41 (3H, m), 7.41-7.59 (2H, m).

Example 48

2-chloro-4-(4-(2,2-dioxido-3,4,7,8-tetrahydro-6,9-ethanopyrido[2,1-c][1,2,4]thiadiazin-9(6H)-yl)phenoxy)benzonitrile A mixture of potassium carbonate (68 mg), 2-chloro-4-benzonitrile (38 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the precipitated solid was collected by filtration and crystallized from THF-acetonitrile/IPE to give the title compound (36.2 mg) as white crystals.

MS (API+). found: 442.1.

$^1$H NMR (300 MHz, DMSO-$d_6$) δ 1.70-1.88 (2H, m), 1.90-2.05 (4H, m), 2.10-2.24 (2H, m), 3.17-3.28 (2H, m), 3.77-3.86 (1H, m), 3.87-4.01 (2H, m), 7.06 (1H, dd, J=9.0, 2.3 Hz), 7.14 (2H, d, J=8.7 Hz), 7.34 (1H, d, J=2.3 Hz), 7.43 (2H, d, J=8.7 Hz), 7.97 (1H, d, J=9.0 Hz).

Example 49-50

The compounds of Examples 49-50 can be produced by a method similar to that in Examples 1-48.

Example 51

5-(4-(2,2-dioxido-3,4,7,8-tetrahydro-6,9-ethanopyrido[2,1-c][1,2,4]thiadiazin-9(6H)-yl)phenoxy)-2-(trifluoromethyl)benzonitrile A mixture of potassium carbonate (68 mg), 5-fluoro-2-(trifluoromethyl)benzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from ethyl acetate-THF/hexane to give the title compound (47.2 mg) as white crystals.

MS (API+). found: 476.1.

$^1$H NMR (300 MHz, DMSO-$d_6$) δ1.73-1.87 (2H, m), 1.90-2.04 (4H, m), 2.07-2.21 (2H, m), 3.18-3.28 (2H, m), 3.79-3.87 (1H, m), 3.88-4.00 (2H, m), 7.15 (2H, d, J=9.0 Hz), 7.35-7.50 (3H, m), 7.86 (1H, d, J=2.3 Hz), 8.00 (1H, d, J=9.0 Hz).

Example 52

4-(4-(2,2-dioxido-3,4,7,8-tetrahydro-6,9-ethanopyrido[2,1-c][1,2,4]thiadiazin-9(6H)-yl)phenoxy)-2-(trifluoromethyl)benzonitrile A mixture of potassium carbonate (68 mg), 4-fluoro-2-(trifluoromethyl)benzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (45.9 mg) as white crystals.
MS (API+). found: 476.1.
$^1$H NMR (300 MHz, DMSO-$d_6$) δ1.72-1.87 (2H, m), 1.89-2.04 (4H, m), 2.09-2.22 (2H, m), 3.19-3.27 (2H, m), 3.79-3.86 (1H, m), 3.90-3.99 (2H, m), 7.12-7.22 (2H, m), 7.32 (1H, dd, J=8.7, 2.3 Hz), 7.41-7.50 (2H, m), 7.60 (1H, d, J=2.3 Hz), 8.16 (1H, d, J=8.7 Hz).

Example 53

5-chloro-2-(4-(2,2-dioxido-3,4,7,8-tetrahydro-6,9-ethanopyrido[2,1-c][1,2,4]thiadiazin-9(6H)-yl)phenoxy)benzonitrile A mixture of potassium carbonate (68 mg), 5-chloro-2-fluorobenzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (45.4 mg) as white crystals.
MS (API+). found: 442.1.
$^1$H NMR (300 MHz, DMSO-$d_6$) δ1.68-2.25 (8H, m), 3.19-3.28 (2H, m), 3.79-3.86 (1H, m), 3.88-3.98 (2H, m), 7.02 (1H, d, J=9.0 Hz), 7.09-7.17 (2H, m), 7.37-7.46 (2H, m), 7.74 (1H, dd, J=9.0, 2.6 Hz), 8.11 (1H, d, J=2.6 Hz).

Example 54

2-(4-(2,2-dioxido-3,4,7,8-tetrahydro-6,9-ethanopyrido[2,1-c][1,2,4]thiadiazin-9(6H)-yl)phenoxy)-5-(trifluoromethyl)benzonitrile A mixture of potassium carbonate (68 mg), 2-fluoro-5-(trifluoromethyl)benzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (45.4 mg) as white crystals.
MS (API+). found: 476.1.
$^1$H NMR (300 MHz, DMSO-$d_6$) δ1.73-1.88 (2H, m), 1.89-2.05 (4H, m), 2.07-2.25 (2H, m), 3.20-3.29 (2H, m), 3.83 (1H, brs), 3.90-4.00 (2H, m), 7.07 (1H, d, J=8.7 Hz), 7.19-7.28 (2H, m), 7.42-7.51 (2H, m), 8.02 (1H, dd, J=8.7, 1.9 Hz), 8.44 (1H, d, J=1.9 Hz).

Example 55

4-chloro-2-(4-(2,2-dioxido-3,4,7,8-tetrahydro-6,9-ethanopyrido[2,1-c][1,2,4]thiadiazin-9(6H)-yl)phenoxy)benzonitrile A mixture of potassium carbonate (68 mg), 4-chloro-2-fluorobenzonitrile (38 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (37.8 mg) as white crystals.
MS (API+). found: 442.1.
$^1$H NMR (300 MHz, DMSO-$d_6$) δ 1.74-1.87 (2H, m), 1.89-2.04 (4H, m), 2.08-2.22 (2H, m), 3.18-3.27 (2H, m), 3.78-3.87 (1H, m), 3.87-3.99 (2H, m), 7.00 (1H, d, J=1.9 Hz), 7.16 (2H, d, J=8.7 Hz), 7.36-7.48 (3H, m), 7.97 (1H, d, J=8.3 Hz).

Example 56

The compound of Example 56 can be produced by a method similar to that in Examples 1-55.

Example 57

2-(4-(2,2-dioxido-3,4,7,8-tetrahydro-6,9-ethanopyrido[2,1-c][1,2,4]thiadiazin-9(6H)-yl)phenoxy)-4-(trifluoromethyl)benzonitrile A mixture of potassium carbonate (68 mg), 2-fluoro-4-(trifluoromethyl)benzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (47.1 mg) as white crystals.
MS (API+). found: 476.1.

¹H NMR (300 MHz, DMSO-d₆) δ 1.74-1.88 (2H, m), 1.89-2.05 (4H, m), 2.09-2.24 (2H, m), 3.19-3.27 (2H, m), 3.79-3.87 (1H, m), 3.89-3.98 (2H, m), 7.14-7.22 (2H, m), 7.25 (1H, s), 7.39-7.50 (2H, m), 7.70 (1H, dd, J=8.3, 0.9 Hz), 8.20 (1H, d, J=8.3 Hz).

Example 58

3-(4-(2,2-dioxido-3,4,7,8-tetrahydro-6,9-ethano-pyrido[2,1-c][1,2,4]thiadiazin-9(6H)-yl)phenoxy)-4-(trifluoromethyl)benzonitrile A mixture of potassium carbonate (68 mg), 3-fluoro-4-(trifluoromethyl)benzonitrile (46 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight. After cooling to room temperature, water was added to the reaction mixture, and the mixture was extracted with ethyl acetate-THF mixed solvent (volume ratio 1/1). The organic layer was washed with saturated brine, and dried over anhydrous sodium sulfate. IPE was added and the precipitated crystals were collected by filtration, and dried under reduced pressure to give the title compound (46.3 mg) as white crystals.

MS (API+). found: 476.1.
¹H NMR (300 MHz, DMSO-d₆) δ 1.74-1.87 (2H, m), 1.89-2.03 (4H, m), 2.07-2.21 (2H, m), 3.20-3.27 (2H, m), 3.78-3.86 (1H, m), 3.89-3.97 (2H, m), 7.04-7.11 (2H, m), 7.37-7.44 (2H, m), 7.58 (1H, s), 7.82 (1H, d, J=8.3 Hz), 8.02 (1H, d, J=8.3 Hz).

Examples 59-64

The compounds of Examples 59-64 can be produced by a method similar to that in Examples 1-58.

Example 65

9-(4-((5-(trifluoromethyl)pyridin-2-yl)oxy)phenyl)-3,4,6,7,8,9-hexahydro-6,9-ethanopyrido[2,1-c][1,2,4]thiadiazine 2,2-dioxide A mixture of potassium carbonate (68 mg), 2-chloro-5-(trifluoromethyl)pyridine (44 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight, 2-chloro-5-(trifluoromethyl)pyridine (44 mg) was added, and the mixture was stirred at 120° C. for 2 hr. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from ethyl acetate-THF/IPE to give the title compound (42.3 mg) as white crystals.

MS (API+). found: 452.2.
¹H NMR (300 MHz, DMSO-d₆) δ 1.73-1.87 (2H, m), 1.89-2.04 (4H, m), 2.07-2.21 (2H, m), 3.18-3.28 (2H, m), 3.76-3.87 (1H, m), 3.89-4.01 (2H, m), 7.15 (2H, d, J=8.7 Hz), 7.26 (1H, d, J=8.7 Hz), 7.39 (2H, d, J=8.7 Hz), 8.24 (1H, dd, J=8.7, 2.6 Hz), 8.55-8.68 (1H, m).

Examples 66-68

The compounds of Examples 66-68 can be produced by a method similar to that in Examples 1-65.

Example 69

9-(4-((6-(trifluoromethyl)pyridin-2-yl)oxy)phenyl)-3,4,6,7,8,9-hexahydro-6,9-ethanopyrido[2,1-c][1,2,4]thiadiazine 2,2-dioxide A mixture of potassium carbonate (68 mg), 2-chloro-6-(trifluoromethyl)pyridine (44 mg), 4-(2,2-dioxido-3,4,7,8-tetrahydro-6,9-ethanopyrido[2,1-c][1,2,4]thiadiazin-9(6H)-yl)phenol (50 mg) and DMSO (2 ml) was stirred at 90° C. overnight, 2-chloro-5-(trifluoromethyl)pyridine (44 mg) was added, and the mixture was stirred at 120° C. for 6 hr. After cooling to room temperature, water was added to the reaction mixture, and the mixture was extracted with ethyl acetate-THF mixed solvent (volume ratio 1/1). The organic layer was washed with saturated brine, dried over anhydrous sodium sulfate and concentrated under reduced pressure. The obtained residue was crystallized from THF-acetonitrile/IPE to give the title compound (34.8 mg) as white crystals.

MS (API+). found: 452.1.
¹H NMR (300 MHz, DMSO-d₆) δ 1.73-1.88 (2H, m), 1.88-2.05 (4H, m), 2.09-2.23 (2H, m), 3.18-3.27 (2H, m), 3.79-3.86 (1H, m), 3.89-4.00 (2H, m), 7.11-7.21 (2H, m), 7.29 (1H, d, J=8.7 Hz), 7.35-7.46 (2H, m), 7.65 (1H, d, J=7.5 Hz), 8.07-8.19 (1H, m).

Examples 70-103

The compounds of Examples 70-103 can be produced by a method similar to that in Examples 1-69.

Example 104

9-((4-(1H-pyrazol-1-yl)phenoxy)methyl)-3,4,6,7,8,9-hexahydro-6,9-ethanopyrido[2,1-c][1,2,4]thiadiazine 2,2-dioxide A) benzyl (2-(tert-butylsulfamoyl)ethyl)carbamate To a mixture of benzyl (2-(chlorosulfonyl)ethyl)carbamate (13.0 g) and dichloromethane (500 ml) was added a mixture of t-butylamine (10 g) and dichloromethane (100 ml) at −10° C. or lower and the mixture was stirred at room temperature for 1 hr. The reaction mixture was concentrated under reduced pressure, and the residue was purified by silica gel column chromatography (ethyl acetate/petroleum ether) to give the title compound (11.0 g) as a white solid.

MS (ESI+). found: 315.0.

B) 2-amino-N-tert-butylethanesulfonamide

A mixture of benzyl (2-(tert-butylsulfamoyl)ethyl)carbamate (65 g), 10% palladium carbon (3.0 g) and methanol (500 ml) was stirred under a hydrogen atmosphere and at room temperature overnight. The reaction mixture was filtered through celite, and the filtrate was concentrated under reduced pressure to give the title compound (23 g) as a white solid.

MS (ESI+). found: 181.1.

C) diethyl 4-((2-(tert-butylsulfamoyl)ethyl)amino) cyclohexane-1,1-dicarboxylate To a mixture of diethyl 4-oxocyclohexane-1,1-dicarboxylate (10 g), 2-amino-N-tert-butylethanesulfonamide (9.5 g), acetic acid (2.5 g) and acetonitrile (500 ml) was added, under ice-cooling, sodium triacetoxyborohydride (5.0 g) and the mixture was stirred at room temperature for 2 hr. To the reaction mixture was added sodium triacetoxyborohydride (5.0 g) and the mixture was stirred at room temperature overnight, and concentrated under reduced pressure. To the residue was added ethyl acetate (500 ml), and the mixture was washed 3 times with saturated brine (50 ml). The organic layer was dried over anhydrous sodium sulfate and concentrated under reduced pressure. The residue was purified by silica gel column chromatography (ethyl acetate/hexane) to give the title compound (11.8 g) as a white solid.

MS (ESI+). found: 406.9.

D) ethyl 2-(2-(tert-butylsulfamoyl)ethyl)-3-oxo-2-azabicyclo[2.2.2]octane-4-carboxylate Diethyl 4-((2-(tert-butylsulfamoyl)ethyl)amino)cyclohexane-1,1-dicarboxylate (2.5 g) was stirred under a nitrogen atmosphere at 200° C. for 20 min. The reaction mixture was purified by silica gel column chromatography (ethyl acetate/hexane) to give the title compound (1.8 g) as a white solid.

MS (ESI+). found: 361.1.

E) N-tert-butyl-2-(4-(hydroxymethyl)-3-oxo-2-azabicyclo[2.2.2]oct-2-yl)ethanesulfonamide To a mixture of ethyl 2-(2-(tert-butylsulfamoyl)ethyl)-3-oxo-2-azabicyclo[2.2.2]octane-4-carboxylate (3.6 g) and ethanol (100 ml) was added sodium borohydride (3.8 g), and the mixture was stirred at room temperature for 2 hr. To the reaction mixture was added sodium borohydride (3.8 g) and the mixture was stirred at room temperature overnight, and concentrated under reduced pressure. The residue was purified by C18 column chromatography (methanol/10 mM aqueous ammonium carbonate solution) to give the title compound (2.64 g) as a white solid.

MS (ESI+). found: 319.2.

F) 2-(4-((benzyloxy)methyl)-3-oxo-2-azabicyclo[2.2.2]oct-2-yl)-N-tert-butylethanesulfonamide A mixture of N-tert-butyl-2-(4-(hydroxymethyl)-3-oxo-2-azabicyclo[2.2.2]oct-2-yl)ethanesulfonamide (1.2 g), 60% sodium hydride (0.3 g) and THF (50 ml) was stirred at room temperature for 30 min. To the reaction mixture was added a mixture of benzyl bromide (1 g) and THF (5 ml), and the mixture was heated under reflux for 6 hr. To the reaction mixture was added 1N hydrochloric acid to stop the reaction, and the mixture was extracted three times with ethyl acetate (100 ml). The obtained organic layer was washed with saturated brine, dried over anhydrous magnesium sulfate and concentrated under reduced pressure to give the title compound (1.46 g) as a white solid.

MS (ESI+). found: 409.2.

G) 2-(4-((benzyloxy)methyl)-3-oxo-2-azabicyclo[2.2.2]oct-2-yl)ethanesulfonamide A mixture of 2-(4-((benzyloxy)methyl)-3-oxo-2-azabicyclo[2.2.2]oct-2-yl)-N-tert-butylethanesulfonamide (6 g) and trifluoroacetic acid (15 ml) was stirred at room temperature for 12 hr, and concentrated under reduced pressure. The residue was purified by C18 column chromatography (methanol/10 mM aqueous ammonium carbonate solution) to give the title compound (3.5 g) as a white solid.

MS (ESI+). found: 353.0.

H) 9-((benzyloxy)methyl)-3,4,6,7,8,9-hexahydro-6,9-ethanopyrido[2,1-c][1,2,4]thiadiazine 2,2-dioxide A mixture of 2-(4-((benzyloxy)methyl)-3-oxo-2-azabicyclo[2.2.2]oct-2-yl)ethanesulfonamide (5 g) and phosphoryl chloride (20 ml) was heated under reflux for 1 hr, and concentrated under reduced pressure. The obtained residue was washed with methanol to give the title compound (3.86 g) as a white solid.

MS (ESI+). found: 335.0.

I) (2,2-dioxido-3,4,7,8-tetrahydro-6,9-ethanopyrido[2,1-c][1,2,4]thiadiazin-9(6H)-yl)methanol A mixture of 9-((benzyloxy)methyl)-3,4,6,7,8,9-hexahydro-6,9-ethanopyrido[2,1-c][1,2,4]thiadiazine 2,2-dioxide (3 g), 10% palladium carbon (0.5 g) and methanol (400 ml) was stirred under a hydrogen atmosphere at 46° C. for 4 hr. The reaction mixture was filtered through celite, and the filtrate was concentrated under reduced pressure to give the title compound (1.8 g) as a white solid.

MS (ESI+). found: 244.9.

J) 9-((4-(1H-pyrazol-1-yl)phenoxy)methyl)-3,4,6,7,8,9-hexahydro-6,9-ethanopyrido[2,1-c][1,2,4]thiadiazine 2,2-dioxide To a mixture of (2,2-dioxido-3,4,7,8-tetrahydro-6,9-ethanopyrido[2,1-c][1,2,4]thiadiazin-9(6H)-yl)methanol (200 mg), triethylamine (414 mg) and DMF (4 ml) was added methanesulfonyl chloride (188 mg) under ice-cooling and the mixture was stirred at room temperature for 2 hr. The reaction mixture was divided into two, cesium carbonate (534 mg) and 4-(1H-pyrazol-1-yl)phenol (216 mg) were added to one of them, and the mixture was stirred at 80° C. for 8 hr, and at 120° C. overnight. After cooling to room temperature, water was added to the reaction mixture, and the mixture was extracted with ethyl acetate-THF mixed solvent (volume ratio 1/1). Silica gel was added to the organic layer and the mixture was concentrated under reduced pressure. The residue was purified by silica gel column chromatography (methanol/ethyl acetate), and fractionated by HPLC (column: L-Column 2 ODS, mobile phase: water/acetonitrile (0.1% TFA-containing system)). The obtained residue was crystallized from THF/IPE to give the title compound (10.7 mg) as white crystals.

MS (ESI+). found: 387.2.

$^1$H NMR (300 MHz, DMSO-$d_6$) 51.52-1.66 (2H, m), 1.72-1.87 (4H, m), 1.92-2.04 (2H, m), 3.24-3.29 (2H, m), 3.73-3.80 (1H, m), 3.85-3.94 (2H, m), 4.02 (2H, s), 6.47-6.52 (1H, m), 7.02-7.10 (2H, m), 7.68 (1H, d, J=1.7 Hz), 7.71-7.78 (2H, m), 8.38 (1H, d, J=2.5 Hz).

Examples 105-124

The compounds of Examples 105-124 can be produced by a method similar to that in Examples 1-104.

The Example compounds produced by the above-mentioned methods or a method analogous thereto are shown in the following Tables. In the Tables, MS means Found.

TABLE 1

| Ex. No. | IUPAC NAME | Structural formula | salt | MS |
|---|---|---|---|---|
| 1 | 9-(4-(4-chlorophenoxy)phenyl)-3,4,6,7,8,9-hexahydro-6,9-ethanopyrido[2,1-c][1,2,4]thiadiazine 2,2-dioxide | | | 417.1 |
| 2 | 9-(4-(3-(1,1-difluoroethyl)phenoxy)phenyl)-3,4,6,7,8,9-hexahydro-6,9-ethanopyrido[2,1-c][1,2,4]-thiadiazine 2,2-dioxide | | | 447.2 |
| 3 | 9-(4-phenoxyphenyl)-3,4,6,7,8,9-hexahydro-6,9-ethanopyrido[2,1-c][1,2,4]-thiadiazine 2,2-dioxide | | | 383.1 |
| 4 | 9-(4-(4-(1,1-difluoroethyl)phenoxy)phenyl)-3,4,6,7,8,9-hexahydro-6,9-ethanopyrido[2,1-c][1,2,4]-thiadiazine 2,2-dioxide | | | 447.2 |
| 5 | 9-(4-(3,4-chlorophenoxy)phenyl)-3,4,6,7,8,9-hexahydro-6,9-ethanopyrido[2,1-c][1,2,4]-thiadiazine 2,2-dioxide | | | 417.1 |
| 6 | 9-(4-(3,4-dichlorophenoxy)phenyl)-3,4,6,7,8,9-hexahydro-6,9-ethanopyrido[2,1-c][1,2,4]-thiadiazine 2,2-dioxide | | | 451.1 |
| 7 | 9-(4-(3-chloro-4-fluorophenoxy)phenyl)-3,4,6,7,8,9-hexahydro-6,9-ethanopyrido[2,1-c][1,2,4]-thiadiazine 2,2-dioxide | | | 435.1 |

TABLE 1-continued

| Ex. No. | IUPAC NAME | Structural formula | salt | MS |
|---|---|---|---|---|
| 8 | 9-(4-(cycloheptyloxy)phenyl)-3,4,6,7,8,9-hexahydro-6,9-ethanopyrido[2,1-c][1,2,4]-thiadiazine 2,2-dioxide | 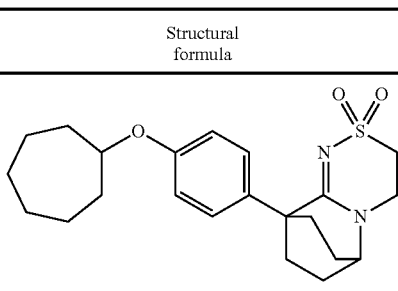 | | 403.2 |

TABLE 2

| Ex. No. | IUPAC NAME | Structural formula | salt | MS |
|---|---|---|---|---|
| 9 | 9-(4-(3-methoxyphenoxy)-phenyl)-3,4,6,7,8,9-hexahydro-6,9-ethanopyrido-[2,1-c][1,2,4]thiadiazine 2,2-dioxide | 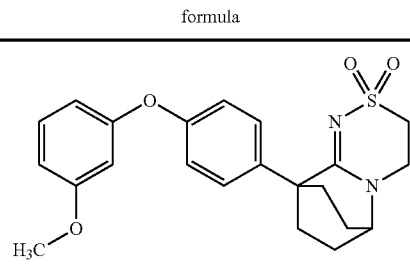 | | 413.2 |
| 10 | 9-(4-(2-chlorophenoxy)-phenyl)-3,4,6,7,8,9-hexahydro-6,9-ethanopyrido-[2,1-c][1,2,4]thiadiazine 2,2-dioxide | 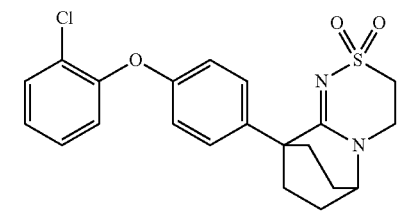 [SMILES: O=S1(=O)CCN2C(=N1)C1(c3ccc(Oc4ccccc4Cl)cc3)CCC2CC1] | | 417.1 |
| 11 | 9-(4-(2-methylphenoxy)-phenyl)-3,4,6,7,8,9-hexahydro-6,9-ethanopyrido-[2,1-c][1,2,4]thiadiazine 2,2-dioxide | 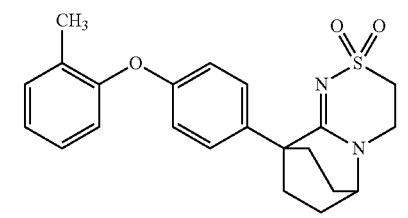 | | 397.2 |
| 13 | 9-(4-(2,3-dihydro-1-benzofuran-6-yloxy)phenyl)-3,4,6,7,8,9-hexahydro-6,9-ethanopyrido[2,1-c][1,2,4]-thiadiazine 2,2-dioxide | 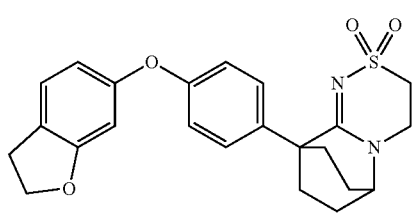 [SMILES: O=S1(=O)CCN2C(=N1)C1(c3ccc(Oc4ccc5c(c4)OCC5)cc3)CCC2CC1] | | 425.2 |
| 14 | 9-(4-(4-(trifluoromethyl)-phenoxy)phenyl)-3,4,6,7,8,9-hexahydro-6,9-ethanopyrido-[2,1-c][1,2,4]thiadiazine 2,2-dioxide | 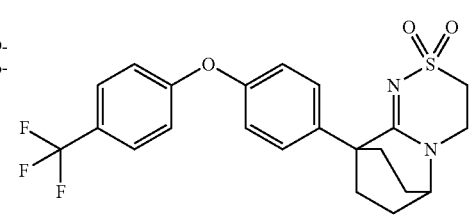 | | 451.1 |

TABLE 2-continued

| Ex. No. | IUPAC NAME | Structural formula | salt | MS |
|---|---|---|---|---|
| 15 | 9-(4-((4-(trifluoromethyl)-pyridin-2-yl)oxy)phenyl)-3,4,6,7,8,9-hexahydro-6,9-ethanopyrido[2,1-c][1,2,4]-thiadiazine 2,2-dioxide | 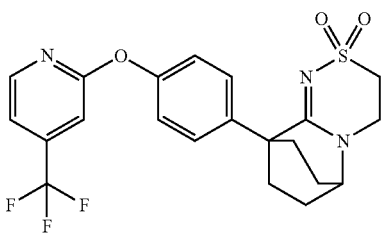 [SMILES: O=S1(=O)CCN2C(=N1)C1(c3ccc(Oc4cc(C(F)(F)F)ccn4)cc3)CCC2CC1] | | 452.2 |
| 16 | 3-(4-(2,2-dioxido-3,4,7,8-tetrahydro-6,9-ethanopyrido[2,1-c][1,2,4]thiadiazin-9(6H)-yl)phenoxy)benzonitrile | 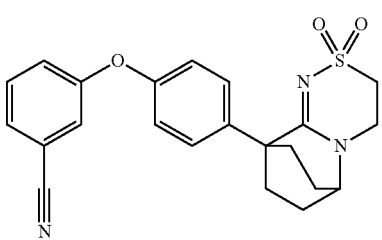 [SMILES: N#Cc1cccc(Oc2ccc(C34CCC(CC3)N3CCS(=O)(=O)N=C34)cc2)c1] | | 408.1 |
| 18 | 9-(4-(3-(difluoromethyl)-phenoxy)phenyl)-3,4,6,7,8,9-hexahydro-6,9-ethanopyrido-[2,1-c][1,2,4]thiadiazine 2,2-dioxide | 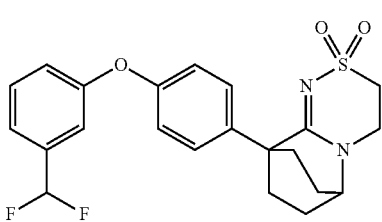 [SMILES: O=S1(=O)CCN2C(=N1)C1(c3ccc(Oc4cccc(C(F)F)c4)cc3)CCC2CC1] | | 433.1 |

TABLE 3

| Ex. No. | IUPAC NAME | Structural formula | salt | MS |
|---|---|---|---|---|
| 19 | 9-(4-(4-(difluoromethyl)-phenoxy)phenyl)-3,4,6,7,8,9-hexahydro-6,9-ethanopyrido-[2,1-c][1,2,4]thiadiazine 2,2-dioxide | 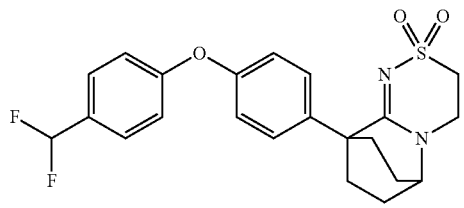 [SMILES: O=S1(=O)CCN2C(=N1)C1(c3ccc(Oc4ccc(C(F)F)cc4)cc3)CCC2CC1] | | 433.1 |
| 20 | 9-(4-(2-(trifluoromethyl)-phenoxy)phenyl)-3,4,6,7,8,9-hexahydro-6,9-ethanopyrido-[2,1-c][1,2,4]thiadiazine 2,2-dioxide | 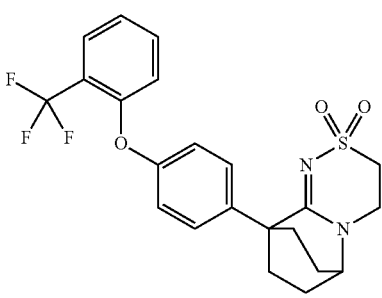 [SMILES: O=S1(=O)CCN2C(=N1)C1(c3ccc(Oc4ccccc4C(F)(F)F)cc3)CCC2CC1] | | 451.1 |

TABLE 3-continued

| Ex. No. | IUPAC NAME | Structural formula | salt | MS |
|---|---|---|---|---|
| 21 | 9-(4-((4-(trifluoromethyl)-pyridin-3-yl)oxy)phenyl)-3,4,6,7,8,9-hexahydro-6,9-ethanopyrido[2,1-c][1,2,4]-thiadiazine 2,2-dioxide | 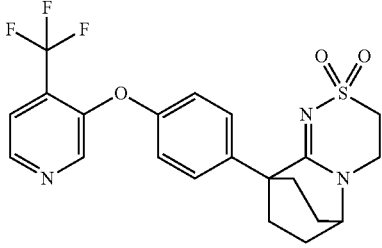 [SMILES: O=S1(=O)CCN2C(=N1)C1(c3ccc(Oc4cnccc4C(F)(F)F)cc3)CCC2CC1] | | 452.1 |
| 22 | 9-(4-((3-fluoro-5-(trifluoromethyl)pyridin-2-yl)oxy)phenyl)-3,4,6,7,8,9-hexahydro-6,9-ethanopyrido-[2,1-c][1,2,4]thiadiazine 2,2-dioxide | 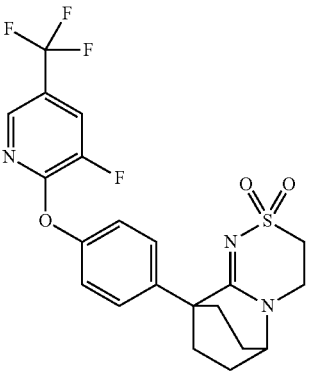 [SMILES: O=S1(=O)CCN2C(=N1)C1(c3ccc(Oc4ncc(C(F)(F)F)cc4F)cc3)CCC2CC1] | | 470.1 |
| 23 | 9-(4-(pyrimidin-2-yloxy)phenyl)-3,4,6,7,8,9-hexahydro-6,9-ethanopyrido[2,1-c][1,2,4]thiadiazine 2,2-dioxide | 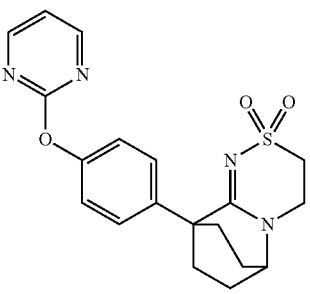 [SMILES: O=S1(=O)CCN2C(=N1)C1(c3ccc(Oc4ncccn4)cc3)CCC2CC1] | | 385.1 |
| 24 | 9-(4-((2,6-dimethylpyridin-4-yl)oxy)phenyl)-3,4,6,7,8,9-hexahydro-6,9-ethanopyrido[2,1-c][1,2,4]-thiadiazine 2,2-dioxide | 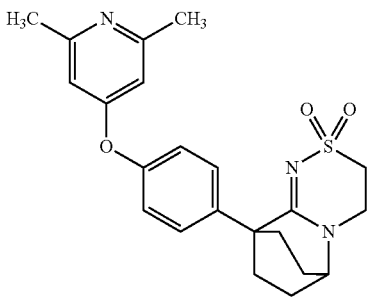 [SMILES: Cc1cc(Oc2ccc(C34CCC(CC3)N3CCS(=O)(=O)N=C34)cc2)cc(C)n1] | | 412.1 |

TABLE 3-continued

| Ex. No. | IUPAC NAME | Structural formula | salt | MS |
|---|---|---|---|---|
| 25 | 9-(4-((3-chloro-5-(trifluoromethyl)pyridin-2-yl)oxy)phenyl)-3,4,6,7,8,9-hexahydro-6,9-ethanopyrido[2,1-c][1,2,4]thiadiazine 2,2-dioxide | | | 486.1 |
| 26 | 9-(4-(2,2,2-trifluoroethoxy)phenyl)-3,4,6,7,8,9-hexahydro-6,9-ethanopyrido[2,1-c][1,2,4]-thiadiazine 2,2-dioxide | | | 389.1 |

TABLE 4

| Ex. No. | IUPAC NAME | Structural formula | salt | MS |
|---|---|---|---|---|
| 27 | 9-(4-butoxyphenyl)-3,4,6,7,8,9-hexahydro-6,9-ethanopyrido[2,1-c][1,2,4]thiadiazine 2,2-dioxide | | | 363.1 |
| 28 | 9-(4-isobutoxyphenyl)-3,4,6,7,8,9-hexahydro-6,9-ethanopyrido[2,1-c][1,2,4]thiadiazine 2,2-dioxide | | | 363.1 |

TABLE 4-continued

| Ex. No. | IUPAC NAME | Structural formula | salt | MS |
|---|---|---|---|---|
| 30 | 9-(4-((3-chlorobenzyl)oxy)phenyl)-3,4,6,7,8,9-hexahydro-6,9-ethanopyrido[2,1-c][1,2,4]thiadiazine 2,2-dioxide | | | 431.1 |
| 32 | 9-(4-sec-butoxyphenyl)-3,4,6,7,8,9-hexahydro-6,9-ethanopyrido[2,1-c][1,2,4]thiadiazine 2,2-dioxide | | | 363.1 |
| 33 | 9-(4-(benzyloxy)phenyl)-3,4,6,7,8,9-hexahydro-6,9-ethanopyrido[2,1-c][1,2,4]thiadiazine 2,2-dioxide | | | 397.1 |
| 34 | 9-(4-((2-chlorobenzyl)oxy)phenyl)-3,4,6,7,8,9-hexahydro-6,9-ethanopyrido[2,1-c][1,2,4]thiadiazine 2,2-dioxide | | | 431.1 |
| 35 | 9-(4-((3-fluorobenzyl)oxy)phenyl)-3,4,6,7,8,9-hexahydro-6,9-ethanopyrido[2,1-c][1,2,4]thiadiazine 2,2-dioxide | | | 415.1 |

TABLE 4-continued

| Ex. No. | IUPAC NAME | Structural formula | salt | MS |
|---|---|---|---|---|
| 36 | 9-(4-(2-methoxyethoxy)-phenyl)-3,4,6,7,8,9-hexahydro-6,9-ethanopyrido-[2,1-c][1,2,4]thiadiazine 2,2-dioxide | | | 365.1 |

TABLE 5

| Ex. No. | IUPAC NAME | Structural formula | salt | MS |
|---|---|---|---|---|
| 38 | 9-(4-(tetahydrofuran-2-ylmethoxy)phenyl)-3,4,6,7,8,9-hexahydro-6,9-ethanopyrido[2,1-c][1,2,4]-thiadiazine 2,2-dioxide | | | 391.1 |
| 39 | 9-(4-((3,5-dimethyl-1,2-oxazol-4-yl)methoxy)phenyl)-3,4,6,7,8,9-hexahydro-6,9-ethanopyrido[2,1-c][1,2,4]-thiadiazine 2,2-dioxide | | | 416.1 |
| 40 | 9-(4-(4-chloro-2-methoxyphenoxy)phenyl)-3,4,6,7,8,9-hexahydro-6,9-ethanopyrido[2,1-c][1,2,4]-thiadiazine 2,2-dioxide | | | 447.1 |
| 41 | 9-(4-((2,2-difluoro-1,3-benzodioxol-5-yl)oxy)-phenyl)-3,4,6,7,8,9-hexahydro-6,9-ethanopyrido-[2,1-c][1,2,4]thiadiazine 2,2-dioxide | | | 463 |

TABLE 5-continued

| Ex. No. | IUPAC NAME | Structural formula | salt | MS |
|---|---|---|---|---|
| 44 | 9-(4-phenoxyphenyl)-3,4,6,7,8,9-hexahydropyrimido[2,1-c][1,2,4]thiadiazine 2,2-dioxide | | | 358.1 |
| 45 | 9-(4-(4-chlorophenoxy)-phenyl)-3,4,6,7,8,9-hexahydropyrimido[2,1-c][1,2,4]thiadiazine 2,2-dioxide | | | 392.1 |
| 46 | 5-bromo-2-(4-(2,2-dioxido-3,4,7,8-tetrahydro-6,9-ethanopyrido[2,1-c][1,2,4]thiadiazin-9(6H)-yl)phenoxy)benzonitrile | | | 486.1, 488.1 |
| 47 | 5-(4-(2,2-dioxido-3,4,7,8-tetrahydro-6,9-ethanopyrido[2,1-c][1,2,4]thiadiazin-9(6H)-yl)phenoxy)-2-methylbenzonitrile | | | 422.2 |

TABLE 6

| Ex. No. | IUPAC NAME | Structural formula | salt | MS |
|---|---|---|---|---|
| 48 | 2-chloro-4-(4-(2,2-dioxido-3,4,7,8-tetrahydro-6,9-ethanopyrido[2,1-c][1,2,4]thiadiazin-9(6H)-yl)phenoxy)benzonitrile | | | 442.1 |
| 49 | 2-chloro-5-(4-(2,2-dioxido-3,4,7,8-tetrahydro-6,9-ethanopyrido[2,1-c][1,2,4]thiadiazin-9(6H)-yl)phenoxy)benzonitrile | | | |

TABLE 6-continued

| Ex. No. | IUPAC NAME | Structural formula | salt | MS |
|---|---|---|---|---|
| 50 | 2,6-dichloro-4-(4-(2,2-dioxido-3,4,7,8-tetahydro-6,9-ethanopyrido[2,1-c][1,2,4]thiadiazin-9(6H)-yl)phenoxy)benzonitrile | | | |
| 51 | 5-(4-(2,2-dioxido-3,4,7,8-tetrahydro-6,9-ethanopyrido-[2,1-c][1,2,4]thiadiazin-9(6H)-yl)phenoxy)-2-(trifluoromethyl)benzonitrile | | | 476.1 |
| 52 | 4-(4-(2,2-dioxido-3,4,7,8-tetrahydro-6,9-ethanopyrido-[2,1-c][1,2,4]thiadiazin-9(6H)-yl)phenoxy)-2-(trifluoromethyl)benzonitrile | | | 476.1 |
| 53 | 5-chloro-2-(4-(2,2-dioxido-3,4,7,8-tetrahydro-6,9-ethanopyrido[2,1-c][1,2,4]thiadiazin-9(6H)-yl)phenoxy)benzonitrile | | | 442.1 |
| 54 | 2-(4-(2,2-dioxido-3,4,7,8-tetrahydro-6,9-ethanopyrido-[2,1-c][1,2,4]thiadiazin-9(6H)-yl)phenoxy)-5-(trifluoromethyl)benzonitrile | | | 476.1 |
| 55 | 4-chloro-2-(4-(2,2-dioxido-3,4,7,8-tetrahydro-6,9-ethanopyrido[2,1-c][1,2,4]thiadiazin-9(6H)-yl)phenoxy)benzonitrile | | | 442.1 |

TABLE 7

| Ex. No. | IUPAC NAME | Structural formula | salt | MS |
|---|---|---|---|---|
| 56 | 4-chloro-3-(4-(2,2-dioxido-3,4,7,8-tetrahydro-6,9-ethanopyrido[2,1-c][1,2,4]thiadiazin-9(6H)-yl)phenoxy)benzonitrile | | | |
| 57 | 2-(4-(2,2-dioxo-3,4,7,8-tetrahydro-6,9-ethanopyrido-[2,1-c][1,2,4]thiadiazin-9(6H)-yl)phenoxy)-4-(trifluoromethyl)benzonitrile | | | 476.1 |
| 58 | 3-(4-(2,2-dioxido-3,4,7,8-tetrahydro-6,9-ethanopyrido-[2,1-c][1,2,4]thiadiazin-9(6H)-yl)phenoxy)-4-(trifluoromethyl)benzonitrile | | | 476.1 |
| 59 | 9-(4-(3-fluoro-4-(trifluoromethyl)phenoxy)phenyl)-3,4,6,7,8,9-hexahydro-6,9-ethanopyrido[2,1-c][1,2,4]-thiadiazine 2,2-dioxide | | | |
| 60 | 9-(4-(3-chloro-4-(trifluoromethyl)phenoxy)phenyl)-3,4,6,7,8,9-hexahydro-6,9-ethanopyrido[2,1-c][1,2,4]-thiadiazine 2,2-dioxide | | | |
| 61 | 9-(4-(3-(trifluoromethyl)phenoxy)phenyl)-3,4,6,7,8,9-hexahydro-6,9-ethanopyrido-[2,1-c][1,2,4]thiadiazine 2,2-dioxide | | | |

TABLE 7-continued

| Ex. No. | IUPAC NAME | Structural formula | salt | MS |
|---|---|---|---|---|
| 62 | 9-(4-(4-chloro-3-(trifluoro-methyl)phenoxy)phenyl)-3,4,6,7,8,9-hexahydro-6,9-ethanopyrido[2,1-c][1,2,4]-thiadiazine 2,2-dioxide | | | |
| 63 | 9-(4-(4-fluoro-3-(trifluoro-methyl)phenoxy)phenyl)-3,4,6,7,8,9-hexahydro-6,9-ethanopyrido[2,1-c][1,2,4]-thiadiazine 2,2-dioxide | | | |

TABLE 8

| Ex. No. | IUPAC NAME | Structural formula | salt | MS |
|---|---|---|---|---|
| 64 | 9-(4-((5-chloropyridin-2-yl)oxy)phenyl)-3,4,6,7,8,9-hexahydro-6,9-ethanopyrido-[2,1-c][1,2,4]thiadiazine 2,2-dioxide | | | |
| 65 | 9-(4-((5-(trifluoromethyl)-pyridin-2-yl)oxy)phenyl)-3,4,6,7,8,9-hexahydro-6,9-ethanopyrido[2,1-c][1,2,4]-thiadiazine 2,2-dioxide | | | 452.2 |
| 66 | 9-(4-((5-methyl-2-thienyl)-oxy)phenyl)-3,4,6,7,8,9-hexahydro-6,9-ethanopyrido-[2,1-c][1,2,4]thiadiazine 2,2-dioxide | | | |
| 67 | 9-(4-((5-chloro-2-thienyl)-oxy)phenyl)-3,4,6,7,8,9-[2,1-c][1,2,4]thiadiazine 2,2-dioxide | | | |

TABLE 8-continued

| Ex. No. | IUPAC NAME | Structural formula | salt | MS |
|---|---|---|---|---|
| 68 | 5-(4-(2,2-dioxido-3,4,7,8-tetrahydro-6,9-ethanopyrido-[2,1-c][1,2,4]thiadiazin-9(6H)-yl)phenoxy)thiophene-2-carbonitrile | | | |
| 69 | 9-(4-((6-(trifluoromethyl)-pyridin-2-yl)oxy)phenyl)-3,4,6,7,8,9-hexahydro-6,9-ethanopyrido[2,1-c][1,2,4]-thiadiazine 2,2-dioxide | | | 452.1 |
| 70 | 9-(biphenyl-4-yl)-3,4,6,7,8,9-hexahydro-6,9-ethanopyrido[2,1-c][1,2,4]thiadiazine 2,2-dioxide | | | |
| 71 | 9-(3'-chlorobiphenyl-4-yl)-3,4,6,7,8,9-hexahydro-6,9-ethanopyrido[2,1-c][1,2,4]thiadiazine 2,2-dioxide | | | |

TABLE 9

| Ex. No. | IUPAC NAME | Structural formula | salt | MS |
|---|---|---|---|---|
| 72 | 9-(3'-methoxybiphenyl-4-yl)-3,4,6,7,8,9-hexahydro-6,9-ethanopyrido[2,1-c][1,2,4]thiadiazine 2,2-dioxide | | | |

TABLE 9-continued

| Ex. No. | IUPAC NAME | Structural formula | salt | MS |
|---|---|---|---|---|
| 73 | 4'-(2,2-dioxido-3,4,7,8-tetrahydro-6,9-ethanopyrido[2,1-c][1,2,4]thiadiazin-9(6H)-yl)biphenyl-3-carbonitrile | | | |
| 74 | 9-(4-(3,4-dichlorophenoxy)-phenyl)-3,4,6,7,8,9-hexahydropyrimido[2,1-c][1,2,4]thiadiazine 2,2-dioxide | | | |
| 75 | 9-(4-(3-chlorophenoxy)-phenyl)-3,4,6,7,8,9-hexahydropyrimido[2,1-c][1,2,4]thiadiazine 2,2-dioxide | | | |
| 76 | 9-(4-(4-(trifluoromethyl)-phenoxy)phenyl)-3,4,6,7,8,9-hexahydropyrimido[2,1-c][1,2,4]thiadiazine 2,2-dioxide | | | |
| 77 | 9-(4-(3-(trifluoromethyl)-phenoxy)phenyl)-3,4,6,7,8,9-hexahydropyrimido[2,1-c][1,2,4]thiadiazine 2,2-dioxide | | | |
| 78 | 9-(4-(4-(1,1-difluoroethyl)-phenoxy)phenyl)-3,4,6,7,8,9-hexahydropyrimido[2,1-c][1,2,4]thiadiazine 2,2-dioxide | | | |

TABLE 9-continued

| Ex. No. | IUPAC NAME | Structural formula | salt | MS |
|---|---|---|---|---|
| 79 | 9-(4-(3,4-dichlorophenoxy)-phenyl)-7,7-dimethyl-3,4,6,7,8,9-hexahydro-pyrimido[2,1-c][1,2,4]-thiadiazine 2,2-dioxide | | | |

TABLE 10

| Ex. No. | IUPAC NAME | Structural formula | salt | MS |
|---|---|---|---|---|
| 80 | 9-(4-(3-chlorophenoxy)-phenyl)-7,7-dimethyl-3,4,6,7,8,9-hexahydro-pyrimido[2,1-c][1,2,4]-thiadiazine 2,2-dioxide | | | |
| 81 | 7,7-dimethyl-9-(4-(4-(trifluoromethyl)phenoxy)phenyl)-3,4,6,7,8,9-hexa-hydropyrimido[2,1-c][1,2,4]-thiadiazine 2,2-dioxide | | | |
| 82 | 7,7-dimethyl-9-(4-(3-(trifluoromethyl)phenoxy)-phenyl)-3,4,6,7,8,9-hexahydropyrimido[2,1-c][1,2,4]thiadiazine 2,2-dioxide | | | |
| 83 | 9-(4-(4-(1,1-difluoroethyl)-phenoxy)phenyl)-7,7-dimethyl-3,4,6,7,8,9-hexa-hydropyrimido[2,1-c][1,2,4]-thiadiazine 2,2-dioxide | | | |

TABLE 10-continued

| Ex. No. | IUPAC NAME | Structural formula | salt | MS |
|---|---|---|---|---|
| 84 | 7,7-dimethyl-9-(4-phenoxyphenyl)-3,4,6,7,8,9-hexahydropyrimido[2,1-c][1,2,4]thiadiazine 2,2-dioxide | | | |
| 85 | 9-(4-(4-chlorophenoxy)phenyl)-7,7-dimethyl-3,4,6,7,8,9-hexahydropyrimido[2,1-c][1,2,4]thiadiazine 2,2-dioxide | | | |
| 86 | 9-(6-phenoxypyridin-3-yl)-3,4,6,7,8,9-hexahydro-6,9-ethanopyrimido[2,1-c][1,2,4]thiadiazine 2,2-dioxide | | | |
| 87 | 9-(6-(4-chlorophenoxy)pyridin-3-yl)-3,4,6,7,8,9-hexahydro-6,9-ethanopyrido[2,1-c][1,2,4]thiadiazine 2,2-dioxide | | | |

TABLE 11

| Ex. No. | IUPAC NAME | Structural formula | salt | MS |
|---|---|---|---|---|
| 88 | 9-(6-(3,4-dichlorophenoxy)pyridin-3-yl)-3,4,6,7,8,9-hexahydro-6,9-ethanopyrido[2,1-c][1,2,4]thiadiazine 2,2-dioxide | | | |
| 89 | 9-(6-(4-(trifluoromethyl)phenoxy)pyridin-3-yl)-3,4,6,7,8,9-hexahydro-6,9-ethanopyrido[2,1-c][1,2,4]thiadiazine 2,2-dioxide | | | |

TABLE 11-continued

| Ex. No. | IUPAC NAME | Structural formula | salt | MS |
|---|---|---|---|---|
| 90 | 9-(6-(4-(1,1-difluoroethyl)-phenoxy)pyridin-3-yl)-3,4,6,7,8,9-hexahydro-6,9-ethanopyrido[2,1-c][1,2,4]-thiadiazine 2,2-dioxide | | | |
| 91 | 9-(5-phenoxypyridin-2-yl)-3,4,6,7,8,9-hexahydro-6,9-ethanopyrido[2,1-c][1,2,4]-thiadiazine 2,2-dioxide | | | |
| 92 | 9-(5-(4-chlorophenoxy)-pyridin-2-yl)-3,4,6,7,8,9-hexahydro-6,9-ethanopyrido-[2,1-c][1,2,4]thiadiazine 2,2-dioxide | | | |
| 93 | 9-(5-(3,4-dichlorophenoxy)-pyridin-2-yl)-3,4,6,7,8,9-hexahydro-6,9-ethanopyrido-[2,1-c][1,2,4]thiadiazine 2,2-dioxide | | | |
| 94 | 9-(5-(4-(trifluoromethyl)-phenoxy)pyridin-2-yl)-3,4,6,7,8,9-hexahydro-6,9-ethanopyrido[2,1-c][1,2,4]-thiadiazine 2,2-dioxide | | | |
| 95 | 9-(5-(4-(1,1-difluoroethyl)-phenoxy)pyridin-2-yl)-3,4,6,7,8,9-hexahydro-6,9-ethanopyrido[2,1-c][1,2,4]-thiadiazine 2,2-dioxide | | | |

TABLE 12

| Ex. No. | IUPAC NAME | Structural formula | salt | MS |
|---|---|---|---|---|
| 96 | 9-(6-((5-chloro-2-thienyl)-oxy)pyridin-3-yl)-3,4,6,7,8,9-hexahydro-6,9-ethanopyrido[2,1-c][1,2,4]-thiadiazine 2,2-dioxide | | | |
| 97 | 9-(5-((5-chloro-2-thienyl)oxy)pyridin-2-yl)-3,4,6,7,8,9-hexahydro-6,9-ethanopyrido[2,1-c][1,2,4]-thiadiazine 2,2-dioxide | | | |
| 98 | 9-(6-((5-methyl-2-thienyl)oxy)pyridin-3-yl)-3,4,6,7,8,9-hexahydro-6,9-ethanopyrido[2,1-c][1,2,4]-thiadiazine 2,2-dioxide | | | |
| 99 | 9-(5-((5-methyl-2-thienyl)-oxy)pyridin-2-yl)-3,4,6,7,8,9-hexahydro-6,9-ethanopyrido[2,1-c][1,2,4]-thiadiazine 2,2-dioxide | | | |
| 100 | 9-((biphenyl-4-yloxy)methyl)-3,4,6,7,8,9-hexahydro-6,9-ethanopyrido-[2,1-c][1,2,4]thiadiazine 2,2-dioxide | | | |
| 101 | 4'-((2,2-dioxido-3,4,7,8-tetrahydro-6,9-ethanopyrido-[2,1-c][1,2,4]thiadiazin-9(6H)-yl)methoxy)biphenyl-2-carbonitrile | | | |

TABLE 12-continued

| Ex. No. | IUPAC NAME | Structural formula | salt | MS |
|---|---|---|---|---|
| 102 | 4'-((2,2-dioxido-3,4,7,8-tetrahydro-6,9-ethanopyrido-[2,1-c][1,2,4]thiadiazin-9(6H)-yl)methoxy)biphenyl-3-carbonitrile | | | |
| 103 | 9-((4-(4-chloro-1H-pyrazol-1-yl)phenoxy)methyl)-3,4,6,7,8,9-hexahydro-6,9-ethanopyrido[2,1-c][1,2,4]-thiadiazine 2,2-dioxide | | | |

TABLE 13

| Ex. No. | IUPAC NAME | Structural formula | salt | MS |
|---|---|---|---|---|
| 104 | 9-((4-(1H-pyrazol-1-yl)phenoxy)methyl)-3,4,6,7,8,9-hexahydro-6,9-ethanopyrido[2,1-c][1,2,4]-thiadiazine 2,2-dioxide | | | 387.2 |
| 105 | 4'-((2,2-dioxido-3,4,7,8-tetrahydro-6,9-ethanopyrido-[2,1-c][1,2,4]thiadiazin-9(6H)-yl)methoxy)-4-fluoro-biphenyl-2-carbonitrile | | | |

TABLE 13-continued

| Ex. No. | IUPAC NAME | Structural formula | salt | MS |
|---|---|---|---|---|
| 106 | 9-((4-(pyridin-2-yl)-phenoxy)methyl)-3,4,6,7,8,9-hexahydro-6,9-ethanopyrido-[2,1-c][1,2,4]thiadiazine 2,2-dioxide | | | |
| 107 | 6-(4-((2,2-dioxido-3,4,7,8-tetrahydro-6,9-ethanopyrido-[2,1-c][1,2,4]thiadiazin-9(6H)-yl)methoxy)phenyl)-nicotinonitrile | | | |
| 108 | 9-((4-(5-chloropyridin-2-yl)phenoxy)methyl)-3,4,6,7,8,9-hexahydro-6,9-ethanopyrido[2,1-c][1,2,4]-thiadiazine 2,2-dioxide | | | |
| 109 | 9-((4-(5-fluoropyridin-2-yl)phenoxy)methyl)-3,4,6,7,8,9-hexahydro-6,9-ethanopyrido[2,1-c][1,2,4]-thiadiazine 2,2-dioxide | | | |
| 110 | 6-(4-((2,2-dioxido-3,4,7,8-tetrahydro-6,9-ethanopyrido-[2,1-c][1,2,4]thiadiazin-9(6H)-yl)methoxy)phenyl)-5-fluoronicotinonitrile | | | |

TABLE 13-continued

| Ex. No. | IUPAC NAME | Structural formula | salt | MS |
|---|---|---|---|---|
| 111 | 9-((4-(5-chloro-3-fluoropyridin-2-yl)phenoxy)-methyl)-3,4,6,7,8,9-hexahydro-6,9-ethanopyrido-[2,1-c][1,2,4]thiadiazine 2,2-dioxide | | | |

TABLE 14

| Ex. No. | IUPAC NAME | Structural formula | salt | MS |
|---|---|---|---|---|
| 112 | 6-(4-((2,2-dioxido-3,4,7,8-tetahydro-6,9-ethanopyrido-[2,1-c][1,2,4]thiadiazin-9(6H)-yl)methoxy)-3-fluorophenyl)nicotinonitrile | | | |
| 113 | 9-((4-(5-chloropyridin-2-yl)-2-fluorophenoxy)methyl)-3,4,6,7,8,9-hexahydro-6,9-ethanopyrido[2,1-c][1,2,4]-thiadiazine 2,2-dioxide | | | |
| 114 | 2-(4-((2,2-dioxido-3,4,7,8-tetahydro-6,9-ethanopyrido-[2,1-c][1,2,4]thiadiazin-9(6H)-yl)methoxy)phenyl)-pyrimidine-5-carbonitrile | | | |

TABLE 14-continued

| Ex. No. | IUPAC NAME | Structural formula | salt | MS |
|---|---|---|---|---|
| 115 | 9-((4-(5-chloropyrimidin-2-yl)phenoxy)methyl)-3,4,6,7,8,9-hexahydro-6,9-ethanopyrido[2,1-c][1,2,4]-thiadiazine 2,2-dioxide | | | |
| 116 | 9-((4-(5-fluoropyrimidin-2-yl)phenoxy)methyl)-3,4,6,7,8,9-hexahydro-6,9-ethanopyrido[2,1-c][1,2,4]-thiadiazine 2,2-dioxide | | | |
| 117 | 9-((4-(4-methoxy-1H-pyrazol-1-yl)phenoxy)methyl)-3,4,6,7,8,9-hexahydro-6,9-ethanopyrido[2,1-c][1,2,4]-thiadiazine 2,2-dioxide | | | |
| 118 | 9-((4-(4-(trifluoromethyl)-1H-pyrazol-1-yl)phenoxy)methyl)-3,4,6,7,8,9-hexahydro-6,9-ethanopyrido[2,1-c][1,2,4]-thiadiazine 2,2-dioxide | | | |
| 119 | 5-(4-((2,2-dioxido-3,4,7,8-tetrahydro-6,9-ethanopyrido-[2,1-c][1,2,4]thiadiazin-9(6H)-yl)methoxy)phenyl)-thiophene-2-carbonitrile | | | |

TABLE 15

| Ex. No. | IUPAC NAME | Structural formula | salt | MS |
|---|---|---|---|---|
| 120 | 4'-((2,2-dioxido-3,4,7,8-tetrahydro-6,9-ethanopyrido[2,1-c][1,2,4]thiadiazin-9(6H)-yl)methoxy)biphenyl-4-carbonitrile | 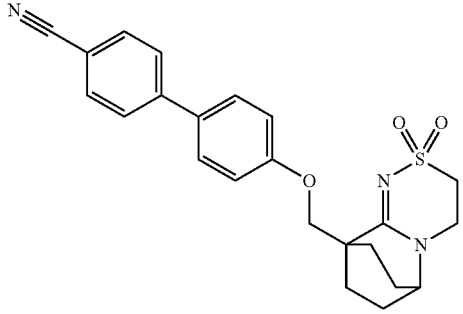 [SMILES: N#Cc1ccc(-c2ccc(OCC34CCC(CC3)N3CCS(=O)(=O)N=C34)cc2)cc1] | | |
| 121 | 1-(4-((2,2-dioxido-3,4,7,8-tetrahydro-6,9-ethanopyrido[2,1-c][1,2,4]thiadiazin-9(6H)-yl)methoxy)phenyl)pyrrolidin-2-one | 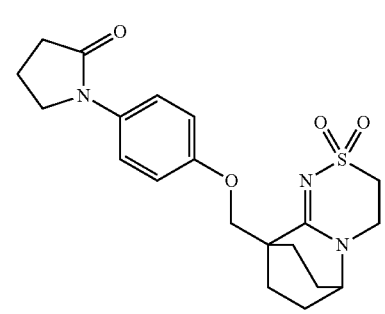 [SMILES: O=C1CCCN1c1ccc(OCC23CCC(CC2)N2CCS(=O)(=O)N=C23)cc1] | | |
| 122 | 1-(4-((2,2-dioxido-3,4,7,8-tetrahydro-6,9-ethanopyrido[2,1-c][1,2,4]thiadiazin-9(6H)-yl)methoxy)phenyl)-3,3-difluoropyrrolidin-2-one | 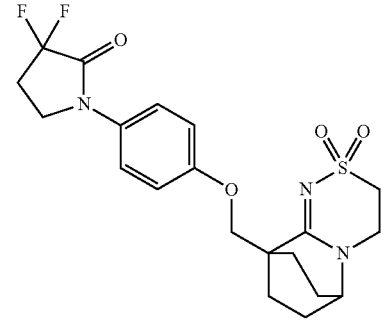 [SMILES: O=C1N(c2ccc(OCC34CCC(CC3)N3CCS(=O)(=O)N=C34)cc2)CCC1(F)F] | | |
| 123 | 9-((4-(tetrahydro-2H-pyran-4-yl)phenoxy)methyl)-3,4,6,7,8,9-hexahydro-6,9-ethanopyrido[2,1-c][1,2,4]thiadiazine 2,2-dioxide | 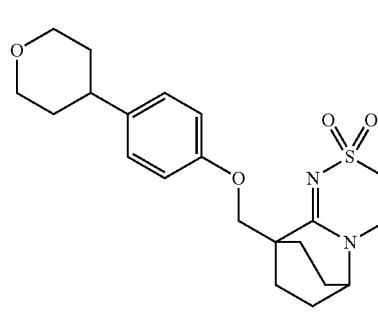 | | |
| 124 | 6-(4-((2,2-dioxido-3,4,7,8-tetrahydro-6,9-ethanopyrido[2,1-c][1,2,4]thiadiazin-9(6H)-yl)methoxy)phenyl)-2-methyl-4,5-dihydropyridazin-3(2H)-one | 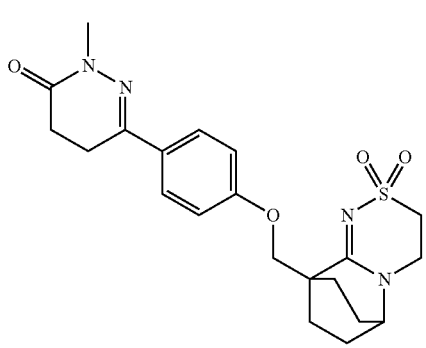 [SMILES: CN1N=C(c2ccc(OCC34CCC(CC3)N3CCS(=O)(=O)N=C34)cc2)CCC1=O] | | |

In addition, the Reference Example compounds are shown in the following Tables.

TABLE 16-1

| Ref. Ex. No. | chemical name |
|---|---|
| 1 | 9-(biphenyl-4-yl)-3,4-dihydropyridazino[6,1-c][1,2,4]thiadiazine 2,2-dioxide |
| 2 | 9-(4-phenoxyphenyl)-3,4-dihydropyridazino[6,1-c][1,2,4]thiadiazine 2,2-dioxide |
| 3 | 9-(4-(4-chloro-1H-pyrazol-1-yl)phenyl)-3,4-dihydro-pyridazino[6,1-c][1,2,4]thiadiazine 2,2-dioxide |
| 4 | 9-(4-(4-methyl-1H-imidazol-1-yl)phenyl)-3,4-dihydro-pyridazino[6,1-c][1,2,4]thiadiazine 2,2-dioxide |
| 5 | 9-(5-phenylpyridin-2-yl)-3,4-dihydropyridazino[6,1-c][1,2,4]thiadiazine 2,2-dioxide |
| 6 | 9-(4-(pyridin-2-yl)phenyl)-3,4-dihydropyridazino[6,1-c][1,2,4]thiadiazine 2,2-dioxide |
| 7 | 9-(2-fluorobiphenyl-4-yl)-3,4-dihydropyridazino[6,1-c][1,2,4]thiadiazine 2,2-dioxide |
| 8 | 9-(4-(tetrahydro-2H-pyran-4-yl)phenyl)-3,4-dihydro-pyridazino[6,1-c][1,2,4]thiadiazine 2,2-dioxide |
| 9 | 9-(2-naphthyl)-3,4-dihydropyridazino[6,1-c][1,2,4]thiadiazine 2,2-dioxide |
| 10 | 9-(6-methoxy-2-naphthyl)-3,4-dihydropyridazino[6,1-c][1,2,4]thiadiazine 2,2-dioxide |
| 11 | 9-(1-methyl-1H-indol-5-yl)-3,4-dihydropyridazino[6,1-c][1,2,4]thiadiazine 2,2-dioxide |
| 12 | 9-(4-(4-chlorophenoxy)phenyl)-3,4-dihydropyridazino-[6,1-c][1,2,4]thiadiazine 2,2-dioxide |
| 13 | 9-(4-(3,4-dichlorophenoxy)phenyl)-3,4-dihydropyridazino[6,1-c][1,2,4]thiadiazine 2,2-dioxide |
| 14 | 9-(4-(3-(trifluoromethyl)phenoxy)phenyl)-3,4-dihydropyridazino[6,1-c][1,2,4]thiadiazine 2,2-dioxide |
| 15 | 9-(5-phenoxypyridin-2-yl)-3,4-dihydropyridazino[6,1-c][1,2,4]thiadiazine 2,2-dioxide |
| 16 | 9-(6-phenoxypyridin-3-yl)-3,4-dihydropyridazino[6,1-c][1,2,4]thiadiazine 2,2-dioxide |
| 17 | 9-(4-(pyridin-2-yloxy)phenyl)-3,4-dihydropyridazino-[6,1-c][1,2,4]thiadiazine 2,2-dioxide |
| 18 | 9-(4-((4-(trifluoromethyl)pyridin-2-yl)oxy)phenyl)-3,4-dihydropyridazino[6,1-c][1,2,4]thiadiazine 2,2-dioxide |
| 19 | 9-(4-(cyclohexyloxy)phenyl)-3,4-dihydropyridazino[6,1-c][1,2,4]thiadiazine 2,2-dioxide |
| 20 | 9-(4-(tetrahydro-2H-pyran-4-yloxy)phenyl)-3,4-dihydropyridazino[6,1-c][1,2,4]thiadiazine 2,2-dioxide |
| 21 | 9-(4-((4,4-difluorocyclohexyl)oxy)phenyl)-3,4-dihydropyridazino[6,1-c][1,2,4]thiadiazine 2,2-dioxide |
| 22 | 9-(4-(2,2-dimethylpropoxy)phenyl)-3,4-dihydro-pyridazino[6,1-c][1,2,4]thiadiazine 2,2-dioxide |
| 23 | 9-(4-(trifluoromethoxy)phenyl)-3,4-dihydro-pyridazino[6,1-c][1,2,4]thiadiazine 2,2-dioxide |
| 24 | 9-(4-((3-fluorobenzyl)oxy)phenyl)-3,4-dihydro-pyridazino[6,1-c][1,2,4]thiadiazine 2,2-dioxide |
| 25 | 8-(biphenyl-4-yl)-6-chloro-3,4-dihydro-1H-2,1-benzothiazine 2,2-dioxide |

TABLE 16-2

| | |
|---|---|
| 26 | 6-chloro-8-(4-phehoxyphenyl)-3,4-dihydro-1H-2,1-benzothiazine 2,2-dioxide |
| 27 | 6-chloro-8-(4-(4-chloro-1H-pyrazol-1-yl)phenyl)-3,4-dihydro-1H-2,1-benzothiazine 2,2-dioxide |
| 28 | 6-chloro-8-(4-(4-methyl-1H-imidazol-1-yl)phenyl)-3,4-dihydro-1H-2,1-benzothiazine 2,2-dioxide |
| 29 | 6-chloro-8-(5-phenylpyridin-2-yl)-3,4-dihydro-1H-2,1-benzothiazine 2,2-dioxide |
| 30 | 6-chloro-8-(4-(pyridin-2-yl)phenyl)-3,4-dihydro-1H-2,1-benzothiazine 2,2-dioxide |
| 31 | 6-chloro-8-(2-fluorobiphenyl-4-yl)-3,4-dihydro-1H-2,1-benzothiazine 2,2-dioxide |
| 32 | 6-chloro-8-(4-(tetrahydro-2H-pyran-4-yl)phenyl)-3,4-dihydro-1H-2,1-benzothiazine 2,2-dioxide |
| 33 | 6-chloro-8-(2-naphthyl)-3,4-dihydro-1H-2,1-benzothiazine 2,2-dioxide |
| 34 | 6-chloro-8-(6-methoxy-2-naphthyl)-3,4-dihydro-1H-2,1-benzothiazine 2,2-dioxide |

TABLE 16-2-continued

| | |
|---|---|
| 35 | 6-chloro-8-(1-methyl-1H-indol-5-yl)-3,4-dihydro-1H-2,1-benzothiazine 2,2-dioxide |
| 36 | 6-chloro-8-(4-(4-chlorophenoxy)phenyl)-3,4-dihydro-1H-2,1-benzothiazine 2,2-dioxide |
| 37 | 6-chloro-8-(4-(3,4-dichlorophenoxy)phenyl)-3,4-dihydro-1H-2,1-benzothiazine 2,2-dioxide |
| 38 | 6-chloro-8-(4-(3-(trifluoromethyl)phenoxy)phenyl)-3,4-dihydro-1H-2,1-benzothiazine 2,2-dioxide |
| 39 | 6-chloro-8-(5-phenoxypyridin-2-yl)-3,4-dihydro-1H-2,1-benzothiazine 2,2-dioxide |
| 40 | 6-chloro-8-(6-phenoxypyridin-3-yl)-3,4-dihydro-1H-2,1-benzothiazine 2,2-dioxide |
| 41 | 6-chloro-8-(4-(pyridin-2-yloxy)phenyl)-3,4-dihydro-1H-2,1-benzothiazine 2,2-dioxide |
| 42 | 6-chloro-8-(4-((4-(trifluoromethyl)pyridin-2-yl)oxy)-phenyl)-3,4-dihydro-1H-2,1-benzothiazine 2,2-dioxide |
| 43 | 6-chloro-8-(4-(cyclohexyloxy)phenyl)-3,4-dihydro-1H-2,1-benzothiazine 2,2-dioxide |
| 44 | 6-chloro-8-(4-(tetrahydro-2H-pyran-4-yloxy)phenyl)-3,4-dihydro-1H-2,1-benzothiazine 2,2-dioxide |
| 45 | 6-chloro-8-(4-((4,4-difluorocyclohexyl)oxy)phenyl)-3,4-dihydro-1H-2,1-benzothiazine 2,2-dioxide |
| 46 | 6-chloro-8-(4-(2,2-dimethylpropoxy)phenyl)-3,4-dihydro-1H-2,1-benzothiazine 2,2-dioxide |
| 47 | 6-chloro-8-(4-(trifluoromethoxy)phenyl)-3,4-dihydro-1H-2,1-benzothiazine 2,2-dioxide |
| 48 | 6-chloro-8-(4-((3-fluorobenzyl)oxy)phenyl)-3,4-dihydro-1H-2,1-benzothiazine 2,2-dioxide |
| 49 | 8-(biphenyl-4-yl)-1H-4,2,1-benzoxathiazine 2,2-dioxide |
| 50 | 8-(4-phenoxyphenyl)-1H-4,2,1-benzoxathiazine 2,2-dioxide |
| 51 | 8-(4-(4-chloro-1H-pyrazol-1-yl)phenyl)-1H-4,2,1-benzoxathiazine 2,2-dioxide |
| 52 | 8-(4-(4-methyl-1H-imidazol-1-yl)phenyl)-1H-4,2,1-benzoxathiazine 2,2-dioxide |

TABLE 16-3

| | |
|---|---|
| 53 | 8-(5-phenylpyridin-2-yl)-1H-4,2,1-benzoxathiazine 2,2-dioxide |
| 54 | 8-(4-(pyridin-2-yl)phenyl)-1H-4,2,1-benzoxathiazine 2,2-dioxide |
| 55 | 8-(2-fluorobiphenyl-4-yl)-1H-4,2,1-benzoxathiazine 2,2-dioxide |
| 56 | 8-(4-(tetrahydro-2H-pyran-4-yl)phenyl)-1H-4,2,1-benzoxathiazine 2,2-dioxide |
| 57 | 8-(2-naphthyl)-1H-4,2,1-benzoxathiazine 2,2-dioxide |
| 58 | 8-(6-methoxy-2-naphthyl)-1H-4,2,1-benzoxathiazine 2,2-dioxide |
| 59 | 8-(1-methyl-1H-indol-5-yl)-1H-4,2,1-benzoxathiazine 2,2-dioxide |
| 60 | 8-(4-(4-chlorophenoxy)phenyl)-1H-4,2,1-benzoxathiazine 2,2-dioxide |
| 61 | 8-(4-(3,4-dichlorophenoxy)phenyl)-1H-4,2,1-benzoxathiazine 2,2-dioxide |
| 62 | 8-(4-(3-(trifluoromethyl)phenoxy)phenyl)-1H-4,2,1-benzoxathiazine 2,2-dioxide |
| 63 | 8-(5-phenoxypyridin-2-yl)-1H-4,2,1-benzoxathiazine 2,2-dioxide |
| 64 | 8-(6-phenoxypyridin-3-yl)-1H-4,2,1-benzoxathiazine 2,2-dioxide |
| 65 | 8-(4-(pyridin-2-yloxy)phenyl)-1H-4,2,1-benzoxathiazine 2,2-dioxide |
| 66 | 8-(4-((4-(trifluoromethyl)pyridin-2-yl)oxy)phenyl)-1H-4,2,1-benzoxathiazine 2,2-dioxide |
| 67 | 8-(4-(cyclohexyloxy)phenyl)-1H-4,2,1-benzoxathiazine 2,2-dioxide |
| 68 | 8-(4-(tetrahydro-2H-pyran-4-yloxy)phenyl)-1H-4,2,1-benzoxathiazine 2,2-dioxide |
| 69 | 8-(4-((4,4-difluorocyclohexyl)oxy)phenyl)-1H-4,2,1-benzoxathiazine 2,2-dioxide |
| 70 | 8-(4-(2,2-dimethylpropoxy)phenyl)-1H-4,2,1-benzoxathiazine 2,2-dioxide |
| 71 | 8-(4-(trifluoromethoxy)phenyl)-1H-4,2,1-benzoxathiazine 2,2-dioxide |
| 72 | 8-(4-((3-fluorobenzyl)oxy)phenyl)-1H-4,2,1-benzoxathiazine 2,2-dioxide |

TABLE 16-3-continued

| | |
|---|---|
| 73 | 8-(biphenyl-4-yl)-6-methyl-3,4-dihydro-1H-2,1-benzothiazine 2,2-dioxide |
| 74 | 6-methyl-8-(4-phenoxyphenyl)-3,4-dihydro-1H-2,1-benzothiazine 2,2-dioxide |
| 75 | 8-(4-(4-chloro-1H-pyrazol-1-yl)phenyl)-6-methyl-3,4-dihydro-1H-2,1-benzothiazine 2,2-dioxide |
| 76 | 6-methyl-8-(4-(4-methyl-1H-imidazol-1-yl)phenyl)-3,4-dihydro-1H-2,1-benzothiazine 2,2-dioxide |
| 77 | 6-methyl-8-(5-phenylpyridin-2-yl)-3,4-dihydro-1H-2,1-benzothiazine 2,2-dioxide |
| 78 | 6-methyl-8-(4-(pyridin-2-yl)phenyl)-3,4-dihydro-1H-2,1-benzothiazine 2,2-dioxide |
| 79 | 8-(2-fluorobiphenyl-4-yl)-6-methyl-3,4-dihydro-1H-2,1-benzothiazine 2,2-dioxide |

TABLE 16-4

| | |
|---|---|
| 80 | 6-methyl-8-(4-(tetrahydro-2H-pyran-4-yl)phenyl)-3,4-dihydro-1H-2,1-benzothiazine 2,2-dioxide |
| 81 | 6-methyl-8-(2-naphthyl)-3,4-dihydro-1H-2,1-benzothiazine 2,2-dioxide |
| 82 | 8-(6-methoxy-2-naphthyl)-6-methyl-3,4-dihydro-1H-2,1-benzothiazine 2,2-dioxide |
| 83 | 6-methyl-8-(1-methyl-1H-indol-5-yl)-3,4-dihydro-1H-2,1-benzothiazine 2,2-dioxide |
| 84 | 8-(4-(4-chlorophenoxy)phenyl)-6-methyl-3,4-dihydro-1H-2,1-benzothiazine 2,2-dioxide |
| 85 | 8-(4-(3,4-dichlorophenoxy)phenyl)-6-methyl-3,4-dihydro-1H-2,1-benzothiazine 2,2-dioxide |
| 86 | 6-methyl-8-(4-(3-(trifluoromethyl)phenoxy)phenyl)-3,4-dihydro-1H-2,1-benzothiazine 2,2-dioxide |
| 87 | 6-methyl-8-(5-phenoxypyridin-2-yl)-3,4-dihydro-1H-2,1-benzothiazine 2,2-dioxide |
| 88 | 6-methyl-8-(6-phenoxypyridin-3-yl)-3,4-dihydro-1H-2,1-benzothiazine 2,2-dioxide |
| 89 | 6-methyl-8-(4-(pyridin-2-yloxy)phenyl)-3,4-dihydro-1H-2,1-benzothiazine 2,2-dioxide |
| 90 | 6-methyl-8-(4-((4-(trifluoromethyl)pyridin-2-yl)oxy)phenyl)-3,4-dihydro-1H-2,1-benzothiazine 2,2-dioxide |
| 91 | 8-(4-(cyclohexyloxy)phenyl)-6-methyl-3,4-dihydro-1H-2,1-benzothiazine 2,2-dioxide |
| 92 | 6-methyl-8-(4-(tetrahydro-2H-pyran-4-yloxy)phenyl)-3,4-dihydro-1H-2,1-benzothiazine 2,2-dioxide |
| 93 | 8-(4-((4,4-difluorocyclohexyl)oxy)phenyl)-6-methyl-3,4-dihydro-1H-2,1-benzothiazine 2,2-dioxide |
| 94 | 8-(4-(2,2-dimethylpropoxy)phenyl)-6-methyl-3,4-dihydro-1H-2,1-benzothiazine 2,2-dioxide |
| 95 | 6-methyl-8-(4-(trifluoromethoxy)phenyl)-3,4-dihydro-1H-2,1-benzothiazine 2,2-dioxide |
| 96 | 8-(4-((3-fluorobenzyl)oxy)phenyl)-6-methyl-3,4-dihydro-1H-2,1-benzothiazine 2,2-dioxide |
| 97 | 8-(biphenyl-4-yl)-3,4-dihydro-1H-2,1,3-benzothiadiazine 2,2-dioxide |
| 98 | 8-(4-phenoxyphenyl)-3,4-dihydro-1H-2,1,3-benzothiadiazine 2,2-dioxide |
| 99 | 8-(4-(4-chloro-1H-pyrazol-1-yl)phenyl)-3,4-dihydro-1H-2,1,3-benzothiadiazine 2,2-dioxide |
| 100 | 8-(4-(4-methyl-1H-imidazol-1-yl)phenyl)-3,4-dihydro-1H-2,1,3-benzothiadiazine 2,2-dioxide |
| 101 | 8-(5-phenylpyridin-2-yl)-3,4-dihydro-1H-2,1,3-benzothiadiazine 2,2-dioxide |
| 102 | 8-(4-(pyridin-2-yl)phenyl)-3,4-dihydro-1H-2,1,3-benzothiadiazine 2,2-dioxide |
| 103 | 8-(2-fluorobiphenyl-4-yl)-3,4-dihydro-1H-2,1,3-benzothiadiazine 2,2-dioxide |
| 104 | 8-(4-(tetrahydro-2H-pyran-4-yl)phenyl)-3,4-dihydro-1H-2,1,3-benzothiadiazine 2,2-dioxide |
| 105 | 8-(2-naphthyl)-3,4-dihydro-1H-2,1,3-benzothiadiazine 2,2-dioxide |
| 106 | 8-(6-methoxy-2-naphthyl)-3,4-dihydro-1H-2,1,3-benzothiadiazine 2,2-dioxide |

TABLE 16-5

| | |
|---|---|
| 107 | 8-(1-methyl-1H-indol-5-yl)-3,4-dihydro-1H-2,1,3-benzothiadiazine 2,2-dioxide |
| 108 | 8-(4-(4-chlorophenoxy)phenyl)-3,4-dihydro-1H-2,1,3-benzothiadiazine 2,2-dioxide |
| 109 | 8-(4-(3,4-dichlorophenoxy)phenyl)-3,4-dihydro-1H-2,1,3-benzothiadiazine 2,2-dioxide |
| 110 | 8-(4-(3-(trifluoromethyl)phenoxy)phenyl)-3,4-dihydro-1H-2,1,3-benzothiadiazine 2,2-dioxide |
| 111 | 8-(5-phenoxypyridin-2-yl)-3,4-dihydro-1H-2,1,3-benzothiadiazine 2,2-dioxide |
| 112 | 8-(6-phenoxypyridin-3-yl)-3,4-dihydro-1H-2,1,3-benzothiadiazine 2,2-dioxide |
| 113 | 8-(4-(pyridin-2-yloxy)phenyl)-3,4-dihydro-1H-2,1,3-benzothiadiazine 2,2-dioxide |
| 114 | 8-(4-((4-(trifluoromethyl)pyridin-2-yl)oxy)phenyl)-3,4-dihydro-1H-2,1,3-benzothiadiazine 2,2-dioxide |
| 115 | 8-(4-(cyclohexyloxy)phenyl)-3,4-dihydro-1H-2,1,3-benzothiadiazine 2,2-dioxide |
| 116 | 8-(4-(tetrahydro-2H-pyran-4-yloxy)phenyl)-3,4-dihydro-1H-2,1,3-benzothiadiazine 2,2-dioxide |
| 117 | 8-(4-((4,4-difluorocyclohexyl)oxy)phenyl)-3,4-dihydro-1H-2,1,3-benzothiadiazine 2,2-dioxide |
| 118 | 8-(4-(2,2-dimethylpropoxy)phenyl)-3,4-dihydro-1H-2,1,3-benzothiadiazine 2,2-dioxide |
| 119 | 8-(4-(trifluoromethoxy)phenyl)-3,4-dihydro-1H-2,1,3-benzothiadiazine 2,2-dioxide |
| 120 | 8-(4-((3-fluorobenzyl)oxy)phenyl)-3,4-dihydro-1H-2,1,3-benzothiadiazine 2,2-dioxide |
| 121 | 8-(biphenyl-4-yl)-6-chloro-3,4-dihydro-1H-2,1,3-benzothiadiazine 2,2-dioxide |
| 122 | 6-chloro-8-(4-phenoxyphenyl)-3,4-dihydro-1H-2,1,3-benzothiadiazine 2,2-dioxide |
| 123 | 6-chloro-8-(4-(4-chloro-1H-pyrazol-1-yl)phenyl)-3,4-dihydro-1H-2,1,3-benzothiadiazine 2,2-dioxide |
| 124 | 6-chloro-8-(4-(4-methyl-1H-imidazol-1-yl)phenyl)-3,4-dihydro-1H-2,1,3-benzothiadiazine 2,2-dioxide |
| 125 | 6-chloro-8-(5-phenylpyridin-2-yl)-3,4-dihydro-1H-2,1,3-benzothiadiazine 2,2-dioxide |
| 126 | 6-chloro-8-(4-(pyridin-2-yl)phenyl)-3,4-dihydro-1H-2,1,3-benzothiadiazine 2,2-dioxide |
| 127 | 6-chloro-8-(2-fluorobiphenyl-4-yl)-3,4-dihydro-1H-2,1,3-benzothiadiazine 2,2-dioxide |
| 128 | 6-chloro-8-(4-(tetrahydro-2H-pyran-4-yl)phenyl)-3,4-dihydro-1H-2,1,3-benzothiadiazine 2,2-dioxide |
| 129 | 6-chloro-8-(2-naphthyl)-3,4-dihydro-1H-2,1,3-benzothiadiazine 2,2-dioxide |
| 130 | 6-chloro-8-(6-methoxy-2-naphthyl)-3,4-dihydro-1H-2,1,3-benzothiadiazine 2,2-dioxide |
| 131 | 6-chloro-8-(1-methyl-1H-indol-5-yl)-3,4-dihydro-1H-2,1,3-benzothiadiazine 2,2-dioxide |
| 132 | 6-chloro-8-(4-(4-chlorophenoxy)phenyl)-3,4-dihydro-1H-2,1,3-benzothiadiazine 2,2-dioxide |
| 133 | 6-chloro-8-(4-(3,4-dichlorophenoxy)phenyl)-3,4-dihydro-1H-2,1,3-benzothiadiazine 2,2-dioxide |

TABLE 16-6

| | |
|---|---|
| 134 | 6-chloro-8-(4-(3-(trifluoromethyl)phenoxy)phenyl)-3,4-dihydro-1H-2,1,3-benzothiadiazine 2,2-dioxide |
| 135 | 6-chloro-8-(5-phenoxypyridin-2-yl)-3,4-dihydro-1H-2,1,3-benzothiadiazine 2,2-dioxide |
| 136 | 6-chloro-8-(6-phenoxypyridin-3-yl)-3,4-dihydro-1H-2,1,3-benzothiadiazine 2,2-dioxide |
| 137 | 6-chloro-8-(4-(pyridin-2-yloxy)phenyl)-3,4-dihydro-1H-2,1,3-benzothiadiazine 2,2-dioxide |
| 138 | 6-chloro-8-(4-((4-(trifluoromethyl)pyridin-2-yl)oxy)phenyl)-3,4-dihydro-1H-2,1,3-benzothiadiazine 2,2-dioxide |
| 139 | 6-chloro-8-(4-(cyclohexyloxy)phenyl)-3,4-dihydro-1H-2,1,3-benzothiadiazine 2,2-dioxide |
| 140 | 6-chloro-8-(4-(tetrahydro-2H-pyran-4-yloxy)phenyl)-3,4-dihydro-1H-2,1,3-benzothiadiazine 2,2-dioxide |
| 141 | 6-chloro-8-(4-((4,4-difluorocyclohexyl)oxy)phenyl)-3,4-dihydro-1H-2,1,3-benzothiadiazine 2,2-dioxide |
| 142 | 6-chloro-8-(4-(2,2-dimethylpropoxy)phenyl)-3,4-dihydro-1H-2,1,3-benzothiadiazine 2,2-dioxide |
| 143 | 6-chloro-8-(4-(trifluoromethoxy)phenyl)-3,4-dihydro-1H-2,1,3-benzothiadiazine 2,2-dioxide |

TABLE 16-6-continued

| | |
|---|---|
| 144 | 6-chloro-8-(4-((3-fluorobenzyl)oxy)phenyl)-3,4-dihydro-1H-2,1,3-benzothiadiazine 2,2-dioxide |
| 145 | 8-(biphenyl-4-yl)-3,4-dihydro-1H-2,3-benzothiazine 2,2-dioxide |
| 146 | 8-(4-phenoxyphenyl)-3,4-dihydro-1H-2,3-benzothiazine 2,2-dioxide |
| 147 | 8-(4-(4-chloro-1H-pyrazol-1-yl)phenyl)-3,4-dihydro-1H-2,3-benzothiazine 2,2-dioxide |
| 148 | 8-(4-(4-methyl-1H-imidazol-1-yl)phenyl)-3,4-dihydro-1H-2,3-benzothiazine 2,2-dioxide |
| 149 | 8-(5-phenylpyridin-2-yl)-3,4-dihydro-1H-2,3-benzothiazine 2,2-dioxide |
| 150 | 8-(4-(pyridin-2-yl)phenyl)-3,4-dihydro-1H-2,3-benzothiazine 2,2-dioxide |
| 151 | 8-(2-fluorobiphenyl-4-yl)-3,4-dihydro-1H-2,3-benzothiazine 2,2-dioxide |
| 152 | 8-(4-(tetrahydro-2H-pyran-4-yl)phenyl)-3,4-dihydro-1H-2,3-benzothiazine 2,2-dioxide |
| 153 | 8-(2-naphthyl)-3,4-dihydro-1H-2,3-benzothiazine 2,2-dioxide |
| 154 | 8-(6-methoxy-2-naphthyl)-3,4-dihydro-1H-2,3-benzothiazine 2,2-dioxide |
| 155 | 8-(1-methyl-1H-indol-5-yl)-3,4-dihydro-1H-2,3-benzothiazine 2,2-dioxide |
| 156 | 8-(4-(4-chlorophenoxy)phenyl)-3,4-dihydro-1H-2,3-benzothiazine 2,2-dioxide |
| 157 | 8-(4-(3,4-dichlorophenoxy)phenyl)-3,4-dihydro-1H-2,3-benzothiazine 2,2-dioxide |
| 158 | 8-(4-(3-(trifluoromethyl)phenoxy)phenyl)-3,4-dihydro-1H-2,3-benzothiazine 2,2-dioxide |
| 159 | 8-(5-phenoxypyridin-2-yl)-3,4-dihydro-1H-2,3-benzothiazine 2,2-dioxide |
| 160 | 8-(6-phenoxypyridin-3-yl)-3,4-dihydro-1H-2,3-benzothiazine 2,2-dioxide |

TABLE 16-7

| | |
|---|---|
| 161 | 8-(4-(pyridin-2-yloxy)phenyl)-3,4-dihydro-1H-2,3-benzothiazine 2,2-dioxide |
| 162 | 8-(4-((4-(trifluoromethyl)pyridin-2-yl)oxy)phenyl)-3,4-dihydro-1H-2,3-benzothiazine 2,2-dioxide |
| 163 | 8-(4-(cyclohexyloxy)phenyl)-3,4-dihydro-1H-2,3-benzothiazine 2,2-dioxide |
| 164 | 8-(4-(tetrahydro-2H-pyran-4-yloxy)phenyl)-3,4-dihydro-1H-2,3-benzothiazine 2,2-dioxide |
| 165 | 8-(4-((4,4-difluorocyclohexyl)oxy)phenyl)-3,4-dihydro-1H-2,3-benzothiazine 2,2-dioxide |
| 166 | 8-(4-(2,2-dimethylpropoxy)phenyl)-3,4-dihydro-1H-2,3-benzothiazine 2,2-dioxide |
| 167 | 8-(4-(trifluoromethoxy)phenyl)-3,4-dihydro-1H-2,3-benzothiazine 2,2-dioxide |
| 168 | 8-(4-((3-fluorobenzyl)oxy)phenyl)-3,4-dihydro-1H-2,3-benzothiazine 2,2-dioxide |
| 169 | 6-(biphenyl-4-yl)-3,4-dihydropyrido[2,1-c][1,2,4]thiadiazine 2,2-dioxide |
| 170 | 6-(5-phenylpyridin-2-yl)-3,4-dihydropyrido[2,1-c][1,2,4]thiadiazine 2,2-dioxide |
| 171 | 6-(4-(4-methyl-1H-imidazol-1-yl)phenyl)-3,4-dihydropyrido[2,1-c][1,2,4]thiadiazine 2,2-dioxide |
| 172 | 6-(4-(4-chloro-1H-pyrazol-1-yl)phenyl)-3,4-dihydropyrido[2,1-c][1,2,4]thiadiazine 2,2-dioxide |
| 173 | 6-(2-naphthyl)-3,4-dihydropyrido[2,1-c][1,2,4]thiadiazine 2,2-dioxide |
| 174 | 6-(4-phenoxyphenyl)-3,4-dihydropyrido[2,1-c][1,2,4]thiadiazine 2,2-dioxide |
| 175 | 6-(4-(4-chlorophenoxy)phenyl)-3,4-dihydropyrido[2,1-c][1,2,4]thiadiazine 2,2-dioxide |
| 176 | 6-(4-(3-(trifluoromethyl)phenoxy)phenyl)-3,4-dihydropyrido[2,1-c][1,2,4]thiadiazine 2,2-dioxide |
| 177 | 6-(5-phenoxypyridin-2-yl)-3,4-dihydropyrido[2,1-c][1,2,4]thiadiazine 2,2-dioxide |
| 178 | 6-(6-phenoxypyridin-3-yl)-3,4-dihydropyrido[2,1-c][1,2,4]thiadiazine 2,2-dioxide |
| 179 | 6-(4-(pyridin-2-yloxy)phenyl)-3,4-dihydropyrido[2,1-c][1,2,4]thiadiazine 2,2-dioxide |
| 180 | 6-(4-(2,2-dimethylpropoxy)phenyl)-3,4-dihydropyrido[2,1-c][1,2,4]thiadiazine 2,2-dioxide |

TABLE 16-7-continued

| | |
|---|---|
| 181 | 6-(4-(trifluoromethoxy)phenyl)-3,4-dihydropyrido[2,1-c][1,2,4]thiadiazine 2,2-dioxide |
| 182 | 6-(4-(cyclohexyloxy)phenyl)-3,4-dihydropyrido[2,1-c][1,2,4]thiadiazine 2,2-dioxide |
| 183 | 6-(4-((4,4-difluorocyclohexyl)oxy)phenyl)-3,4-dihydropyrido[2,1-c][1,2,4]thiadiazine 2,2-dioxide |
| 184 | 6-(2-fluorobiphenyl-4-yl)-3,4-dihydropyrido[2,1-c][1,2,4]thiadiazine 2,2-dioxide |
| 185 | 6-(4-(tetrahydro-2H-pyran-4-yl)phenyl)-3,4-dihydropyrido[2,1-c][1,2,4]thiadiazine 2,2-dioxide |
| 186 | 6-(6-methoxy-2-naphthyl)-3,4-dihydropyrido[2,1-c][1,2,4]thiadiazine 2,2-dioxide |
| 187 | 6-(1-methyl-1H-indol-5-yl)-3,4-dihydropyrido[2,1-c][1,2,4]thiadiazine 2,2-dioxide |

TABLE 16-8

| | |
|---|---|
| 188 | 6-(4-(3,4-dichlorophenoxy)phenyl)-3,4-dihydropyrido[2,1-c][1,2,4]thiadiazine 2,2-dioxide |
| 189 | 6-(4-((4-(trifluoromethyl)pyridin-2-yl)oxy)phenyl)-3,4-dihydropyrido[2,1-c][1,2,4]thiadiazine 2,2-dioxide |
| 190 | 6-(4-((3-fluorobenzyl)oxy)phenyl)-3,4-dihydropyrido[2,1-c][1,2,4]thiadiazine 2,2-dioxide |
| 191 | 6-(4-(tetrahydro-2H-pyran-4-yloxy)phenyl)-3,4-dihydropyrido[2,1-c][1,2,4]thiadiazine 2,2-dioxide |
| 192 | 6-(4-(pyridin-2-yl)phenyl)-3,4-dihydropyrido[2,1-c][1,2,4]thiadiazine 2,2-dioxide |
| 193 | 6-(biphenyl-4-yl)-3,4-dihydro[1,3]thiazolo[2,3-c][1,2,4]thiadiazine 2,2-dioxide |
| 194 | 6-(5-phenylpyridin-2-yl)-3,4-dihydro[1,3]thiazolo[2,3-c][1,2,4]thiadiazine 2,2-dioxide |
| 195 | 6-(4-(4-methyl-1H-imidazol-1-yl)phenyl)-3,4-dihydro-[1,3]thiazolo[2,3-c][1,2,4]thiadiazine 2,2-dioxide |
| 196 | 6-(4-(4-chloro-1H-pyrazol-1-yl)phenyl)-3,4-dihydro-[1,3]thiazolo[2,3-c][1,2,4]thiadiazine 2,2-dioxide |
| 197 | 6-(2-naphthyl)-3,4-dihydro[1,3]thiazolo[2,3-c][1,2,4]thiadiazine 2,2-dioxide |
| 198 | 6-(4-phenoxyphenyl)-3,4-dihydro[1,3]thiazolo[2,3-c][1,2,4]thiadiazine 2,2-dioxide |
| 199 | 6-(4-(4-chlorophenoxy)phenyl)-3,4-dihydro[1,3]-thiazolo[2,3-c][1,2,4]thiadiazine 2,2-dioxide |
| 200 | 6-(4-(3-(trifluoromethyl)phenoxy)phenyl)-3,4-dihydro-[1,3]thiazolo[2,3-c][1,2,4]thiadiazine 2,2-dioxide |
| 201 | 6-(5-phenoxypyridin-2-yl)-3,4-dihydro[1,3]thiazolo[2,3-c][1,2,4]thiadiazine 2,2-dioxide |
| 202 | 6-(6-phenoxypyridin-3-yl)-3,4-dihydro[1,3]thiazolo[2,3-c][1,2,4]thiadiazine 2,2-dioxide |
| 203 | 6-(4-(pyridin-2-yloxy)phenyl)-3,4-dihydro[1,3]-thiazolo[2,3-c][1,2,4]thiadiazine 2,2-dioxide |
| 204 | 6-(4-(2,2-dimethylpropoxy)phenyl)-3,4-dihydro-[1,3]thiazolo[2,3-c][1,2,4]thiadiazine 2,2-dioxide |
| 205 | 6-(4-(trifluoromethoxy)phenyl)-3,4-dihydro-[1,3]thiazolo[2,3-c][1,2,4]thiadiazine 2,2-dioxide |
| 206 | 6-(4-(cyclohexyloxy)phenyl)-3,4-dihydro[1,3]-thiazolo[2,3-c][1,2,4]thiadiazine 2,2-dioxide |
| 207 | 6-(4-((4,4-difluorocyclohexyl)oxy)phenyl)-3,4-dihydro-[1,3]thiazolo[2,3-c][1,2,4]thiadiazine 2,2-dioxide |
| 208 | 6-(2-fluorobiphenyl-4-yl)-3,4-dihydro[1,3]thiazolo[2,3-c][1,2,4]thiadiazine 2,2-dioxide |
| 209 | 6-(4-(tetrahydro-2H-pyran-4-yl)phenyl)-3,4-dihydro-[1,3]thiazolo[2,3-c][1,2,4]thiadiazine 2,2-dioxide |
| 210 | 6-(6-methoxy-2-naphthyl)-3,4-dihydro[1,3]thiazolo[2,3-c][1,2,4]thiadiazine 2,2-dioxide |
| 211 | 6-(1-methyl-1H-indol-5-yl)-3,4-dihydro[1,3]thiazolo[2,3-c][1,2,4]thiadiazine 2,2-dioxide |
| 212 | 6-(4-(3,4-dichlorophenoxy)phenyl)-3,4-dihydro[1,3]-thiazolo[2,3-c][1,2,4]thiadiazine 2,2-dioxide |
| 213 | 6-(4-((4-(trifluoromethyl)pyridin-2-yl)oxy)phenyl)-3,4-dihydro[1,3]thiazolo[2,3-c][1,2,4]thiadiazine 2,2-dioxide |
| 214 | 6-(4-((3-fluorobenzyl)oxy)phenyl)-3,4-dihydro-[1,3]thiazolo[2,3-c][1,2,4]thiadiazine 2,2-dioxide |

TABLE 16-9

| | |
|---|---|
| 215 | 6-(4-(tetrahydro-2H-pyran-4-yloxy)phenyl)-3,4-dihydro-[1,3]thiazolo[2,3-c][1,2,4]thiadiazine 2,2-dioxide |
| 216 | 6-(4-(pyridin-2-yl)phenyl)-3,4-dihydro[1,3]thiazolo[2,3-c][1,2,4]thiadiazine 2,2-dioxide |
| 217 | 8-(biphenyl-4-yl)-3,4-dihydro-1H-pyrrolo[2,1-c][1,2,4]thiadiazine 2,2-dioxide |
| 218 | 8-(4-phenoxyphenyl)-3,4-dihydro-1H-pyrrolo[2,1-c][1,2,4]thiadiazine 2,2-dioxide |
| 219 | 8-(4-(4-chloro-1H-pyrazol-1-yl)phenyl)-3,4-dihydro-1H-pyrrolo[2,1-c][1,2,4]thiadiazine 2,2-dioxide |
| 220 | 8-(4-(4-methyl-1H-imidazol-1-yl)phenyl)-3,4-dihydro-1H-pyrrolo[2,1-c][1,2,4]thiadiazine 2,2-dioxide |
| 221 | 8-(5-phenylpyridin-2-yl)-3,4-dihydro-1H-pyrrolo[2,1-c][1,2,4]thiadiazine 2,2-dioxide |
| 222 | 8-(4-(pyridin-2-yl)phenyl)-3,4-dihydro-1H-pyrrolo[2,1-c][1,2,4]thiadiazine 2,2-dioxide |
| 223 | 8-(2-fluorobiphenyl-4-yl)-3,4-dihydro-1H-pyrrolo[2,1-c][1,2,4]thiadiazine 2,2-dioxide |
| 224 | 8-(4-(tetrahydro-2H-pyran-4-yl)phenyl)-3,4-dihydro-1H-pyrrolo[2,1-c][1,2,4]thiadiazine 2,2-dioxide |
| 225 | 8-(2-naphthyl)-3,4-dihydro-1H-pyrrolo[2,1-c][1,2,4]thiadiazine 2,2-dioxide |
| 226 | 8-(6-methoxy-2-naphthyl)-3,4-dihydro-1H-pyrrolo[2,1-c][1,2,4]thiadiazine 2,2-dioxide |
| 227 | 8-(1-methyl-1H-indol-5-yl)-3,4-dihydro-1H-pyrrolo[2,1-c][1,2,4]thiadiazine 2,2-dioxide |
| 228 | 8-(4-(4-chlorophenoxy)phenyl)-3,4-dihydro-1H-pyrrolo[2,1-c][1,2,4]thiadiazine 2,2-dioxide |
| 229 | 8-(4-(3,4-dichlorophenoxy)phenyl)-3,4-dihydro-1H-pyrrolo[2,1-c][1,2,4]thiadiazine 2,2-dioxide |
| 230 | 8-(4-(3-(trifluoromethyl)phenoxy)phenyl)-3,4-dihydro-1H-pyrrolo[2,1-c][1,2,4]thiadiazine 2,2-dioxide |
| 231 | 8-(5-phenoxypyridin-2-yl)-3,4-dihydro-1H-pyrrolo[2,1-c][1,2,4]thiadiazine 2,2-dioxide |
| 232 | 8-(6-phenoxypyridin-3-yl)-3,4-dihydro-1H-pyrrolo[2,1-c][1,2,4]thiadiazine 2,2-dioxide |
| 233 | 8-(4-(pyridin-2-yloxy)phenyl)-3,4-dihydro-1H-pyrrolo[2,1-c][1,2,4]thiadiazine 2,2-dioxide |
| 234 | 8-(4-((4-(trifluoromethyl)pyridin-2-yl)oxy)phenyl)-3,4-dihydro-1H-pyrrolo[2,1-c][1,2,4]thiadiazine 2,2-dioxide |
| 235 | 8-(4-(cyclohexyloxy)phenyl)-3,4-dihydro-1H-pyrrolo[2,1-c][1,2,4]thiadiazine 2,2-dioxide |
| 236 | 8-(4-(tetrahydro-2H-pyran-4-yloxy)phenyl)-3,4-dihydro-1H-pyrrolo[2,1-c][1,2,4]thiadiazine 2,2-dioxide |
| 237 | 8-(4-((4,4-difluorocyclohexyl)oxy)phenyl)-3,4-dihydro-1H-pyrrolo[2,1-c][1,2,4]thiadiazine 2,2-dioxide |
| 238 | 8-(4-(2,2-dimethylpropoxy)phenyl)-3,4-dihydro-1H-pyrrolo[2,1-c][1,2,4]thiadiazine 2,2-dioxide |
| 239 | 8-(4-(trifluoromethoxy)phenyl)-3,4-dihydro-1H-pyrrolo[2,1-c][1,2,4]thiadiazine 2,2-dioxide |
| 240 | 8-(4-((3-fluorobenzyl)oxy)phenyl)-3,4-dihydro-1H-pyrrolo[2,1-c][1,2,4]thiadiazine 2,2-dioxide |
| 241 | 8-(biphenyl-4-yl)-6-chloro-3,4-dihydro-1H-pyrrolo[2,1-c][1,2,4]thiadiazine 2,2-dioxide |

TABLE 16-10

| | |
|---|---|
| 242 | 6-chloro-8-(4-phenoxyphenyl)-3,4-dihydro-1H-pyrrolo[2,1-c][1,2,4]thiadiazine 2,2-dioxide |
| 243 | 6-chloro-8-(4-(4-chloro-1H-pyrazol-1-yl)phenyl)-3,4-dihydro-1H-pyrrolo[2,1-c][1,2,4]thiadiazine 2,2-dioxide |
| 244 | 6-chloro-8-(4-(4-methyl-1H-imidazol-1-yl)phenyl)-3,4-dihydro-1H-pyrrolo[2,1-c][1,2,4]thiadiazine 2,2-dioxide |
| 245 | 6-chloro-8-(5-phenylpyridin-2-yl)-3,4-dihydro-1H-pyrrolo[2,1-c][1,2,4]thiadiazine 2,2-dioxide |
| 246 | 6-chloro-8-(4-(pyridin-2-yl)phenyl)-3,4-dihydro-1H-pyrrolo[2,1-c][1,2,4]thiadiazine 2,2-dioxide |
| 247 | 6-chloro-8-(2-fluorobiphenyl-4-yl)-3,4-dihydro-1H-pyrrolo[2,1-c][1,2,4]thiadiazine 2,2-dioxide |
| 248 | 6-chloro-8-(4-(tetrahydro-2H-pyran-4-yl)phenyl)-3,4-dihydro-1H-pyrrolo[2,1-c][1,2,4]thiadiazine 2,2-dioxide |
| 249 | 6-chloro-8-(2-naphthyl)-3,4-dihydro-1H-pyrrolo[2,1-c][1,2,4]thiadiazine 2,2-dioxide |
| 250 | 6-chloro-8-(6-methoxy-2-naphthyl)-3,4-dihydro-1H-pyrrolo[2,1-c][1,2,4]thiadiazine 2,2-dioxide |
| 251 | 6-chloro-8-(1-methyl-1H-indol-5-yl)-3,4-dihydro-1H-pyrrolo[2,1-c][1,2,4]thiadiazine 2,2-dioxide |

TABLE 16-10-continued

| | |
|---|---|
| 252 | 6-chloro-8-(4-(4-chlorophenoxy)phenyl)-3,4-dihydro-1H-pyrrolo[2,1-c][1,2,4]thiadiazine 2,2-dioxide |
| 253 | 6-chloro-8-(4-(3,4-dichlorophenoxy)phenyl)-3,4-dihydro-1H-pyrrolo[2,1-c][1,2,4]thiadiazine 2,2-dioxide |
| 254 | 6-chloro-8-(4-(3-(trifluoromethyl)phenoxy)phenyl)-3,4-dihydro-1H-pyrrolo[2,1-c][1,2,4]thiadiazine 2,2-dioxide |
| 255 | 6-chloro-8-(5-phenoxypyridin-2-yl)-3,4-dihydro-1H-pyrrolo[2,1-c][1,2,4]thiadiazine 2,2-dioxide |
| 256 | 6-chloro-8-(6-phenoxypyridin-3-yl)-3,4-dihydro-1H-pyrrolo[2,1-c][1,2,4]thiadiazine 2,2-dioxide |
| 257 | 6-chloro-8-(4-(pyridin-2-yloxy)phenyl)-3,4-dihydro-1H-pyrrolo[2,1-c][1,2,4]thiadiazine 2,2-dioxide |
| 258 | 6-chloro-8-(4-((4-(trifluoromethyl)pyridin-2-yl)oxy)phenyl)-3,4-dihydro-1H-pyrrolo[2,1-c][1,2,4]thiadiazine 2,2-dioxide |
| 259 | 6-chloro-8-(4-(cyclohexyloxy)phenyl)-3,4-dihydro-1H-pyrrolo[2,1-c][1,2,4]thiadiazine 2,2-dioxide |
| 260 | 6-chloro-8-(4-(tetrahydro-2H-pyran-4-yloxy)phenyl)-3,4-dihydro-1H-pyrrolo[2,1-c][1,2,4]thiadiazine 2,2-dioxide |
| 261 | 6-chloro-8-(4-((4,4-difluorocyclohexyl)oxy)phenyl)-3,4-dihydro-1H-pyrrolo[2,1-c][1,2,4]thiadiazine 2,2-dioxide |
| 262 | 6-chloro-8-(4-(2,2-dimethylpropoxy)phenyl)-3,4-dihydro-1H-pyrrolo[2,1-c][1,2,4]thiadiazine 2,2-dioxide |
| 263 | 6-chloro-8-(4-(trifluoromethoxy)phenyl)-3,4-dihydro-1H-pyrrolo[2,1-c][1,2,4]thiadiazine 2,2-dioxide |
| 264 | 6-chloro-8-(4-((3-fluorobenzyl)oxy)phenyl)-3,4-dihydro-1H-pyrrolo[2,1-c][1,2,4]thiadiazine 2,2-dioxide |
| 265 | 9-(biphenyl-4-yl)-7-methyl-3,4-dihydropyridazino[6,1-c][1,2,4]thiadiazine 2,2-dioxide |
| 266 | 7-methyl-9-(4-phenoxyphenyl)-3,4-dihydropyridazino[6,1-c][1,2,4]thiadiazine 2,2-dioxide |
| 267 | 9-(4-(4-chloro-1H-pyrazol-1-yl)phenyl)-7-methyl-3,4-dihydropyridazino[6,1-c][1,2,4]thiadiazine 2,2-dioxide |
| 268 | 7-methyl-9-(4-(4-methyl-1H-imidazol-1-yl)phenyl)-3,4-dihydropyridazino[6,1-c][1,2,4]thiadiazine 2,2-dioxide |

TABLE 16-11

| | |
|---|---|
| 269 | 7-methyl-9-(5-phenylpyridin-2-yl)-3,4-dihydro-pyridazino[6,1-c][1,2,4]thiadiazine 2,2-dioxide |
| 270 | 7-methyl-9-(4-(pyridin-2-yl)phenyl)-3,4-dihydro-pyridazino[6,1-c][1,2,4]thiadiazine 2,2-dioxide |
| 271 | 9-(2-fluorobiphenyl-4-yl)-7-methyl-3,4-dihydro-pyridazino[6,1-c][1,2,4]thiadiazine 2,2-dioxide |
| 272 | 7-methyl-9-(4-(tetrahydro-2H-pyran-4-yl)phenyl)-3,4-dihydropyridazino[6,1-c][1,2,4]thiadiazine 2,2-dioxide |
| 273 | 7-methyl-9-(2-naphthyl)-3,4-dihydropyridazino[6,1-c][1,2,4]thiadiazine 2,2-dioxide |
| 274 | 9-(6-methoxy-2-naphthyl)-7-methyl-3,4-dihydro-pyridazino[6,1-c][1,2,4]thiadiazine 2,2-dioxide |
| 275 | 7-methyl-9-(1-methyl-1H-indol-5-yl)-3,4-dihydro-pyridazino[6,1-c][1,2,4]thiadiazine 2,2-dioxide |
| 276 | 9-(4-(4-chlorophenoxy)phenyl)-7-methyl-3,4-dihydro-pyridazino[6,1-c][1,2,4]thiadiazine 2,2-dioxide |
| 277 | 9-(4-(3,4-dichlorophenoxy)phenyl)-7-methyl-3,4-dihydropyridazino[6,1-c][1,2,4]thiadiazine 2,2-dioxide |
| 278 | 7-methyl-9-(4-(3-(trifluoromethyl)phenoxy)phenyl)-3,4-dihydropyridazino[6,1-c][1,2,4]thiadiazine 2,2-dioxide |
| 279 | 7-methyl-9-(5-phenoxypyridin-2-yl)-3,4-dihydro-pyridazino[6,1-c][1,2,4]thiadiazine 2,2-dioxide |
| 280 | 7-methyl-9-(6-phenoxypyridin-3-yl)-3,4-dihydro-pyridazino[6,1-c][1,2,4]thiadiazine 2,2-dioxide |
| 281 | 7-methyl-9-(4-(pyridin-2-yloxy)phenyl)-3,4-dihydro-pyridazino[6,1-c][1,2,4]thiadiazine 2,2-dioxide |
| 282 | 7-methyl-9-(4-((4-(trifluoromethyl)pyridin-2-yl)oxy)phenyl)-3,4-dihydropyridazino[6,1-c][1,2,4]thiadiazine 2,2-dioxide |
| 283 | 9-(4-(cyclohexyloxy)phenyl)-7-methyl-3,4-dihydro-pyridazino[6,1-c][1,2,4]thiadiazine 2,2-dioxide |
| 284 | 7-methyl-9-(4-(tetrahydro-2H-pyran-4-yloxy)phenyl)-3,4-dihydropyridazino[6,1-c][1,2,4]thiadiazine 2,2-dioxide |
| 285 | 9-(4-((4,4-difluorocyclohexyl)oxy)phenyl)-7-methyl-3,4-dihydropyridazino[6,1-c][1,2,4]thiadiazine 2,2-dioxide |
| 286 | 9-(4-(2,2-dimethylpropoxy)phenyl)-7-methyl-3,4-dihydropyridazino[6,1-c][1,2,4]thiadiazine 2,2-dioxide |
| 287 | 7-methyl-9-(4-(trifluoromethoxy)phenyl)-3,4-dihydro-pyridazino[6,1-c][1,2,4]thiadiazine 2,2-dioxide |

TABLE 16-11-continued

| | |
|---|---|
| 288 | 9-(4-((3-fluorobenzyl)oxy)phenyl)-7-methyl-3,4-dihydropyridazino[6,1-c][1,2,4]thiadiazine 2,2-dioxide |
| 289 | 8-(biphenyl-4-yl)-6,7-dichloro-3,4-dihydro-1H-pyrrolo[2,1-c][1,2,4]thiadiazine 2,2-dioxide |
| 290 | 6,7-dichloro-8-(4-phenoxyphenyl)-3,4-dihydro-1H-pyrrolo[2,1-c][1,2,4]thiadiazine 2,2-dioxide |
| 291 | 6,7-dichloro-8-(4-(4-chloro-1H-pyrazol-1-yl)phenyl)-3,4-dihydro-1H-pyrrolo[2,1-c][1,2,4]thiadiazine 2,2-dioxide |
| 292 | 6,7-dichloro-8-(4-(4-methyl-1H-imidazol-1-yl)phenyl)-3,4-dihydro-1H-pyrrolo[2,1-c][1,2,4]thiadiazine 2,2-dioxide |
| 293 | 6,7-dichloro-8-(5-phenylpyridin-2-yl)-3,4-dihydro-1H-pyrrolo[2,1-c][1,2,4]thiadiazine 2,2-dioxide |
| 294 | 6,7-dichloro-8-(4-(pyridin-2-yl)phenyl)-3,4-dihydro-1H-pyrrolo[2,1-c][1,2,4]thiadiazine 2,2-dioxide |
| 295 | 6,7-dichloro-8-(2-fluorobiphenyl-4-yl)-3,4-dihydro-1H-pyrrolo[2,1-c][1,2,4]thiadiazine 2,2-dioxide |

TABLE 16-12

| | |
|---|---|
| 296 | 6,7-dichloro-8-(4-(tetrahydro-2H-pyran-4-yl)phenyl)-3,4-dihydro-1H-pyrrolo[2,1-c][1,2,4]thiadiazine 2,2-dioxide |
| 297 | 6,7-dichloro-8-(2-naphthyl)-3,4-dihydro-1H-pyrrolo[2,1-c][1,2,4]thiadiazine 2,2-dioxide |
| 298 | 6,7-dichloro-8-(6-methoxy-2-naphthyl)-3,4-dihydro-1H-pyrrolo[2,1-c][1,2,4]thiadiazine 2,2-dioxide |
| 299 | 6,7-dichloro-8-(1-methyl-1H-indol-5-yl)-3,4-dihydro-1H-pyrrolo[2,1-c][1,2,4]thiadiazine 2,2-dioxide |
| 300 | 6,7-dichloro-8-(4-(4-chlorophenoxy)phenyl)-3,4-dihydro-1H-pyrrolo[2,1-c][1,2,4]thiadiazine 2,2-dioxide |
| 301 | 6,7-dichloro-8-(4-(3,4-dichlorophenoxy)phenyl)-3,4-dihydro-1H-pyrrolo[2,1-c][1,2,4]thiadiazine 2,2-dioxide |
| 302 | 6,7-dichloro-8-(4-(3-(trifluoromethyl)phenoxy)phenyl)-3,4-dihydro-1H-pyrrolo[2,1-c][1,2,4]thiadiazine 2,2-dioxide |
| 303 | 6,7-dichloro-8-(5-phenoxypyridin-2-yl)-3,4-dihydro-1H-pyrrolo[2,1-c][1,2,4]thiadiazine 2,2-dioxide |
| 304 | 6,7-dichloro-8-(6-phenoxypyridin-3-yl)-3,4-dihydro-1H-pyrrolo[2,1-c][1,2,4]thiadiazine 2,2-dioxide |
| 305 | 6,7-dichloro-8-(4-(pyridin-2-yloxy)phenyl)-3,4-dihydro-1H-pyrrolo[2,1-c][1,2,4]thiadiazine 2,2-dioxide |
| 306 | 6,7-dichloro-8-(4-((4-(trifluoromethyl)pyridin-2-yl)oxy)phenyl)-3,4-dihydro-1H-pyrrolo[2,1-c][1,2,4]thiadiazine 2,2-dioxide |
| 307 | 6,7-dichloro-8-(4-(cyclohexyloxy)phenyl)-3,4-dihydro-1H-pyrrolo[2,1-c][1,2,4]thiadiazine 2,2-dioxide |
| 308 | 6,7-dichloro-8-(4-(tetrahydro-2H-pyran-4-yloxy)phenyl)-3,4-dihydro-1H-pyrrolo[2,1-c][1,2,4]thiadiazine 2,2-dioxide |
| 309 | 6,7-dichloro-8-(4-((4,4-difluorocyclohexyl)oxy)phenyl)-3,4-dihydro-1H-pyrrolo[2,1-c][1,2,4]thiadiazine 2,2-dioxide |
| 310 | 6,7-dichloro-8-(4-(2,2-dimethylpropoxy)phenyl)-3,4-dihydro-1H-pyrrolo[2,1-c][1,2,4]thiadiazine 2,2-dioxide |
| 311 | 6,7-dichloro-8-(4-(trifluoromethoxy)phenyl)-3,4-dihydro-1H-pyrrolo[2,1-c][1,2,4]thiadiazine 2,2-dioxide |
| 312 | 6,7-dichloro-8-(4-((3-fluorobenzyl)oxy)phenyl)-3,4-dihydro-1H-pyrrolo[2,1-c][1,2,4]thiadiazine 2,2-dioxide |
| 313 | 8-(biphenyl-4-yl)-3,4-dihydro-1H-pyrazolo[5,1-c][1,2,4]thiadiazine 2,2-dioxide |
| 314 | 8-(4-phenoxyphenyl)-3,4-dihydro-1H-pyrazolo[5,1-c][1,2,4]thiadiazine 2,2-dioxide |
| 315 | 8-(4-(4-chloro-1H-pyrazol-1-yl)phenyl)-3,4-dihydro-1H-pyrazolo[5,1-c][1,2,4]thiadiazine 2,2-dioxide |
| 316 | 8-(4-(4-methyl-1H-imidazol-1-yl)phenyl)-3,4-dihydro-1H-pyrazolo[5,1-c][1,2,4]thiadiazine 2,2-dioxide |
| 317 | 8-(5-phenylpyridin-2-yl)-3,4-dihydro-1H-pyrazolo[5,1-c][1,2,4]thiadiazine 2,2-dioxide |
| 318 | 8-(4-(pyridin-2-yl)phenyl)-3,4-dihydro-1H-pyrazolo[5,1-c][1,2,4]thiadiazine 2,2-dioxide |
| 319 | 8-(2-fluorobiphenyl-4-yl)-3,4-dihydro-1H-pyrazolo[5,1-c][1,2,4]thiadiazine 2,2-dioxide |
| 320 | 8-(4-(tetrahydro-2H-pyran-4-yl)phenyl)-3,4-dihydro-1H-pyrazolo[5,1-c][1,2,4]thiadiazine 2,2-dioxide |
| 321 | 8-(2-naphthyl)-3,4-dihydro-1H-pyrazolo[5,1-c][1,2,4]thiadiazine 2,2-dioxide |
| 322 | 8-(6-methoxy-2-naphthyl)-3,4-dihydro-1H-pyrazolo[5,1-c][1,2,4]thiadiazine 2,2-dioxide |

TABLE 16-13

| | |
|---|---|
| 323 | 8-(1-methyl-1H-indol-5-yl)-3,4-dihydro-1H-pyrazolo[5,1-c][1,2,4]thiadiazine 2,2-dioxide |
| 324 | 8-(4-(4-chlorophenoxy)phenyl)-3,4-dihydro-1H-pyrazolo[5,1-c][1,2,4]thiadiazine 2,2-dioxide |
| 325 | 8-(4-(3,4-dichlorophenoxy)phenyl)-3,4-dihydro-1H-pyrazolo[5,1-c][1,2,4]thiadiazine 2,2-dioxide |
| 326 | 8-(4-(3-(trifluoromethyl)phenoxy)phenyl)-3,4-dihydro-1H-pyrazolo[5,1-c][1,2,4]thiadiazine 2,2-dioxide |
| 327 | 8-(5-phenoxypyridin-2-yl)-3,4-dihydro-1H-pyrazolo[5,1-c][1,2,4]thiadiazine 2,2-dioxide |
| 328 | 8-(6-phenoxypyridin-3-yl)-3,4-dihydro-1H-pyrazolo[5,1-c][1,2,4]thiadiazine 2,2-dioxide |
| 329 | 8-(4-(pyridin-2-yloxy)phenyl)-3,4-dihydro-1H-pyrazolo[5,1-c][1,2,4]thiadiazine 2,2-dioxide |
| 330 | 8-(4-((4-(trifluoromethyl)pyridin-2-yl)oxy)phenyl)-3,4-dihydro-1H-pyrazolo[5,1-c][1,2,4]thiadiazine 2,2-dioxide |
| 331 | 8-(4-(cyclohexyloxy)phenyl)-3,4-dihydro-1H-pyrazolo[5,1-c][1,2,4]thiadiazine 2,2-dioxide |
| 332 | 8-(4-(tetrahydro-2H-pyran-4-yloxy)phenyl)-3,4-dihydro-1H-pyrazolo[5,1-c][1,2,4]thiadiazine 2,2-dioxide |
| 333 | 8-(4-((4,4-difluorocyclohexyl)oxy)phenyl)-3,4-dihydro-1H-pyrazolo[5,1-c][1,2,4]thiadiazine 2,2-dioxide |
| 334 | 8-(4-(2,2-dimethylpropoxy)phenyl)-3,4-dihydro-1H-pyrazolo[5,1-c][1,2,4]thiadiazine 2,2-dioxide |
| 335 | 8-(4-(trifluoromethoxy)phenyl)-3,4-dihydro-1H-pyrazolo[5,1-c][1,2,4]thiadiazine 2,2-dioxide |
| 336 | 8-(4-((3-fluorobenzyl)oxy)phenyl)-3,4-dihydro-1H-pyrazolo[5,1-c][1,2,4]thiadiazine 2,2-dioxide |
| 337 | 8-(biphenyl-4-yl)-7-chloro-3,4-dihydro-1H-pyrazolo[5,1-c][1,2,4]thiadiazine 2,2-dioxide |
| 338 | 7-chloro-8-(4-phenoxyphenyl)-3,4-dihydro-1H-pyrazolo[5,1-c][1,2,4]thiadiazine 2,2-dioxide |
| 339 | 7-chloro-8-(4-(4-chloro-1H-pyrazol-1-yl)phenyl)-3,4-dihydro-1H-pyrazolo[5,1-c][1,2,4]thiadiazine 2,2-dioxide |
| 340 | 7-chloro-8-(4-(4-methyl-1H-imidazol-1-yl)phenyl)-3,4-dihydro-1H-pyrazolo[5,1-c][1,2,4]thiadiazine 2,2-dioxide |
| 341 | 7-chloro-8-(5-phenylpyridin-2-yl)-3,4-dihydro-1H-pyrazolo[5,1-c][1,2,4]thiadiazine 2,2-dioxide |
| 342 | 7-chloro-8-(4-(pyridin-2-yl)phenyl)-3,4-dihydro-1H-pyrazolo[5,1-c][1,2,4]thiadiazine 2,2-dioxide |
| 343 | 7-chloro-8-(2-fluorobiphenyl-4-yl)-3,4-dihydro-1H-pyrazolo[5,1-c][1,2,4]thiadiazine 2,2-dioxide |
| 344 | 7-chloro-8-(4-(tetrahydro-2H-pyran-4-yl)phenyl)-3,4-dihydro-1H-pyrazolo[5,1-c][1,2,4]thiadiazine 2,2-dioxide |
| 345 | 7-chloro-8-(2-naphthyl)-3,4-dihydro-1H-pyrazolo[5,1-c][1,2,4]thiadiazine 2,2-dioxide |
| 346 | 7-chloro-8-(6-methoxy-2-naphthyl)-3,4-dihydro-1H-pyrazolo[5,1-c][1,2,4]thiadiazine 2,2-dioxide |
| 347 | 7-chloro-8-(1-methyl-1H-indol-5-yl)-3,4-dihydro-1H-pyrazolo[5,1-c][1,2,4]thiadiazine 2,2-dioxide |
| 348 | 7-chloro-8-(4-(4-chlorophenoxy)phenyl)-3,4-dihydro-1H-pyrazolo[5,1-c][1,2,4]thiadiazine 2,2-dioxide |
| 349 | 7-chloro-8-(4-(3,4-dichlorophenoxy)phenyl)-3,4-dihydro-1H-pyrazolo[5,1-c][1,2,4]thiadiazine 2,2-dioxide |

TABLE 16-14

| | |
|---|---|
| 350 | 7-chloro-8-(4-(3-(trifluoromethyl)phenoxy)phenyl)-3,4-dihydro-1H-pyrazolo[5,1-c][1,2,4]thiadiazine 2,2-dioxide |
| 351 | 7-chloro-8-(5-phenoxypyridin-2-yl)-3,4-dihydro-1H-pyrazolo[5,1-c][1,2,4]thiadiazine 2,2-dioxide |
| 352 | 7-chloro-8-(6-phenoxypyridin-3-yl)-3,4-dihydro-1H-pyrazolo[5,1-c][1,2,4]thiadiazine 2,2-dioxide |
| 353 | 7-chloro-8-(4-(pyridin-2-yloxy)phenyl)-3,4-dihydro-1H-pyrazolo[5,1-c][1,2,4]thiadiazine 2,2-dioxide |
| 354 | 7-chloro-8-(4-((4-(trifluoromethyl)pyridin-2-yl)oxy)phenyl)-3,4-dihydro-1H-pyrazolo[5,1-c][1,2,4]thiadiazine 2,2-dioxide |
| 355 | 7-chloro-8-(4-(cyclohexyloxy)phenyl)-3,4-dihydro-1H-pyrazolo[5,1-c][1,2,4]thiadiazine 2,2-dioxide |
| 356 | 7-chloro-8-(4-(tetrahydro-2H-pyran-4-yloxy)phenyl)-3,4-dihydro-1H-pyrazolo[5,1-c][1,2,4]thiadiazine 2,2-dioxide |
| 357 | 7-chloro-8-(4-((4,4-difluorocyclohexyl)oxy)phenyl)-3,4-dihydro-1H-pyrazolo[5,1-c][1,2,4]thiadiazine 2,2-dioxide |
| 358 | 7-chloro-8-(4-(2,2-dimethylpropoxy)phenyl)-3,4-dihydro-1H-pyrazolo[5,1-c][1,2,4]thiadiazine 2,2-dioxide |

TABLE 16-14-continued

| | |
|---|---|
| 359 | 7-chloro-8-(4-(trifluoromethoxy)phenyl)-3,4-dihydro-1H-pyrazolo[5,1-c][1,2,4]thiadiazine 2,2-dioxide |
| 360 | 7-chloro-8-(4-((3-fluorobenzyl)oxy)phenyl)-3,4-dihydro-1H-pyrazolo[5,1-c][1,2,4]thiadiazine 2,2-dioxide |
| 361 | 8-(biphenyl-4-yl)-3,4-dihydro-1H-imidazo[5,1-c][1,2,4]thiadiazine 2,2-dioxide |
| 362 | 8-(4-phenoxyphenyl)-3,4-dihydro-1H-imidazo[5,1-c][1,2,4]thiadiazine 2,2-dioxide |
| 363 | 8-(4-(4-chloro-1H-pyrazol-1-yl)phenyl)-3,4-dihydro-1H-imidazo[5,1-c][1,2,4]thiadiazine 2,2-dioxide |
| 364 | 8-(4-(4-methyl-1H-imidazol-1-yl)phenyl)-3,4-dihydro-1H-imidazo[5,1-c][1,2,4]thiadiazine 2,2-dioxide |
| 365 | 8-(5-phenylpyridin-2-yl)-3,4-dihydro-1H-imidazo[5,1-c][1,2,4]thiadiazine 2,2-dioxide |
| 366 | 8-(4-(pyridin-2-yl)phenyl)-3,4-dihydro-1H-imidazo[5,1-c][1,2,4]thiadiazine 2,2-dioxide |
| 367 | 8-(2-fluorobiphenyl-4-yl)-3,4-dihydro-1H-imidazo[5,1-c][1,2,4]thiadiazine 2,2-dioxide |
| 368 | 8-(4-(tetrahydro-2H-pyran-4-yl)phenyl)-3,4-dihydro-1H-imidazo[5,1-c][1,2,4]thiadiazine 2,2-dioxide |
| 369 | 8-(2-naphthyl)-3,4-dihydro-1H-imidazo[5,1-c][1,2,4]thiadiazine 2,2-dioxide |
| 370 | 8-(6-methoxy-2-naphthyl)-3,4-dihydro-1H-imidazo[5,1-c][1,2,4]thiadiazine 2,2-dioxide |
| 371 | 8-(1-methyl-1H-indol-5-yl)-3,4-dihydro-1H-imidazo[5,1-c][1,2,4]thiadiazine 2,2-dioxide |
| 372 | 8-(4-(4-chlorophenoxy)phenyl)-3,4-dihydro-1H-imidazo[5,1-c][1,2,4]thiadiazine 2,2-dioxide |
| 373 | 8-(4-(3,4-dichlorophenoxy)phenyl)-3,4-dihydro-1H-imidazo[5,1-c][1,2,4]thiadiazine 2,2-dioxide |
| 374 | 8-(4-(3-(trifluoromethyl)phenoxy)phenyl)-3,4-dihydro-1H-imidazo[5,1-c][1,2,4]thiadiazine 2,2-dioxide |
| 375 | 8-(5-phenoxypyridin-2-yl)-3,4-dihydro-1H-imidazo[5,1-c][1,2,4]thiadiazine 2,2-dioxide |
| 376 | 8-(6-phenoxypyridin-3-yl)-3,4-dihydro-1H-imidazo[5,1-c][1,2,4]thiadiazine 2,2-dioxide |

TABLE 16-15

| | |
|---|---|
| 377 | 8-(4-(pyridin-2-yloxy)phenyl)-3,4-dihydro-1H-imidazo[5,1-c][1,2,4]thiadiazine 2,2-dioxide |
| 378 | 8-(4-((4-(trifluoromethyl)pyridin-2-yl)oxy)phenyl)-3,4-dihydro-1H-imidazo[5,1-c][1,2,4]thiadiazine 2,2-dioxide |
| 379 | 8-(4-cyclohexyloxy)phenyl)-3,4-dihydro-1H-imidazo[5,1-c][1,2,4]thiadiazine 2,2-dioxide |
| 380 | 8-(4-(tetrahydro-2H-pyran-4-yloxy)phenyl)-3,4-dihydro-1H-imidazo[5,1-c][1,2,4]thiadiazine 2,2-dioxide |
| 381 | 8-(4-((4,4-difluorocyclohexyl)oxy)phenyl)-3,4-dihydro-1H-imidazo[5,1-c][1,2,4]thiadiazine 2,2-dioxide |
| 382 | 8-(4-(2,2-dimethylpropoxy)phenyl)-3,4-dihydro-1H-imidazo[5,1-c][1,2,4]thiadiazine 2,2-dioxide |
| 383 | 8-(4-(trifluoromethoxy)phenyl)-3,4-dihydro-1H-imidazo[5,1-c][1,2,4]thiadiazine 2,2-dioxide |
| 384 | 8-(4-((3-fluorobenzyl)oxy)phenyl)-3,4-dihydro-1H-imidazo[5,1-c][1,2,4]thiadiazine 2,2-dioxide |
| 385 | 3-(biphenyl-4-yl)-6,7-dihydro-4H-[1,2,3]triazolo[5,1-c][1,2,4]thiadiazine 5,5-dioxide |
| 386 | 3-(4-phenoxyphenyl)-6,7-dihydro-4H-[1,2,3]triazolo[5,1-c][1,2,4]thiadiazine 5,5-dioxide |
| 387 | 3-(4-(4-chloro-1H-pyrazol-1-yl)phenyl)-6,7-dihydro-4H-[1,2,3]triazolo[5,1-c][1,2,4]thiadiazine 5,5-dioxide |
| 388 | 3-(4-(4-methyl-1H-imidazol-1-yl)phenyl)-6,7-dihydro-4H-[1,2,3]triazolo[5,1-c][1,2,4]thiadiazine 5,5-dioxide |
| 389 | 3-(5-phenylpyridin-2-yl)-6,7-dihydro-4H-[1,2,3]triazolo[5,1-c][1,2,4]thiadiazine 5,5-dioxide |
| 390 | 3-(4-(pyridin-2-yl)phenyl)-6,7-dihydro-4H-[1,2,3]triazolo[5,1-c][1,2,4]thiadiazine 5,5-dioxide |
| 391 | 3-(2-fluorobiphenyl-4-yl)-6,7-dihydro-4H-[1,2,3]triazolo[5,1-c][1,2,4]thiadiazine 5,5-dioxide |
| 392 | 3-(4-(tetrahydro-2H-pyran-4-yl)phenyl)-6,7-dihydro-4H-[1,2,3]triazolo[5,1-c][1,2,4]thiadiazine 5,5-dioxide |
| 393 | 3-(2-naphthyl)-6,7-dihydro-4H-[1,2,3]triazolo[5,1-c][1,2,4]thiadiazine 5,5-dioxide |
| 394 | 3-(6-methoxy-2-naphthyl)-6,7-dihydro-4H-[1,2,3]triazolo[5,1-c][1,2,4]thiadiazine 5,5-dioxide |
| 395 | 3-(1-methyl-1H-indol-5-yl)-6,7-dihydro-4H-[1,2,3]triazolo[5,1-c][1,2,4]thiadiazine 5,5-dioxide |

TABLE 16-15-continued

| | |
|---|---|
| 396 | 3-(4-(4-chlorophenoxy)phenyl)-6,7-dihydro-4H-[1,2,3]triazolo[5,1-c][1,2,4]thiadiazine 5,5-dioxide |
| 397 | 3-(4-(3,4-dichlorophenoxy)phenyl)-6,7-dihydro-4H-[1,2,3]triazolo[5,1-c][1,2,4]thiadiazine 5,5-dioxide |
| 398 | 3-(4-(3-(trifluoromethyl)phenoxy)phenyl)-6,7-dihydro-4H-[1,2,3]triazolo[5,1-c][1,2,4]thiadiazine 5,5-dioxide |
| 399 | 3-(5-phenoxypyridin-2-yl)-6,7-dihydro-4H-[1,2,3]triazolo[5,1-c][1,2,4]thiadiazine 5,5-dioxide |
| 400 | 3-(6-phenoxypyridin-3-yl)-6,7-dihydro-4H-[1,2,3]triazolo[5,1-c][1,2,4]thiadiazine 5,5-dioxide |
| 401 | 3-(4-(pyridin-2-yloxy)phenyl)-6,7-dihydro-4H-[1,2,3]triazolo[5,1-c][1,2,4]thiadiazine 5,5-dioxide |
| 402 | 3-(4-((4-(trifluoromethyl)pyridin-2-yl)oxy)phenyl)-6,7-dihydro-4H-[1,2,3]triazolo[5,1-c][1,2,4]thiadiazine 5,5-dioxide |
| 403 | 3-(4-(cyclohexyloxy)phenyl)-6,7-dihydro-4H-[1,2,3]triazolo[5,1-c][1,2,4]thiadiazine 5,5-dioxide |

TABLE 16-16

| | |
|---|---|
| 404 | 3-(4-(tetrahydro-2H-pyran-4-yloxy)phenyl)-6,7-dihydro-4H-[1,2,3]triazolo[5,1-c][1,2,4]thiadiazine 5,5-dioxide |
| 405 | 3-(4-((4,4-difluorocyclohexyl)oxy)phenyl)-6,7-dihydro-4H-[1,2,3]triazolo[5,1-c][1,2,4]thiadiazine 5,5-dioxide |
| 406 | 3-(4-(2,2-dimethylpropoxy)phenyl)-6,7-dihydro-4H-[1,2,3]triazolo[5,1-c][1,2,4]thiadiazine 5,5-dioxide |
| 407 | 3-(4-(trifluoromethoxy)phenyl)-6,7-dihydro-4H-[1,2,3]triazolo[5,1-c][1,2,4]thiadiazine 5,5-dioxide |
| 408 | 3-(4-((3-fluorobenzyl)oxy)phenyl)-6,7-dihydro-4H-[1,2,3]triazolo[5,1-c][1,2,4]thiadiazine 5,5-dioxide |
| 409 | 9-(biphenyl-4-yl)-7-chloro-3,4-dihydropyridazino[6,1-c][1,2,4]thiadiazine 2,2-dioxide |
| 410 | 7-chloro-9-(4-phenoxyphenyl)-3,4-dihydropyridazino[6,1-c][1,2,4]thiadiazine 2,2-dioxide |
| 411 | 7-chloro-9-(4-(4-chloro-1H-pyrazol-1-yl)phenyl)-3,4-dihydropyridazino[6,1-c][1,2,4]thiadiazine 2,2-dioxide |
| 412 | 7-chloro-9-(4-(4-methyl-1H-imidazol-1-yl)phenyl)-3,4-dihydropyridazino[6,1-c][1,2,4]thiadiazine 2,2-dioxide |
| 413 | 7-chloro-9-(5-phenylpyridin-2-yl)-3,4-dihydropyridazino[6,1-c][1,2,4]thiadiazine 2,2-dioxide |
| 414 | 7-chloro-9-(4-(pyridin-2-yl)phenyl)-3,4-dihydropyridazino[6,1-c][1,2,4]thiadiazine 2,2-dioxide |
| 415 | 7-chloro-9-(2-fluorobiphenyl-4-yl)-3,4-dihydropyridazino[6,1-c][1,2,4]thiadiazine 2,2-dioxide |
| 416 | 7-chloro-9-(4-(tetrahydro-2H-pyran-4-yl)phenyl)-3,4-dihydropyridazino[6,1-c][1,2,4]thiadiazine 2,2-dioxide |
| 417 | 7-chloro-9-(2-naphthyl)-3,4-dihydropyridazino[6,1-c][1,2,4]thiadiazine 2,2-dioxide |
| 418 | 7-chloro-9-(6-methoxy-2-naphthyl)-3,4-dihydropyridazino[6,1-c][1,2,4]thiadiazine 2,2-dioxide |
| 419 | 7-chloro-9-(1-methyl-1H-indol-5-yl)-3,4-dihydropyridazino[6,1-c][1,2,4]thiadiazine 2,2-dioxide |
| 420 | 7-chloro-9-(4-(4-chlorophenoxy)phenyl)-3,4-dihydropyridazino[6,1-c][1,2,4]thiadiazine 2,2-dioxide |
| 421 | 7-chloro-9-(4-(3,4-dichlorophenoxy)phenyl)-3,4-dihydropyridazino[6,1-c][1,2,4]thiadiazine 2,2-dioxide |
| 422 | 7-chloro-9-(4-(3-(trifluoromethyl)phenoxy)phenyl)-3,4-dihydropyridazino[6,1-c][1,2,4]thiadiazine 2,2-dioxide |
| 423 | 7-chloro-9-(5-phenoxypyridin-2-yl)-3,4-dihydropyridazino[6,1-c][1,2,4]thiadiazine 2,2-dioxide |
| 424 | 7-chloro-9-(6-phenoxypyridin-3-yl)-3,4-dihydropyridazino[6,1-c][1,2,4]thiadiazine 2,2-dioxide |
| 425 | 7-chloro-9-(4-(pyridin-2-yloxy)phenyl)-3,4-dihydropyridazino[6,1-c][1,2,4]thiadiazine 2,2-dioxide |
| 426 | 7-chloro-9-(4-((4-(trifluoromethyl)pyridin-2-yl)oxy)phenyl)-3,4-dihydropyridazino[6,1-c][1,2,4]thiadiazine 2,2-dioxide |
| 427 | 7-chloro-9-(4-(cyclohexyloxy)phenyl)-3,4-dihydropyridazino[6,1-c][1,2,4]thiadiazine 2,2-dioxide |
| 428 | 7-chloro-9-(4-(tetrahydro-2H-pyran-4-yloxy)phenyl)-3,4-dihydropyridazino[6,1-c][1,2,4]thiadiazine 2,2-dioxide |
| 429 | 7-chloro-9-(4-((4,4-difluorocyclohexyl)oxy)phenyl)-3,4-dihydropyridazino[6,1-c][1,2,4]thiadiazine 2,2-dioxide |
| 430 | 7-chloro-9-(4-(2,2-dimethylpropoxy)phenyl)-3,4-dihydropyridazino[6,1-c][1,2,4]thiadiazine 2,2-dioxide |

TABLE 16-17

| | | |
|---|---|---|
| 431 | 7-chloro-9-(4-(trifluoromethoxy)phenyl)-3,4-dihydro-pyridazino[6,1-c][1,2,4]thiadiazine 2,2-dioxide |
| 432 | 7-chloro-9-(4-((3-fluorobenzyl)oxy)phenyl)-3,4-dihydropyridazino[6,1-c][1,2,4]thiadiazine 2,2-dioxide |
| 433 | 9-(biphenyl-4-yl)-3,4-dihydropyrimido[6,1-c][1,2,4]thiadiazine 2,2-dioxide |
| 434 | 9-(4-phenoxyphenyl)-3,4-dihydropyrimido[6,1-c][1,2,4]thiadiazine 2,2-dioxide |
| 435 | 9-(4-(4-chloro-1H-pyrazol-1-yl)phenyl)-3,4-dihydropyrimido[6,1-c][1,2,4]thiadiazine 2,2-dioxide |
| 436 | 9-(4-(4-methyl-1H-imidazol-1-yl)phenyl)-3,4-dihydropyrimido[6,1-c][1,2,4]thiadiazine 2,2-dioxide |
| 437 | 9-(5-phenylpyridin-2-yl)-3,4-dihydropyrimido[6,1-c][1,2,4]thiadiazine 2,2-dioxide |
| 438 | 9-(4-(pyridin-2-yl)phenyl)-3,4-dihydropyrimido[6,1-c][1,2,4]thiadiazine 2,2-dioxide |
| 439 | 9-(4-fluorobiphenyl-4-yl)-3,4-dihydropyrimido[6,1-c][1,2,4]thiadiazine 2,2-dioxide |
| 440 | 9-(4-(tetrahydro-2H-pyran-4-yl)phenyl)-3,4-dihydropyrimido[6,1-c][1,2,4]thiadiazine 2,2-dioxide |
| 441 | 9-(2-naphthyl)-3,4-dihydropyrimido[6,1-c][1,2,4]thiadiazine 2,2-dioxide |
| 442 | 9-(6-methoxy-2-naphthyl)-3,4-dihydropyrimido[6,1-c][1,2,4]thiadiazine 2,2-dioxide |
| 443 | 9-(1-methyl-1H-indol-5-yl)-3,4-dihydropyrimido[6,1-c][1,2,4]thiadiazine 2,2-dioxide |
| 444 | 9-(4-(4-chlorophenoxy)phenyl)-3,4-dihydropyrimido[6,1-c][1,2,4]thiadiazine 2,2-dioxide |
| 445 | 9-(4-(3,4-dichlorophenoxy)phenyl)-3,4-dihydropyrimido[6,1-c][1,2,4]thiadiazine 2,2-dioxide |
| 446 | 9-(4-(3-(trifluoromethyl)phenoxy)phenyl)-3,4-dihydropyrimido[6,1-c][1,2,4]thiadiazine 2,2-dioxide |
| 447 | 9-(5-phenoxypyridin-2-yl)-3,4-dihydropyrimido[6,1-c][1,2,4]thiadiazine 2,2-dioxide |
| 448 | 9-(6-phenoxypyridin-3-yl)-3,4-dihydropyrimido[6,1-c][1,2,4]thiadiazine 2,2-dioxide |
| 449 | 9-(4-(pyridin-2-yloxy)phenyl)-3,4-dihydropyrimido[6,1-c][1,2,4]thiadiazine 2,2-dioxide |
| 450 | 9-(4-((4-(trifluoromethyl)pyridin-2-yl)oxy)phenyl)-3,4-dihydropyrimido[6,1-c][1,2,4]thiadiazine 2,2-dioxide |
| 451 | 9-(4-(cyclohexyloxy)phenyl)-3,4-dihydropyrimido[6,1-c][1,2,4]thiadiazine 2,2-dioxide |
| 452 | 9-(4-(tetrahydro-2H-pyran-4-yloxy)phenyl)-3,4-dihydropyrimido[6,1-c][1,2,4]thiadiazine 2,2-dioxide |
| 453 | 9-(4-((4,4-difluorocyclohexyl)oxy)phenyl)-3,4-dihydropyrimido[6,1-c][1,2,4]thiadiazine 2,2-dioxide |
| 454 | 9-(4-(2,2-dimethylpropoxy)phenyl)-3,4-dihydropyrimido[6,1-c][1,2,4]thiadiazine 2,2-dioxide |
| 455 | 9-(4-(trifluoromethoxy)phenyl)-3,4-dihydropyrimido[6,1-c][1,2,4]thiadiazine 2,2-dioxide |
| 456 | 9-(4-((3-fluorobenzyl)oxy)phenyl)-3,4-dihydropyrimido[6,1-c][1,2,4]thiadiazine 2,2-dioxide |
| 457 | 10-(biphenyl-4-yl)-4,5-dihydro-3H-pyrido[2,1-c][1,2,4]thiadiazepine 2,2-dioxide |

TABLE 16-18

| | | |
|---|---|---|
| 458 | 10-(2-fluorobiphenyl-4-yl)-4,5-dihydro-3H-pyrido[2,1-c][1,2,4]thiadiazepine 2,2-dioxide |
| 459 | 10-(5-phenylpyridin-2-yl)-4,5-dihydro-3H-pyrido[2,1-c][1,2,4]thiadiazepine 2,2-dioxide |
| 460 | 10-(4-(pyridin-2-yl)phenyl)-4,5-dihydro-3H-pyrido[2,1-c][1,2,4]thiadiazepine 2,2-dioxide |
| 461 | 10-(4-(tetrahydro-2H-pyran-4-yl)phenyl)-4,5-dihydro-3H-pyrido[2,1-c][1,2,4]thiadiazepine 2,2-dioxide |
| 462 | 10-(4-(4-methyl-1H-imidazol-1-yl)phenyl)-4,5-dihydro-3H-pyrido[2,1-c][1,2,4]thiadiazepine 2,2-dioxide |
| 463 | 10-(4-(4-chloro-1H-pyrazol-1-yl)phenyl)-4,5-dihydro-3H-pyrido[2,1-c][1,2,4]thiadiazepine 2,2-dioxide |
| 464 | 10-(2-naphthyl)-4,5-dihydro-3H-pyrido[2,1-c][1,2,4]thiadiazepine 2,2-dioxide |
| 465 | 10-(6-methoxy-2-naphthyl)-4,5-dihydro-3H-pyrido[2,1-c][1,2,4]thiadiazepine 2,2-dioxide |
| 466 | 10-(1-methyl-1H-indol-5-yl)-4,5-dihydro-3H-pyrido[2,1-c][1,2,4]thiadiazepine 2,2-dioxide |
| 467 | 10-(4-phenoxyphenyl)-4,5-dihydro-3H-pyrido[2,1-c][1,2,4]thiadiazepine 2,2-dioxide |

TABLE 16-18-continued

| | | |
|---|---|---|
| 468 | 10-(4-(4-chlorophenoxy)phenyl)-4,5-dihydro-3H-pyrido[2,1-c][1,2,4]thiadiazepine 2,2-dioxide |
| 469 | 10-(4-(3-(trifluoromethyl)phenoxy)phenyl)-4,5-dihydro-3H-pyrido[2,1-c][1,2,4]thiadiazepine 2,2-dioxide |
| 470 | 10-(4-(3,4-dichlorophenoxy)phenyl)-4,5-dihydro-3H-pyrido[2,1-c][1,2,4]thiadiazepine 2,2-dioxide |
| 471 | 10-(5-phenoxypyridin-2-yl)-4,5-dihydro-3H-pyrido[2,1-c][1,2,4]thiadiazepine 2,2-dioxide |
| 472 | 10-(6-phenoxypyridin-3-yl)-4,5-dihydro-3H-pyrido[2,1-c][1,2,4]thiadiazepine 2,2-dioxide |
| 473 | 10-(4-(pyridin-2-yloxy)phenyl)-4,5-dihydro-3H-pyrido[2,1-c][1,2,4]thiadiazepine 2,2-dioxide |
| 474 | 10-(4-((4-(trifluoromethyl)pyridin-2-yl)oxy)phenyl)-4,5-dihydro-3H-pyrido[2,1-c][1,2,4]thiadiazepine 2,2-dioxide |
| 475 | 10-(4-(2,2-dimethylpropoxy)phenyl)-4,5-dihydro-3H-pyrido[2,1-c][1,2,4]thiadiazepine 2,2-dioxide |
| 476 | 10-(4-(trifluoromethoxy)phenyl)-4,5-dihydro-3H-pyrido[2,1-c][1,2,4]thiadiazepine 2,2-dioxide |
| 477 | 10-(4-((3-fluorobenzyl)oxy)phenyl)-4,5-dihydro-3H-pyrido[2,1-c][1,2,4]thiadiazepine 2,2-dioxide |
| 478 | 10-(4-(cyclohexyloxy)phenyl)-4,5-dihydro-3H-pyrido[2,1-c][1,2,4]thiadiazepine 2,2-dioxide |
| 479 | 10-(4-((4,4-difluorocyclohexyl)oxy)phenyl)-4,5-dihydro-3H-pyrido[2,1-c][1,2,4]thiadiazepine 2,2-dioxide |
| 480 | 10-(4-(tetrahydro-2H-pyran-4-yloxy)phenyl)-4,5-dihydro-3H-pyrido[2,1-c][1,2,4]thiadiazepine 2,2-dioxide |
| 481 | 10-(biphenyl-4-yl)-8-chldro-4,5-dihydro-3H-pyrido[2,1-c][1,2,4]thiadiazepine 2,2-dioxide |
| 482 | 8-chloro-10-(2-fluorobiphenyl-4-yl)-4,5-dihydro-3H-pyrido[2,1-c][1,2,4]thiadiazepine 2,2-dioxide |
| 483 | 8-chloro-10-(5-phenylpyridin-2-yl)-4,5-dihydro-3H-pyrido[2,1-c][1,2,4]thiadiazepine 2,2-dioxide |
| 484 | 8-chloro-10-(4-(pyridin-2-yl)phenyl)-4,5-dihydro-3H-pyrido[2,1-c][1,2,4]thiadiazepine 2,2-dioxide |

TABLE 16-19

| | | |
|---|---|---|
| 485 | 8-chloro-10-(4-(tetrahydro-2H-pyran-4-yl)phenyl)-4,5-dihydro-3H-pyrido[2,1-c][1,2,4]thiadiazepine 2,2-dioxide |
| 486 | 8-chloro-10-(4-(4-methyl-1H-imidazol-1-yl)phenyl)-4,5-dihydro-3H-pyrido[2,1-c][1,2,4]thiadiazepine 2,2-dioxide |
| 487 | 8-chloro-10-(4-(4-chloro-1H-pyrazol-1-yl)phenyl)-4,5-dihydro-3H-pyrido[2,1-c][1,2,4]thiadiazepine 2,2-dioxide |
| 488 | 8-chloro-10-(2-naphthyl)-4,5-dihydro-3H-pyrido[2,1-c][1,2,4]thiadiazepine 2,2-dioxide |
| 489 | 8-chloro-10-(6-methoxy-2-naphthyl)-4,5-dihydro-3H-pyrido[2,1-c][1,2,4]thiadiazepine 2,2-dioxide |
| 490 | 8-chloro-10-(1-methyl-1H-indol-5-yl)-4,5-dihydro-3H-pyrido[2,1-c][1,2,4]thiadiazepine 2,2-dioxide |
| 491 | 8-chloro-10-(4-phenoxyphenyl)-4,5-dihydro-3H-pyrido[2,1-c][1,2,4]thiadiazepine 2,2-dioxide |
| 492 | 8-chloro-10-(4-(4-chlorophenoxy)phenyl)-4,5-dihydro-3H-pyrido[2,1-c][1,2,4]thiadiazepine 2,2-dioxide |
| 493 | 8-chloro-10-(4-(3-(trifluoromethyl)phenoxy)phenyl)-4,5-dihydro-3H-pyrido[2,1-c][1,2,4]thiadiazepine 2,2-dioxide |
| 494 | 8-chloro-10-(4-(3,4-dichlorophenoxy)phenyl)-4,5-dihydro-3H-pyrido[2,1-c][1,2,4]thiadiazepine 2,2-dioxide |
| 495 | 8-chloro-10-(5-phenoxypyridin-2-yl)-4,5-dihydro-3H-pyrido[2,1-c][1,2,4]thiadiazepine 2,2-dioxide |
| 496 | 8-chloro-10-(6-phenoxypyridin-3-yl)-4,5-dihydro-3H-pyrido[2,1-c][1,2,4]thiadiazepine 2,2-dioxide |
| 497 | 8-chloro-10-(4-(pyridin-2-yloxy)phenyl)-4,5-dihydro-3H-pyrido[2,1-c][1,2,4]thiadiazepine 2,2-dioxide |
| 498 | 8-chloro-10-(4-((4-(trifluoromethyl)pyridin-2-yl)oxy)phenyl)-4,5-dihydro-3H-pyrido[2,1-c][1,2,4]thiadiazepine 2,2-dioxide |
| 499 | 8-chloro-10-(4-(2,2-dimethylpropoxy)phenyl)-4,5-dihydro-3H-pyrido[2,1-c][1,2,4]thiadiazepine 2,2-dioxide |
| 500 | 8-chloro-10-(4-(trifluoromethoxy)phenyl)-4,5-dihydro-3H-pyrido[2,1-c][1,2,4]thiadiazepine 2,2-dioxide |
| 501 | 8-chloro-10-(4-((3-fluorobenzyl)oxy)phenyl)-4,5-dihydro-3H-pyrido[2,1-c][1,2,4]thiadiazepine 2,2-dioxide |
| 502 | 8-chloro-10-(4-(cyclohexyloxy)phenyl)-4,5-dihydro-3H-pyrido[2,1-c][1,2,4]thiadiazepine 2,2-dioxide |
| 503 | 8-chloro-10-(4-((4,4-difluorocyclohexyl)oxy)phenyl)-4,5-dihydro-3H-pyrido[2,1-c][1,2,4]thiadiazepine 2,2-dioxide |

TABLE 16-19-continued

| | |
|---|---|
| 504 | 8-chloro-10-(4-(tetrahydro-2H-pyran-4-yloxy)phenyl)-4,5-dihydro-3H-pyrido[2,1-c][1,2,4]thiadiazepine 2,2-dioxide |
| 505 | 9-(biphenyl-4-yl)pyrido[2,1-c][1,2,4]thiadiazine 2,2-dioxide |
| 506 | 9-(4-phenoxyphenyl)pyrido[2,1-c][1,2,4]thiadiazine 2,2-dioxide |
| 507 | 9-(4-(4-chloro-1H-pyrazol-1-yl)phenyl)pyrido[2,1-c][1,2,4]thiadiazine 2,2-dioxide |
| 508 | 9-(4-(4-methyl-1H-imidazol-1-yl)phenyl)pyrido[2,1-c][1,2,4]thiadiazine 2,2-dioxide |
| 509 | 9-(5-phenylpyridin-2-yl)pyrido[2,1-c][1,2,4]thiadiazine 2,2-dioxide |
| 510 | 9-(4-(pyridin-2-yl)phenyl)pyrido[2,1-c][1,2,4]thiadiazine 2,2-dioxide |
| 511 | 9-(2-fluorobiphenyl-4-yl)pyrido[2,1-c][1,2,4]thiadiazine 2,2-dioxide |

TABLE 16-20

| | |
|---|---|
| 512 | 9-(4-(tetrahydro-2H-pyran-4-yl)phenyl)pyrido[2,1-c][1,2,4]thiadiazine 2,2-dioxide |
| 513 | 9-(2-naphthyl)pyrido[2,1-c][1,2,4]thiadiazine 2,2-dioxide |
| 514 | 9-(6-methoxy-2-naphthyl)pyrido[2,1-c][1,2,4]thiadiazine 2,2-dioxide |
| 515 | 9-(1-methyl-1H-indol-5-yl)pyrido[2,1-c][1,2,4]thiadiazine 2,2-dioxide |
| 516 | 9-(4-(4-chlorophenoxy)phenyl)pyrido[2,1-c][1,2,4]thiadiazine 2,2-dioxide |
| 517 | 9-(4-(3,4-dichlorophenoxy)phenyl)pyrido[2,1-c][1,2,4]thiadiazine 2,2-dioxide |
| 518 | 9-(4-(3-(trifluoromethyl)phenoxy)phenyl)pyrido[2,1-c][1,2,4]thiadiazine 2,2-dioxide |
| 519 | 9-(5-phenoxypyridin-2-yl)pyrido[2,1-c][1,2,4]thiadiazine 2,2-dioxide |
| 520 | 9-(6-phenoxypyridin-3-yl)pyrido[2,1-c][1,2,4]thiadiazine 2,2-dioxide |
| 521 | 9-(4-(pyridin-2-yloxy)phenyl)pyrido[2,1-c][1,2,4]thiadiazine 2,2-dioxide |
| 522 | 9-(4-((4-(trifluoromethyl)pyridin-2-yl)oxy)phenyl)-pyrido[2,1-c][1,2,4]thiadiazine 2,2-dioxide |
| 523 | 9-(4-(cyclohexyloxy)phenyl)pyrido[2,1-c][1,2,4]thiadiazine 2,2-dioxide |
| 524 | 9-(4-(tetrahydro-2H-pyran-4-yloxy)phenyl)pyrido[2,1-c][1,2,4]thiadiazine 2,2-dioxide |
| 525 | 9-(4-((4,4-difluorocyclohexyl)oxy)phenyl)pyrido[2,1-c][1,2,4]thiadiazine 2,2-dioxide |
| 526 | 9-(4-(2,2-dimethylpropoxy)phenyl)pyrido[2,1-c][1,2,4]thiadiazine 2,2-dioxide |
| 527 | 9-(4-(trifluoromethoxy)phenyl)pyrido[2,1-c][1,2,4]thiadiazine 2,2-dioxide |
| 528 | 9-(4-((3-fluorobenzyl)oxy)phenyl)pyrido[2,1-c][1,2,4]thiadiazine 2,2-dioxide |
| 529 | 9-(biphenyl-4-yl)-7-chloropyrido[2,1-c][1,2,4]thiadiazine 2,2-dioxide |
| 530 | 7-chloro-9-(4-phenoxyphenyl)pyrido[2,1-c][1,2,4]thiadiazine 2,2-dioxide |
| 531 | 7-chloro-9-(4-(4-chloro-1H-pyrazol-1-yl)phenyl)pyrido[2,1-c][1,2,4]thiadiazine 2,2-dioxide |
| 532 | 7-chloro-9-(4-(4-methyl-1H-imidazol-1-yl)phenyl)pyrido[2,1-c][1,2,4]thiadiazine 2,2-dioxide |
| 533 | 7-chloro-9-(5-phenylpyridin-2-yl)pyrido[2,1-c][1,2,4]thiadiazine 2,2-dioxide |
| 534 | 7-chloro-9-(4-(pyridin-2-yl)phenyl)pyrido[2,1-c][1,2,4]thiadiazine 2,2-dioxide |
| 535 | 7-chloro-9-(2-fluorobiphenyl-4-yl)pyrido[2,1-c][1,2,4]thiadiazine 2,2-dioxide |
| 536 | 7-chloro-9-(4-(tetrahydro-2H-pyran-4-yl)phenyl)pyrido[2,1-c][1,2,4]thiadiazine 2,2-dioxide |
| 537 | 7-chloro-9-(2-naphthyl)pyrido[2,1-c][1,2,4]thiadiazine 2,2-dioxide |
| 538 | 7-chloro-9-(6-methoxy-2-naphthyl)pyrido[2,1-c][1,2,4]thiadiazine 2,2-dioxide |

TABLE 16-21

| | |
|---|---|
| 539 | 7-chloro-9-(1-methyl-1H-indol-5-yl)pyrido[2,1-c][1,2,4]thiadiazine 2,2-dioxide |
| 540 | 7-chloro-9-(4-(4-chlorophenoxy)phenyl)pyrido[2,1-c][1,2,4]thiadiazine 2,2-dioxide |
| 541 | 7-chloro-9-(4-(3,4-dichlorophenoxy)phenyl)pyrido[2,1-c][1,2,4]thiadiazine 2,2-dioxide |
| 542 | 7-chloro-9-(4-(3-(trifluoromethyl)phenoxy)-phenyl)pyrido[2,1-c][1,2,4]thiadiazine 2,2-dioxide |
| 543 | 7-chloro-9-(5-phenoxypyridin-2-yl)pyrido[2,1-c][1,2,4]thiadiazine 2,2-dioxide |
| 544 | 7-chloro-9-(6-phenoxypyridin-3-yl)pyrido[2,1-c][1,2,4]thiadiazine 2,2-dioxide |
| 545 | 7-chloro-9-(4-(pyridin-2-yloxy)phenyl)pyrido[2,1-c][1,2,4]thiadiazine 2,2-dioxide |
| 546 | 7-chloro-9-(4-((4-(trifluoromethyl)pyridin-2-yl)oxy)phenyl)pyrido[2,1-c][1,2,4]thiadiazine 2,2-dioxide |
| 547 | 7-chloro-9-(4-(cyclohexyloxy)phenyl)pyrido[2,1-c][1,2,4]thiadiazine 2,2-dioxide |
| 548 | 7-chloro-9-(4-(tetrahydro-2H-pyran-4-yloxy)phenyl)-pyrido[2,1-c][1,2,4]thiadiazine 2,2-dioxide |
| 549 | 7-chloro-9-(4-((4,4-difluorocyclohexyl)-oxy)phenyl)pyrido[2,1-c][1,2,4]thiadiazine 2,2-dioxide |
| 550 | 7-chloro-9-(4-(2,2-dimethylpropoxy)phenyl)pyrido[2,1-c][1,2,4]thiadiazine 2,2-dioxide |
| 551 | 7-chloro-9-(4-(trifluoromethoxy)phenyl)pyrido[2,1-c][1,2,4]thiadiazine 2,2-dioxide |
| 552 | 7-chloro-9-(4-((3-fluorobenzyl)oxy)phenyl)pyrido[2,1-c][1,2,4]thiadiazine 2,2-dioxide |
| 553 | 8-(biphenyl-4-yl)-3,4-dihydro-1H-2,1-benzothiazine 2,2-dioxide |
| 554 | 8-(4-phenoxyphenyl)-3,4-dihydro-1H-2,1-benzothiazine 2,2-dioxide |
| 555 | 8-(4-(4-chloro-1H-pyrazol-1-yl)phenyl)-3,4-dihydro-1H-2,1-benzothiazine 2,2-dioxide |
| 556 | 8-(4-(4-methyl-1H-imidazol-1-yl)phenyl)-3,4-dihydro-1H-2,1-benzothiazine 2,2-dioxide |
| 557 | 8-(5-phenylpyridin-2-yl)-3,4-dihydro-1H-2,1-benzothiazine 2,2-dioxide, |
| 558 | 8-(4-(pyridin-2-yl)phenyl)-3,4-dihydro-1H-2,1-benzothiazine 2,2-dioxide |
| 559 | 8-(2-fluorobiphenyl-4-yl)-3,4-dihydro-1H-2,1-benzothiazine 2,2-dioxide |
| 560 | 8-(4-(tetrahydro-2H-pyran-4-yl)phenyl)-3,4-dihydro-1H-2,1-benzothiazine 2,2-dioxide |
| 561 | 8-(2-naphthyl)-3,4-dihydro-1H-2,1-benzothiazine 2,2-dioxide |
| 562 | 8-(6-methoxy-2-naphthyl)-3,4-dihydro-1H-2,1-benzothiazine 2,2-dioxide |
| 563 | 8-(1-methyl-1H-indol-5-yl)-3,4-dihydro-1H-2,1-benzothiazine 2,2-dioxide |
| 564 | 8-(4-(4-chlorophenoxy)phenyl)-3,4-dihydro-1H-2,1-benzothiazine 2,2-dioxide |
| 565 | 8-(4-(3,4-dichlorophenoxy)phenyl)-3,4-dihydro-1H-2,1-benzothiazine 2,2-dioxide |

TABLE 16-22

| | |
|---|---|
| 566 | 8-(4-(3-(trifluoromethyl)phenoxy)phenyl)-3,4-dihydro-1H-2,1-benzothiazine 2,2-dioxide |
| 567 | 8-(5-phenoxypyridin-2-yl)-3,4-dihydro-1H-2,1-benzothiazine 2,2-dioxide |
| 568 | 8-(6-phenoxypyridin-3-yl)-3,4-dihydro-1H-2,1-benzothiazine 2,2-dioxide |
| 569 | 8-(4-(pyridin-2-yloxy)phenyl)-3,4-dihydro-1H-2,1-benzothiazine 2,2-dioxide |
| 570 | 8-(4-((4-(trifluoromethyl)pyridin-2-yl)oxy)phenyl)-3,4-dihydro-1H-2,1-benzothiazine 2,2-dioxide |
| 571 | 8-(4-(cyclohexyloxy)phenyl)-3,4-dihydro-1H-2,1-benzothiazine 2,2-dioxide |
| 572 | 8-(4-(tetrahydro-2H-pyran-4-yloxy)phenyl)-3,4-dihydro-1H-2,1-benzothiazine 2,2-dioxide |
| 573 | 8-(4-((4,4-difluorocyclohexyl)oxy)phenyl)-3,4-dihydro-1H-2,1-benzothiazine 2,2-dioxide |
| 574 | 8-(4-(2,2-dimethylpropoxy)phenyl)-3,4-dihydro-1H-2,1-benzothiazine 2,2-dioxide |
| 575 | 8-(4-(trifluoromethoxy)phenyl)-3,4-dihydro-1H-2,1-benzothiazine 2,2-dioxide |

TABLE 16-22-continued

| 576 | 8-(4-((3-fluorobenzyl)oxy)phenyl)-3,4-dihydro-1H-2,1-benzothiazine 2,2-dioxide |

Preparation Example 1

A medicament containing the compound of the present invention as an active ingredient can be produced, for example, in the following formulation.

1. capsule

| | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the remaining (4) and the whole is sealed in a gelatin capsule.

2. tablet

| | |
|---|---|
| (1) compound obtained in Example 1 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. Thereto is added the remaining (4) and (5) and the mixture is compression formed into a tablet.

Preparation Example 2

The compound obtained in Example 1 (50 mg) is dissolved in the Japanese Pharmacopoeia distilled water for injection (50 mL), and the Japanese Pharmacopoeia distilled water for injection is added to 100 mL. The solution is filtered under sterilization conditions, the solution (1 mL) is taken and filled in a vial for injection under sterilization conditions, and the vial is freeze-dried and sealed.

Experimental Example 1

(1) Construction of Expression Gene

Human GluR1 flip cDNA was amplified by PCR method using forward primer ACTGAATTCGCCACCATGCAGCACATTTTTGCCTTCTTCTGC (SEQ ID NO: 1) and reverse primer CCGCGGCCGCTTACAATCCCGTGGCTCCCAAG (SEQ ID NO: 2) artificially synthesized using human brain-derived cDNA (BD Bioscience) as a template. The amplified product was digested with restriction enzymes EcoRI, NotI (TAKARA SHUZO CO. LTD.) and incorporated into the same site of pcDNA3.1(+) (Invitrogen) to construct pcDNA3.1(+)/human GluR1 flip gene. Human stargazin cDNA was amplified by PCR method using forward primer GGTCTCGAGGCCACCATGGGGCTGTTTGATCGAGGTGTTCA (SEQ ID NO: 3) and reverse primer GTTGGATCCTTATACGGGGGTGGTCCGGCGGTTGGCTGTG (SEQ ID NO: 4) artificially synthesized using human hippocampus cDNA as a template. The amplified product was digested with restriction enzymes XhoI, BamHI (TAKARA SHUZO CO. LTD.) and incorporated into the same site of pcDNA3.1(−) (Invitrogen) to construct pcDNA3.1 Zeo(−)/human stargazing gene.

(2) Construction of GluR1 Flip/Stargazin Expressing Cell

CHO-K1 cells passaged in a culture medium (Ham's F12 medium (Invitrogen) added with 10% inactivated fetal bovine serum (Morgate) and penicillin, streptomycin (Invitrogen)) were detached using 0.05% trypsin and 0.53 mM EDTA (Invitrogen) diluted with D-PBS(−). The detached cells were suspended in a culture medium, and recovered by centrifugation at 1,000 rpm. The recovered cells were re-suspended in D-PBS(−) and added into 0.4 cm electroporation cuvette (BioRad). pcDNA3.1(+)/human GluR1 flip gene (5 μg) and pcDNA3.1 Zeo(−)/human stargazin gene (15 μg) were added, and introduced into CHO-K1 cells under the conditions of 950 pFd, 250 mV and using Gene Pulser II (BioRad). The introduced cells were cultured overnight in a culture medium. The next day, using a selection medium (culture medium added with zeocin (Invitrogen) at 250 μg/mL), the cells were plated in a 96 well plate at 250 cells/well. The clones showing drug resistance were selected, and GluR1 flip/stargazin expression clones were selected by an assay method shown below using calcium influx as an index.

(3) Measurement Method of AMPA Receptor Function-Enhancing Activity of Compound, Using Calcium Influx as an Index CHO-K1/GluR1 flip/stargazin-expressing cells were plated on a 96 well black bottom transparent plate (coaster) at $3 \times 10^4$ cells/well, and cultured for 2 days in a $CO_2$ incubator (SANYO ELECTRIC Co. Ltd.) at 37° C. The medium of the cell plate was removed, a calcium indicator (Calcium4 Assay Kit, Molecular Device) dissolved in a liquid obtained by adding 1.25 mM probenecid (Invitrogen) to an assay buffer (140 mM NaCl, 5 mM KCl, 10 mM Glucose, 2 mM $CaCl_2$, 1 mM $MgCl_2$, 10 mM HEPES, pH 7.4, 0.1% BSA (SIGMA)) was added at 100 μL/well, and left in a $CO_2$ incubator at 37° C. for 1 hr. A cell plate was set on CellLux (PerkinElmer), a mixture (50 μL) of 9 mM glutamic acid (final concentration 3 mM) diluted with an assay buffer and a test compound (test compound final concentration 30 μM) was added, and variation in the amount of fluorescence was measured for 2 min. The variation of fluorescence level of a well added with final concentration 3 mM glutamic acid and 300 μM cyclothiazide (TOCRIS, prepared from 100 mM dimethyl sulfoxide solution) was defined as 100%, the variation of fluorescence level of a well containing final concentration 3 mM glutamic acid and 0.33% dimethyl sulfoxide was defined as 0%, and the activity of the m compound was calculated by the following formula.

$$\text{activity (\%)} = (X-C)/(T-C) \times 100$$

T: variation of fluorescence level of well added with final concentration 3 mM of glutamic acid and 300 μM cyclothiazide C: variation of fluorescence level of well added with final concentration 3 mM of glutamic acid alone X: variation of fluorescence level of well added with final concentration 3 mM of glutamic acid and 30 μM test compound The obtained results are shown in Table 17.

TABLE 17

| Example No. | activity (%) |
|---|---|
| 1 | 26 |
| 2 | 74 |
| 15 | 92 |
| 16 | 87 |
| 23 | 61 |
| 28 | 91 |
| 30 | 22 |
| 38 | 87 |
| 45 | 77 |
| 47 | 87 |

INDUSTRIAL APPLICABILITY

The compound of the present invention has an AMPA receptor function enhancing action, and is useful as a prophylactic or therapeutic drug for depression, schizophrenia, Alzheimer's disease, attention deficit hyperactivity disorder (ADHD) and the like.

This application is based on patent application No. 2012-025610 filed in Japan, the contents of which are encompassed in full herein.

SEQUENCE LISTING FREE TEXT

SEQ ID NO: 1 is a forward primer for GluR1 flip cDNA.
SEQ ID NO: 2 is a reverse primer for GluR1 flip cDNA.
SEQ ID NO: 3 is a forward primer for stargazin cDNA.
SEQ ID NO: 4 is a reverse primer for stargazin cDNA.

The invention claimed is:
1. A compound represented by the formula (I)

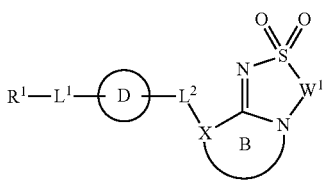

wherein
R¹ is
(1) $C_{1-6}$ alkyl optionally substituted by 1 to 3 substituents selected from a halogen atom and $C_{1-6}$ alkoxy;
(2) $C_{3-7}$ cycloalkyl;
(3) phenyl optionally substituted by 1 to 3 substituents selected from a halogen atom, cyano, $C_{1-6}$ alkyl optionally substituted by 1 to 3 halogen atoms and $C_{1-6}$ alkoxy;
(4) dihydrobenzofuranyl;
(5) benzodioxolyl substituted by 1 to 3 halogen atoms;
(6) pyridyl optionally substituted by 1 to 3 substituents selected from a halogen atom and $C_{1-6}$ alkyl optionally substituted by 1 to 3 halogen atoms;
(7) pyrimidinyl;
(8) isoxazolyl substituted by 1 to 3 $C_{1-6}$ alkyls;
(9) tetrahydrofuranyl; or
(10) pyrazolyl;
L¹ is a bond, —O— or CH₂—O—;
ring D is a benzene ring;
a partial structure:

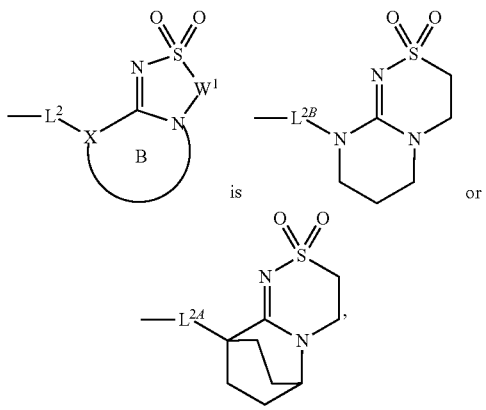

wherein
$L^{2A}$ is a bond or —O—CH₂—; or
$L^{2B}$ is a bond,
or a salt thereof.

2. The compound according to claim 1, wherein R¹ is
(1) $C_{1-6}$ alkyl;
(2) phenyl optionally substituted by 1 to 3 substituents selected from a halogen atom, cyano and $C_{1-6}$ alkyl optionally substituted by 1 to 3 halogen atoms;
(3) pyridyl substituted by 1 to 3 substituents selected from $C_{1-6}$ alkyl substituted by 1 to 3 halogen atoms;
(4) pyrimidinyl; or
(5) tetrahydrofuranyl;
L¹ is —O— or —CH₂—O—;
ring D is a benzene ring;
the partial structure:

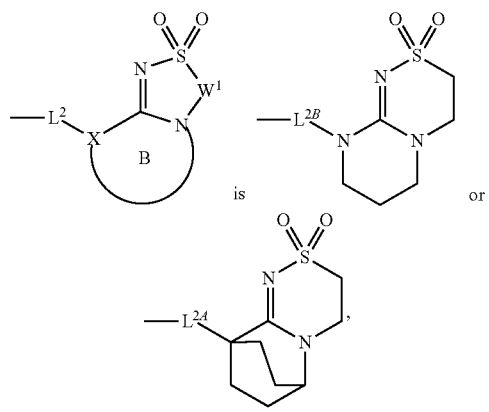

wherein,
$L^{2A}$ is a bond; or
$L^{2B}$ is a bond,
or a salt thereof.

3. 9-(4-(4-Chlorophenoxy)phenyl)-3,4,6,7,8,9-hexahydro-6,9-ethanopyrido[2,1-c][1,2,4]thiadiazine 2,2-dioxide or a salt thereof.

4. 9-(4-(4-Chlorophenoxy)phenyl)-3,4,6,7,8,9-hexahydropyrimido[2,1-c][1,2,4]thiadiazine 2,2-dioxide or a salt thereof.

5. 9-(4-((6-(Trifluoromethyl)pyridin-2-yl)oxy)phenyl)-3,4,6,7,8,9-hexahydro-6,9-ethanopyrido[2,1-c][1,2,4]thiadiazine 2,2-dioxide or a salt thereof.

6. A pharmaceutical composition comprising the compound according to claim 1 or a salt thereof and a pharmaceutically acceptable carrier.

7. The pharmaceutical composition according to claim 6, which is an AMPA receptor function enhancer.

8. The pharmaceutical composition according to claim 6, which is a therapeutic drug for depression, schizophrenia or attention deficit hyperactivity disorder.

9. A method of treating depression, schizophrenia or attention deficit hyperactivity disorder in a mammal, comprising administering an effective amount of the compound according to claim 1 or a salt thereof to the mammal.

* * * * *

```
                       SEQUENCE LISTING

<160> NUMBER OF SEQ ID NOS: 4

<210> SEQ ID NO 1
<211> LENGTH: 42
<212> TYPE: DNA
<213> ORGANISM: Artificial
<220> FEATURE:
<223> OTHER INFORMATION: Forward primer for GluR1 flip cDNA

<400> SEQUENCE: 1
actgaattcg ccaccatgca gcacattttt gccttcttct gc                        42

<210> SEQ ID NO 2
<211> LENGTH: 32
<212> TYPE: DNA
<213> ORGANISM: Artificial
<220> FEATURE:
<223> OTHER INFORMATION: Reverse primer for GluR1 flip cDNA

<400> SEQUENCE: 2
ccgcggccgc ttacaatccc gtggctccca ag                                  32

<210> SEQ ID NO 3
<211> LENGTH: 41
<212> TYPE: DNA
<213> ORGANISM: Artificial
<220> FEATURE:
<223> OTHER INFORMATION: Forward primer for stargazin cDNA

<400> SEQUENCE: 3
ggtctcgagg ccaccatggg gctgtttgat cgaggtgttc a                         41

<210> SEQ ID NO 4
<211> LENGTH: 40
<212> TYPE: DNA
<213> ORGANISM: Artificial
<220> FEATURE:
<223> OTHER INFORMATION: Reverse primer for stargazin cDNA

<400> SEQUENCE: 4
gttggatcct tatacggggg tggtccggcg gttggctgtg                           40
```